United States Patent
Chen et al.

(10) Patent No.: US 10,745,346 B2
(45) Date of Patent: Aug. 18, 2020

(54) AGONISTS OF PROTEIN TYROSINE PHOSPHATASE SHP-1

(71) Applicants: Kuen-Feng Chen, Taipei (TW); Chung-Wai Shiau, Taipei (TW)

(72) Inventors: Kuen-Feng Chen, Taipei (TW); Chung-Wai Shiau, Taipei (TW)

( * ) Notice: Subject to any disclaimer, the term of this patent is extended or adjusted under 35 U.S.C. 154(b) by 8 days.

(21) Appl. No.: 15/754,838

(22) PCT Filed: Aug. 31, 2016

(86) PCT No.: PCT/CN2016/097663
§ 371 (c)(1),
(2) Date: Feb. 23, 2018

(87) PCT Pub. No.: WO2017/036405
PCT Pub. Date: Mar. 9, 2017

(65) Prior Publication Data
US 2018/0237385 A1  Aug. 23, 2018

Related U.S. Application Data

(60) Provisional application No. 62/213,130, filed on Sep. 2, 2015.

(51) Int. Cl.

| | |
|---|---|
| C07C 275/36 | (2006.01) |
| C07C 235/82 | (2006.01) |
| C07C 237/16 | (2006.01) |
| C07C 317/26 | (2006.01) |
| A61K 31/155 | (2006.01) |
| C07C 237/24 | (2006.01) |
| C07D 265/36 | (2006.01) |
| C07D 213/84 | (2006.01) |
| C07D 401/12 | (2006.01) |

(52) U.S. Cl.
CPC ......... *C07C 275/36* (2013.01); *A61K 31/155* (2013.01); *C07C 235/82* (2013.01); *C07C 237/16* (2013.01); *C07C 237/24* (2013.01); *C07C 317/26* (2013.01); *C07D 213/84* (2013.01); *C07D 265/36* (2013.01); *C07D 401/12* (2013.01)

(58) Field of Classification Search
CPC .. A61K 31/155; C07C 235/82; C07C 237/16; C07C 237/24; C07C 317/26; C07D 213/84; C07D 265/36; C07D 401/12

USPC ........................................................ 546/300
See application file for complete search history.

(56) References Cited

U.S. PATENT DOCUMENTS

| | | | |
|---|---|---|---|
| 2,745,874 A | 5/1956 | Schetty et al. | |
| 2,867,658 A | 1/1959 | Frick et al. | |
| 3,906,033 A | 9/1975 | Biland et al. | |
| 9,090,617 B1 * | 7/2015 | Shiau | C07D 471/04 |
| 9,216,950 B2 * | 12/2015 | Shiau | C07D 213/81 |
| 2006/0233705 A1 * | 10/2006 | Schuller | G01N 33/574 424/1.49 |
| 2014/0148482 A1 | 5/2014 | Ou et al. | |
| 2020/0016100 A1 * | 1/2020 | Su | A61P 17/00 |

FOREIGN PATENT DOCUMENTS

| | | |
|---|---|---|
| BE | 617117 A | 10/1962 |
| EP | 0512211 A2 | 11/1992 |
| GB | 1326481 | 8/1973 |
| WO | WO2003068228 A | 8/2003 |
| WO | WO2004078747 A | 9/2004 |
| WO | WO2007119055 A | 10/2007 |
| WO | WO2013020014 A1 | 2/2013 |
| WO | WO20130597884 A | 4/2013 |
| WO | WO2015051149 A1 | 4/2015 |
| WO | WO-2018054354 A1 * | 3/2018 |

OTHER PUBLICATIONS

Huang; Cancer Letters 349 (2014) 136-143. Jul. 28, 2014. (Year: 2014).*
Chemical Abstracts STN Registry Database, Record for RN 1347937-65-8, entered on Dec. 4, 2011. (Year: 2011).*
Chen; European Journal of Medicinal Chemistry 2012, 55, 220-227. (Year: 2012).*
Sun; European Journal of Medicinal Chemistry 2010, 45, 2299-2306. (Year: 2010).*
Tai, W.T. et al., "SC-60, a Dimer-Based Sorafenib Derivative, Shows a Better Anti-Hepatocellular Carcinoma Effect than Sorafenib in a Preclinical Hepatocellular Carcinoma Model", Mol. Cancer Ther., vol. 13, No. 1, Jan. 31, 2014.

* cited by examiner

Primary Examiner — Daniel R Carcanague
(74) Attorney, Agent, or Firm — WPAT, PC

(57) ABSTRACT

Some novel compounds are provided in this disclosure. These novel compounds have potential SHP-1 agonist activity for being used in treating cancer.

6 Claims, No Drawings

AGONISTS OF PROTEIN TYROSINE PHOSPHATASE SHP-1

BACKGROUND

Field of Invention

The present invention relates to new compounds having protein tyrosine phosphatase SHP-1 agonist activity and treatment methods using the same.

Description of Related Art

Src homology region 2 domain-containing phosphatase-1 (SHP-1), a protein tyrosine phosphatase with two Src homology 2 (SH2) domains, is a regulator of various intracellular signaling molecules, such as signal transducer and activator of transcription 3 (STAT3), KIT, CD22, CD5, CD72, SHPS-1, TIMP (metalloproteinases), CDK2, p27, SRC, ZAP70, IL-10, NF-κB, Lck, 3BP2, Lyn and cyclin D1.

STAT3 is a transcription factor which regulates inflammation, cell growth and survival by modulating the expression of target genes. It acts as an oncogene which is constitutively active in many cancers including liver, lung, head and neck, prostate, and breast as well as myeloma and leukemia. A key regulator of STAT3 activity is SHP-1. From a mechanistic perspective, SHP-1 exhibits protein phosphatase activity which reduces the level of Phospho-STAT3 (P-STAT) and subsequently blocks the dimerization of P-STAT3. Therefore, expression of target genes, such as cyclin D1 and survivin transcribed by STAT3, is significantly reduced.

In addition, studies of SHP-1 protein and SHP-1 mRNA showed that expression level of SHP-1 was low in most cancer cells; and genetic increase in SHP-1 in cancer cells resulted in the suppression of cell growth, suggesting that the SHP-1 gene acts as a tumor suppressor. From the drug discovery point of view, development of a small molecule which can reduce P-STAT3 and increase SHP-1 level is a promising direction for cancer therapy.

SHP-1 also plays an important role in bone remodeling, a process of bone-forming osteoblasts and bone-resorbing osteoclasts. Loss function of SHP-1 results in osteoclast activation and eventually leads to osteoporosis. Therefore, enhancement of SHP-1 activity might be a direction for osteoporosis patient.

In addition, increase of SHP-1 is benefit for the macrophages of multiple sclerosis patients.

SUMMARY

Accordingly, some novel compounds are provided in this disclosure. These novel compounds have potential SHP-1 agonist activity for being used in treating cancer.

According to an embodiment of this disclosure, a compound I having a chemical structure shown below is provided.

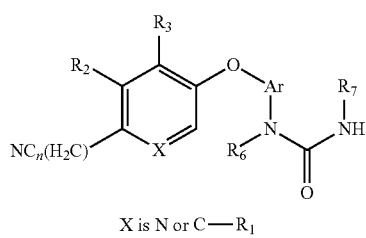

X is N or C—$R_1$

In the chemical structure of compound I,
n is 0 or 1.
X is N or C—$R_1$.
$R_1$ is H or Cl.

$R_2$ is H, a halide or an alkyl group. The halide is F, Cl, or Br, for example. The alkyl group is $CH_3$ or $CH_2CH_3$, for example.

$R_3$ is H, a halide or an alkyl group. The halide is F, Cl, or Br, for example. The alkyl group is $CH_3$ or $CH_2CH_3$, for example.

$R_2$ and $R_3$ also can together form a bivalent saturated or unsaturated group, such as

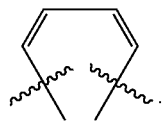

Ar is an unsubstituted or substituted phenylene group or a naphthalenylene group. The phenylene group may be

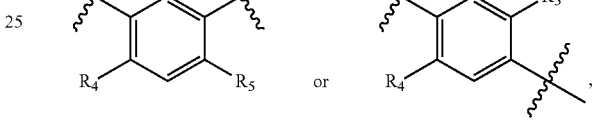

for example. The naphthalenylene group may be

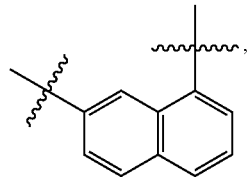

for example.

$R_4$ is H, a halide or an alkyl group. The halide is F or Cl, for example. The alkyl group is $CH_3$ or $CH_2CH_3$, for example.

$R_5$ is H, a halide, an alkyl group, an alkoxyl group or a hydroxyl group. The halide is F or Cl, for example. The alkyl group is $CH_3$ or $CH_2CH_3$, for example.

$R_6$ is H or a hydroxyl group. $R_5$ and $R_6$ also can together form a bivalent saturated or unsaturated group, such as

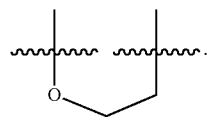 [SMILES: *CCO*]

$R_7$ is an unsubstituted or substituted aromatic group. $R_7$ is a substituted phenyl group, a substituted

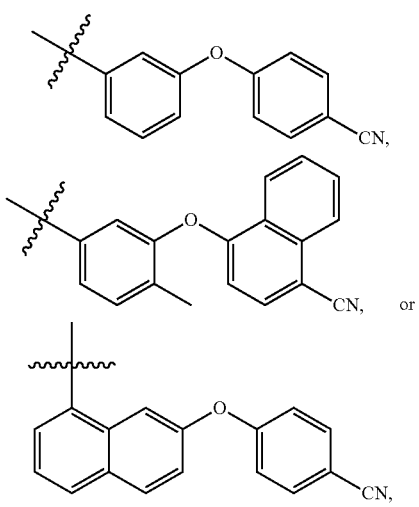
for example. The substituted phenyl group may be
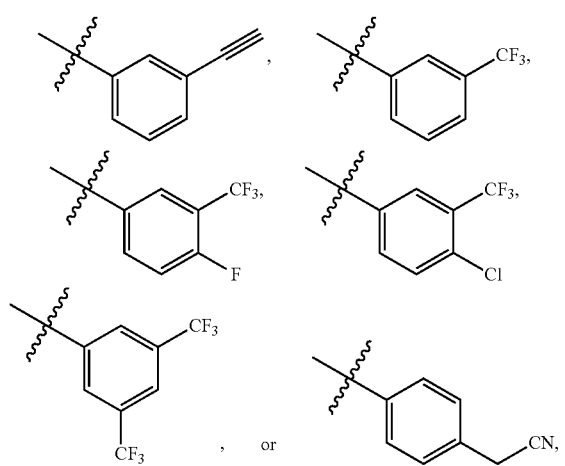
for example. The substituted
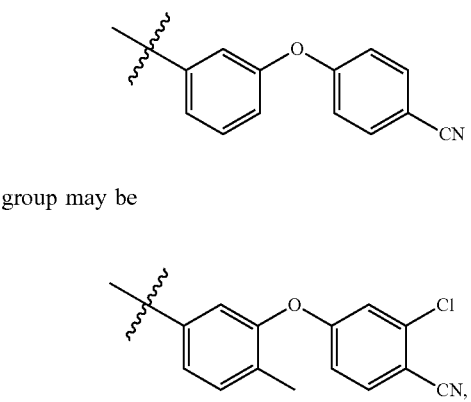
group may be
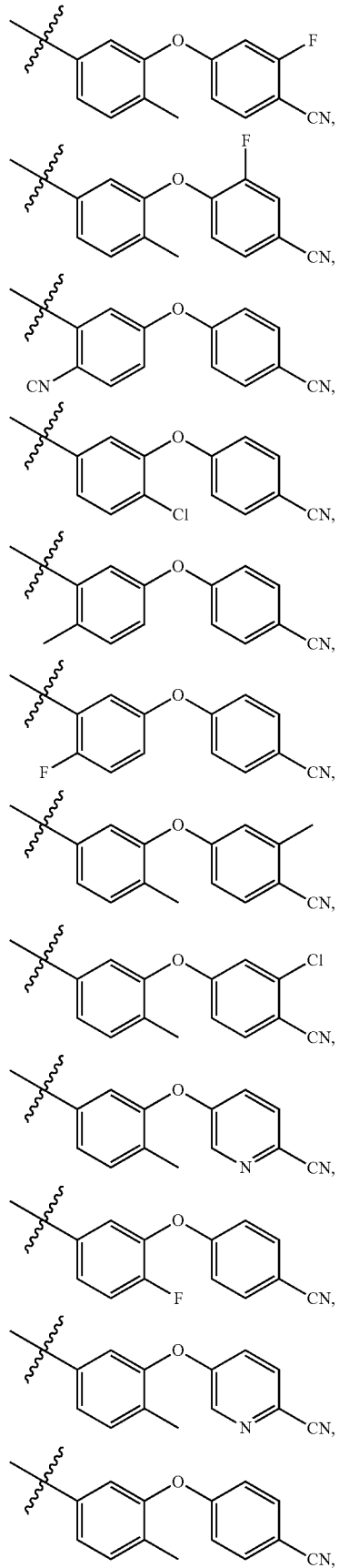

-continued

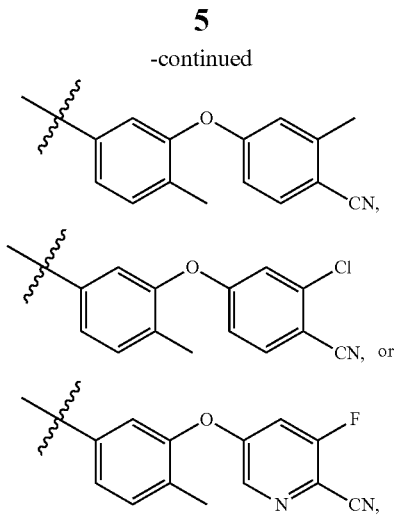

for example.

According to another embodiment of this disclosure, a compound II having a chemical structure shown below is provided.

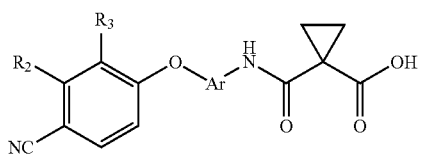

In the chemical structure of compound II, $R_2$ and $R_3$ are H.

Ar is a substituted aromatic group, such as

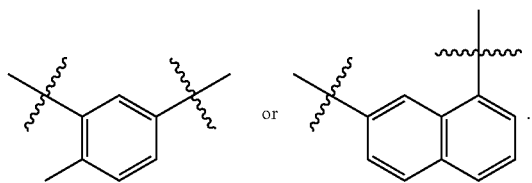

According to another embodiment of this disclosure, a compound III having a chemical structure shown below is provided.

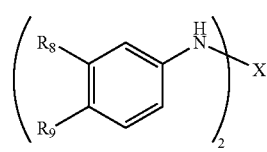

In the chemical structure of compound III, $R_8$ is a halo alkyl group or a substituted phenoxyl group ($C_6H_5O$—). The haloalkyl group is $CF_3$, for example. The substituted phenoxyl group is

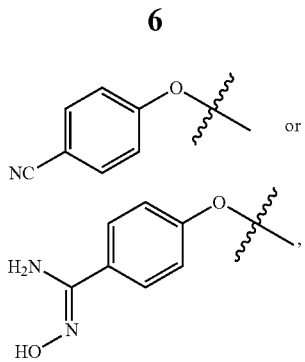

for example.

$R_9$ is H, a halide, or an alkyl group. The halide is Cl, for example. The alkyl group is $CH_3$ or $CH_2CH_3$, for example.

X is

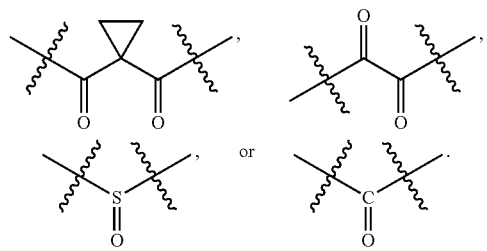

According to another embodiment of this disclosure, a compound IV having a chemical structure shown below is provided.

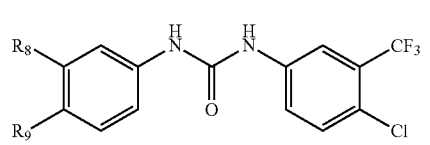

In the chemical structure of compound IV, $R_8$ is a substituted phenoxyl group ($C_6H_5O$—), such as

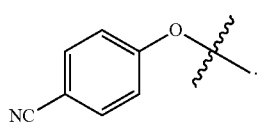 [SMILES: *Oc1ccc(C#N)cc1]

$R_9$ is H.

In addition, a pharmaceutical composition comprising an effective amount of any one compounds described above is provided, too.

According to an embodiment of this invention, the pharmaceutical composition may further comprises a pharmaceutically acceptable carrier.

It is to be understood that both the foregoing general description and the following detailed description are by examples, and are intended to provide further explanation of the invention as claimed.

DETAILED DESCRIPTION

According to this disclosure, the newly designed compounds act as SHP-1 agonists are useful for treating a disease or condition characterized by decreased expression levels or biological activity of SHP-1, such as cancer (e.g. hepatocellular carcinoma, hepatocellular carcinoma, leukemia, lung cancer, breast cancer, renal cancer, thyroid cancer, head and neck cancer, sclerosis and osteoporosis). These compounds also provide a new therapeutic option for patients with the resistance to kinase inhibitors. These tumors generate kinase mutation after treatment and constitutively in the phosphorylated active form, even in the present of a kinase inhibitor.

Therefore, upregulation of a tumor suppressor, especially the activity and the level of SHP-1, to repress the active mutation form of kinases is a promising direction for chemoresistance patients. In other words, the compounds of this disclosure, acting through a new targeting mechanism (kinase independent), provide alternative therapeutic options that may be helpful in the treatment of cancer with resistance to conventional medical therapeutics.

General Chemical Structure

According to an embodiment of this disclosure, a compound I having a chemical structure shown below is provided.

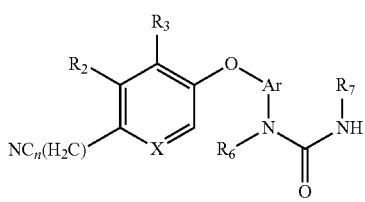

I

X is N or C—$R_1$

In the chemical structure of compound I,
n is 0 or 1.
X is N or C—$R_1$.
$R_1$ is H or Cl.
$R_2$ is H, a halide or an alkyl group. The halide is F, Cl, or Br, for example. The alkyl group is $CH_3$ or $CH_2CH_3$, for example.
$R_3$ is H, a halide or an alkyl group. The halide is F, Cl, or Br, for example. The alkyl group is $CH_3$ or $CH_2CH_3$, for example.
$R_2$ and $R_3$ also can together form a bivalent saturated or unsaturated group, such as

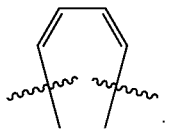 [SMILES: */C=C\C=C/*]

Ar is an unsubstituted or substituted phenylene group or a naphthalenylene group. The phenylene group may be

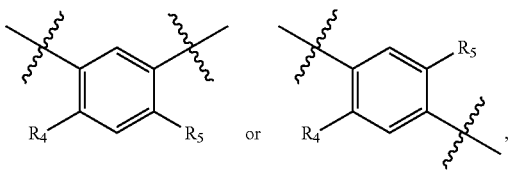

for example. The naphthalenylene group may be

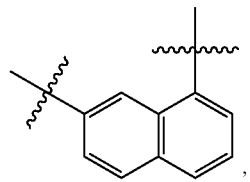 [SMILES: *c1ccc2cccc(*)c2c1]

for example.

$R_4$ is H, a halide or an alkyl group. The halide is F or Cl, for example. The alkyl group is $CH_3$ or $CH_2CH_3$, for example.

$R_5$ is H, a halide, an alkyl group, an alkoxyl group or a hydroxyl group. The halide is F or Cl, for example. The alkyl group is $CH_3$ or $CH_2CH_3$, for example.

$R_6$ is H or a hydroxyl group. $R_5$ and $R_6$ also can together form a bivalent saturated or unsaturated group, such as

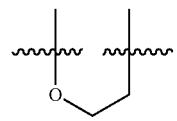

$R_7$ is an unsubstituted or substituted aromatic group. $R_7$ is a substituted phenyl group, a substituted

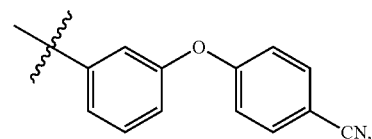

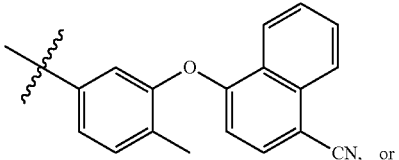

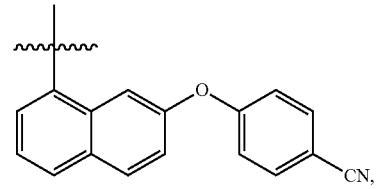

for example. The substituted phenyl group may be

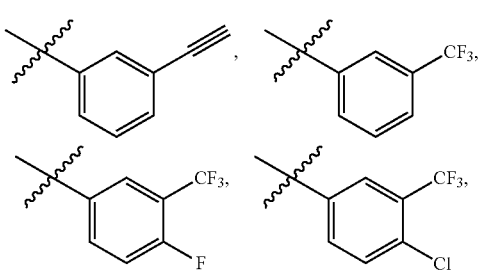

-continued
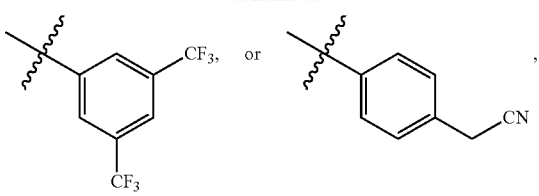
for example. The substituted
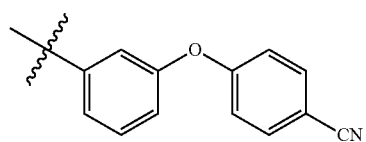 [SMILES: *c1cccc(Oc2ccc(C#N)cc2)c1]
group may be
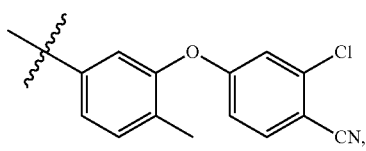
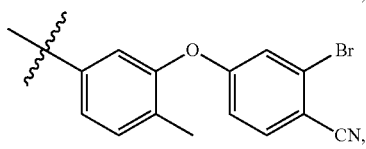
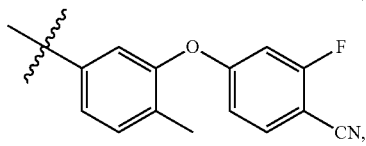
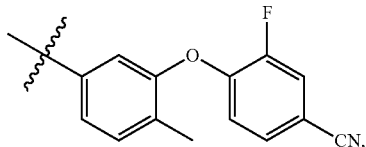
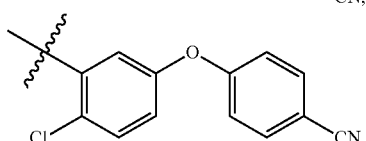
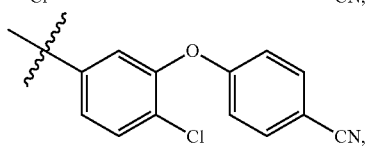
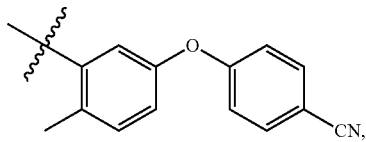
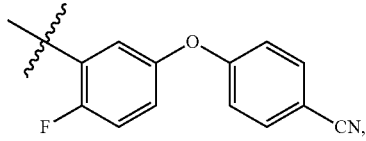
-continued
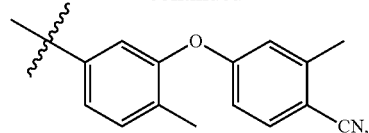
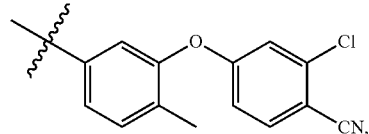
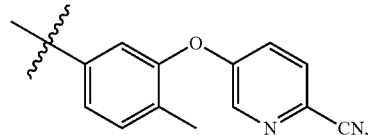
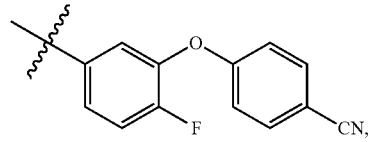
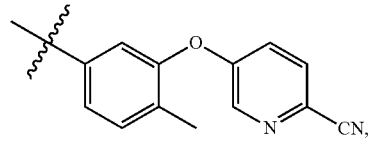
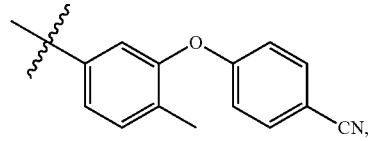
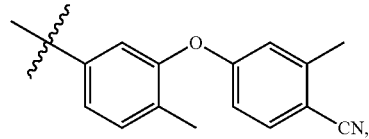
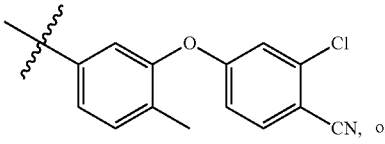
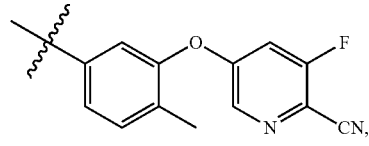
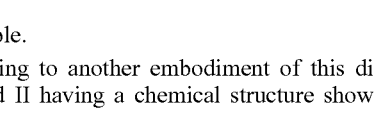
for example.
According to another embodiment of this disclosure, a compound II having a chemical structure shown below is provided.
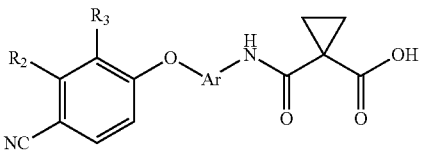
In the chemical structure of compound II,
$R_2$ and $R_3$ are H.

Ar is a substituted aromatic group, such as

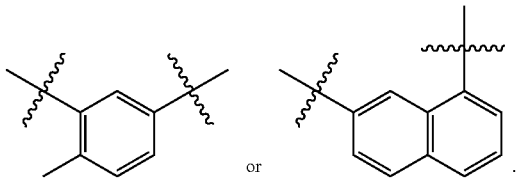

or

According to another embodiment of this disclosure, a compound III having a chemical structure shown below is provided.

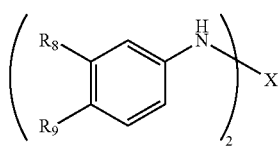

III

In the chemical structure of compound III, $R_8$ is a halo alkyl group or a substituted phenoxyl group ($C_6H_5O$—). The haloalkyl group is $CF_3$, for example. The substituted phenoxyl group is

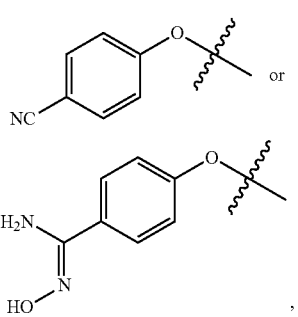

for example.

$R_9$ is H, a halide, or an alkyl group. The halide is Cl, for example. The alkyl group is $CH_3$ or $CH_2CH_3$, for example.

X is

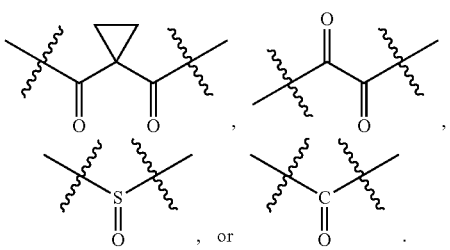

According to another embodiment of this disclosure, a compound IV having a chemical structure shown below is provided.

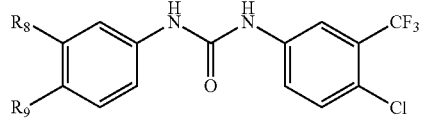

IV

In the chemical structure of compound IV, $R_8$ is a substituted phenoxyl group ($C_6H_5O$—), such as

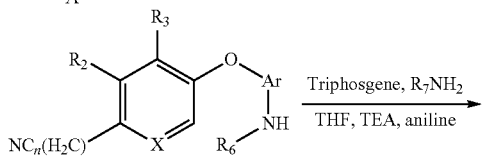

$R_9$ is H.

Chemical Synthesis

Synthesis Scheme I

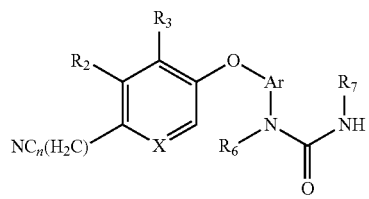

I

In the first step of synthesis scheme I, compound A was coupled with compound B to generate intermediate C in the present of t-BuOK. In this step, t-BuOK was first added to a DMSO solution of the compound B at 4° C. Next, compound A was added to the reaction mixture. The obtained reaction mixture was then stirred at room temperature for 5 minutes and heated to 150° C. for 20 minutes by microwave afterwards. After the reaction mixture was cooled to room temperature, ice water was added thereto to quench the reaction. The reaction mixture was extracted with ethyl acetate (3×100 mL). The collected organic phases were washed with brine, dried over anhydrous $MgSO_4$ and finally filtered. The filtrate was concentrated and then purified with chromatography to obtain intermediate C.

In step 2, the intermediate C and the amine $R_7NH_2$ were reacted with triphosgene to obtain the final compound I. In this step, a dried THF solution of amine R and triethylamine was slowly added to a dried THF solution of triphosgene in an ice-bath. The mixture was stirred at 60° C. for 30 minutes under a nitrogen atmosphere. After the temperature was cooled to room temperature, in a dried THF solution of the intermediate C was slowly added to the mixture in an ice-bath and heated at 60° C. overnight. The resulting solution was filtered to get rid of the salt and the filtrate was concentrated for chromatography. After purified with chromatography, compound I was obtained.

In the synthesis scheme I:

n is 0 or 1.

X is N or C—$R_1$.

$R_1$ is H, or Cl.

$R_2$ is H, a halide or an alkyl group. The halide is F, Cl, or Br, for example. The alkyl group is $CH_3$ or $CH_2CH_3$, for example.

$R_3$ is H, a halide or an alkyl group. The halide is F, Cl, or Br, for example. The alkyl group is $CH_3$ or $CH_2CH_3$, for example.

$R_2$ and $R_3$ also can together form a bivalent saturated or unsaturated group, such as

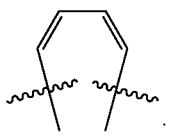 [SMILES: */C=C\C=C/*]

Ar is an unsubstituted or substituted phenylene group or a naphthalenylene group. The phenylene group may be

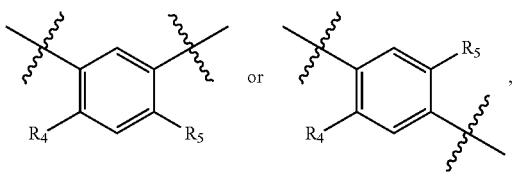

for example. The naphthalenylene group may be

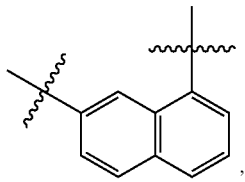 [SMILES: *c1ccc2cccc(*)c2c1]

for example.

$R_4$ is H, a halide or an alkyl group. The halide is F or Cl, for example. The alkyl group is $CH_3$ or $CH_2CH_3$, for example.

$R_5$ is H, a halide, an alkyl group, an alkoxyl group or a hydroxyl group. The halide is F or Cl, for example. The alkyl group is $CH_3$ or $CH_2CH_3$, for example.

$R_6$ is H or a hydroxyl group. $R_5$ and $R_6$ also can together form a bivalent saturated or unsaturated group, such as

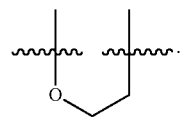

$R_7$ is an unsubstituted or substituted aromatic group. $R_7$ is a substituted phenyl group, a substituted

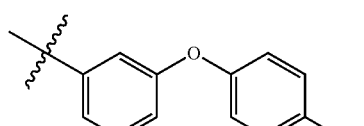

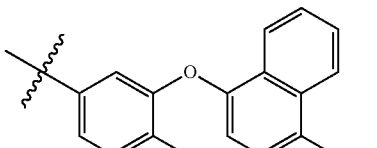

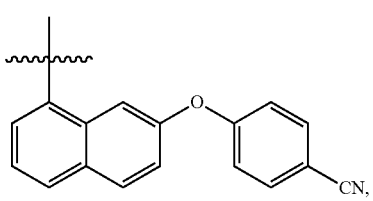

for example. The substituted phenyl group may be

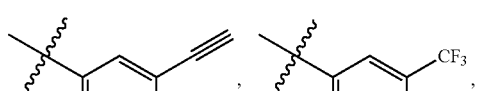

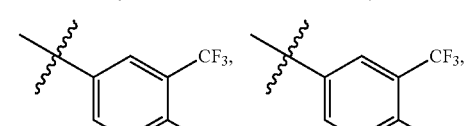

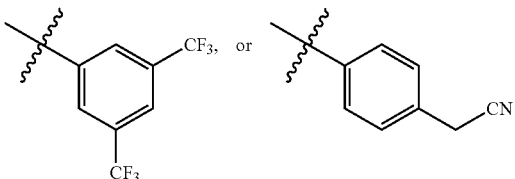

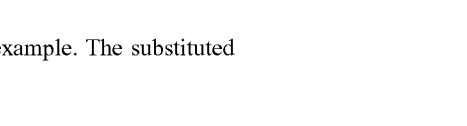

for example. The substituted

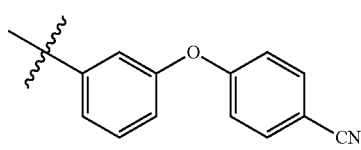 [SMILES: *c1cccc(Oc2ccc(C#N)cc2)c1]

group may be
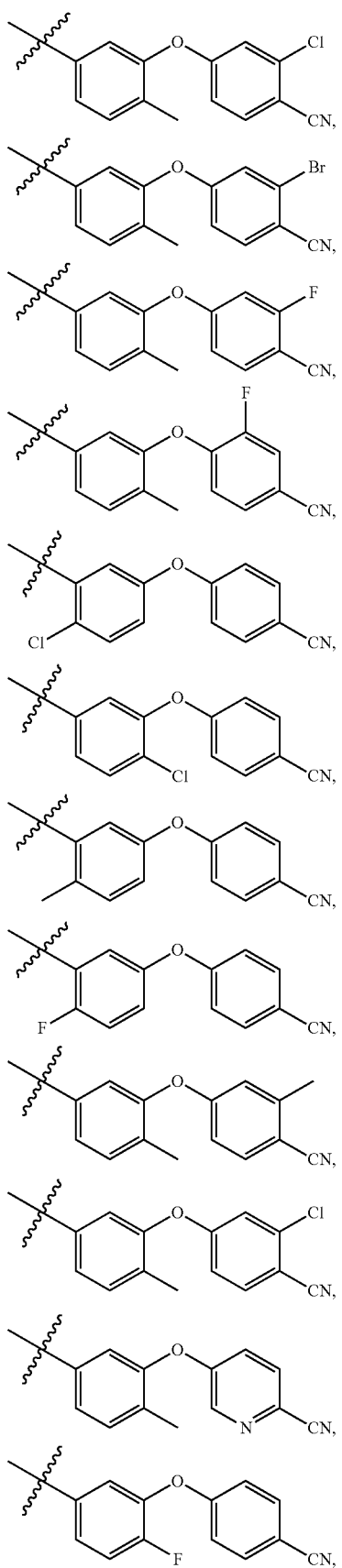
Embodiment 1: Ar is
in Synthesis Scheme I

In the synthesis scheme 1, n is 0.

X is N or C—R$_1$.

R$_1$ is H, or Cl.

R$_2$ is H, a halide or an alkyl group. The halide is F, Cl, or Br, for example. The alkyl group is CH$_3$ or CH$_2$CH$_3$, for example.

R$_3$ is H, a halide or an alkyl group. The halide is F, Cl, or Br, for example. The alkyl group is CH$_3$ or CH$_2$CH$_3$, for example.

R$_2$ and R$_3$ also can together form a bivalent saturated or unsaturated group, such as

R$_4$ is H, a halide or an alkyl group. The halide is F or Cl, for example. The alkyl group is CH$_3$ or CH$_2$CH$_3$, for example.

R$_5$ is H, a halide, an alkyl group, an alkoxyl group or a hydroxyl group. The halide is F or Cl, for example. The alkyl group is CH$_3$ or CH$_2$CH$_3$, for example.

R$_6$ is H or a hydroxyl group.

R$_5$ and R$_6$ also can together form a bivalent saturated or unsaturated group, such as

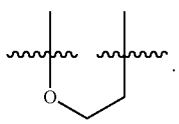 [SMILES: *CCO*]

R$_7$ is an unsubstituted or substituted aromatic group. For example, R$_7$ is a substituted phenyl group, or a substituted

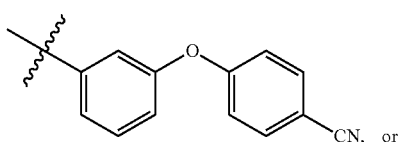

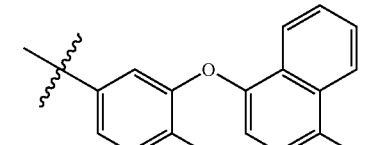

The substituted phenyl group may be

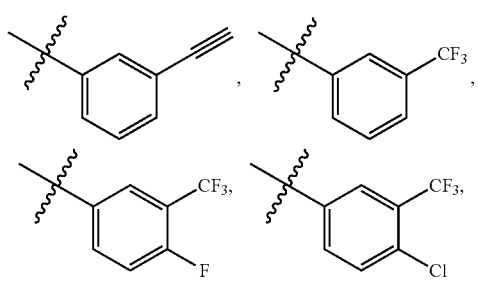

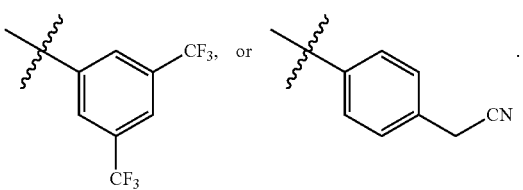

The substituted

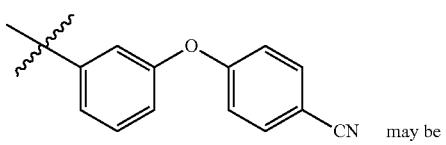 may be

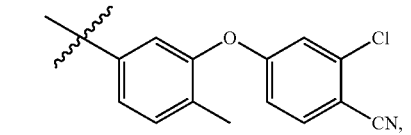

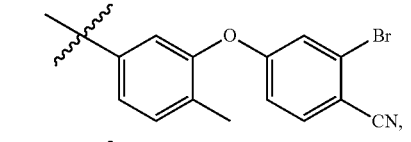

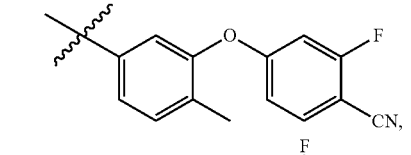

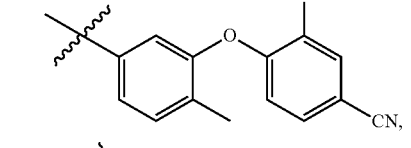

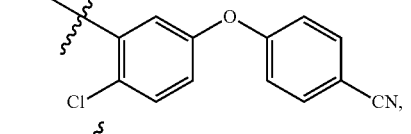

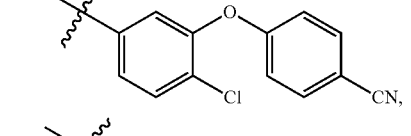

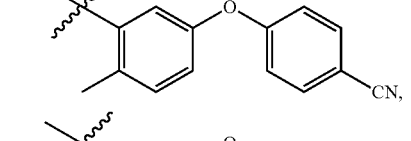

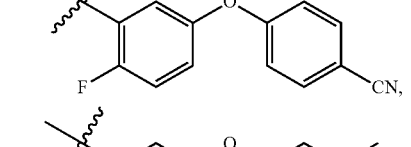

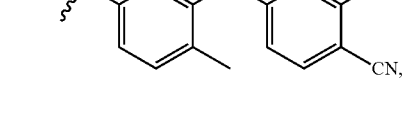

-continued
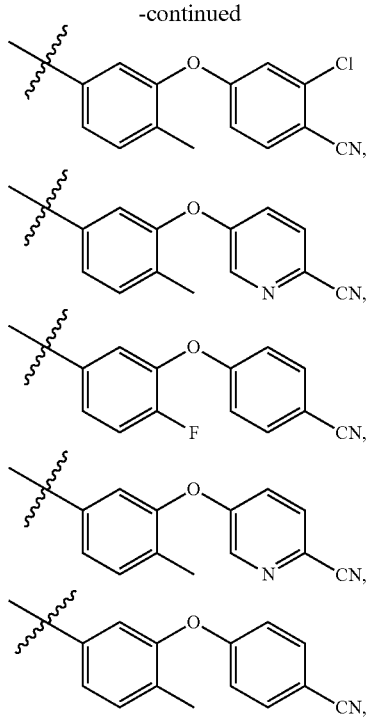
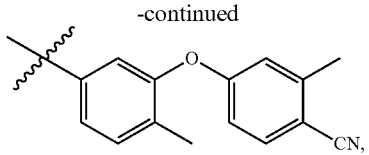
-continued
for example.
The examples of the synthetic compounds for synthesis scheme 1 are listed in Table 1 below.
TABLE 1
| synthetic compounds for synthesis scheme 1 | | | | | | | | |
|---|---|---|---|---|---|---|---|---|
| SC | n | X | $R_1$ | $R_2$ | $R_3$ | $R_4$ | $R_5$ | $R_6$ | $R_7$ |
| 65 | 0 | C | H | H | H | H | H | H | 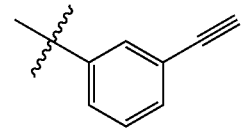 [SMILES: *c1cccc(C#C)c1] |
| 66 | 0 | C | H | H | H | $CH_3$ | H | H | 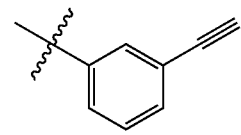 [SMILES: *c1cccc(C#C)c1] |
| 140 | 0 | C | H | H | H | Cl | H | H | 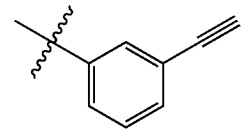 [SMILES: *c1cccc(C#C)c1] |
| 144 | 0 | C | H | H | H | H | F | H | 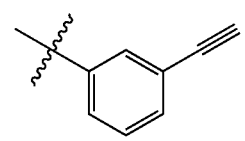 [SMILES: *c1cccc(C#C)c1] |
| 150 | 0 | C | H | H | H | F | H | H | 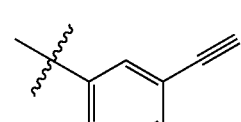 |

TABLE 1-continued
synthetic compounds for synthesis scheme 1
| SC | n | X | R$_1$ | R$_2$ | R$_3$ | R$_4$ | R$_5$ | R$_6$ | R$_7$ |
|---|---|---|---|---|---|---|---|---|---|
| 134 | 0 | C | H | H | H | CH$_3$ | H | H | 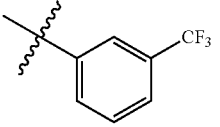 [SMILES: *c1cccc(C(F)(F)F)c1] |
| 138 | 0 | C | H | H | H | Cl | H | H | 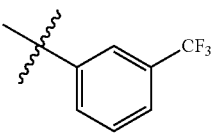 [SMILES: *c1cccc(C(F)(F)F)c1] |
| 151 | 0 | C | H | H | H | F | H | H | 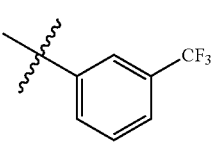 [SMILES: *c1cccc(C(F)(F)F)c1] |
| 174 | 0 | C | H | CH$_3$ | H | Cl | H | H | 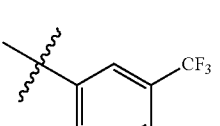 |
| 178 | 0 | C | H | Cl | H | Cl | H | H | 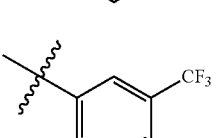 |
| 132 | 0 | C | H | H | H | CH$_3$ | H | H | 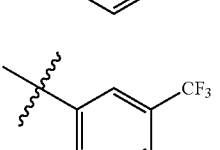 |
| 137 | 0 | C | H | H | H | Cl | H | H | 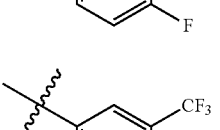 |
| 143 | 0 | C | H | H | H | H | Cl | H | 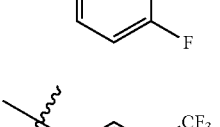 |
| 145 | 0 | C | H | H | H | H | F | H | 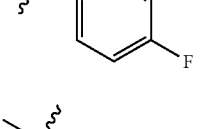 |
| 154 | 0 | C | H | H | H | F | H | H | 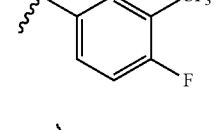 |

TABLE 1-continued
synthetic compounds for synthesis scheme 1
| SC | n | X | R$_1$ | R$_2$ | R$_3$ | R$_4$ | R$_5$ | R$_6$ | R$_7$ |
|---|---|---|---|---|---|---|---|---|---|
| 177 | 0 | C | H | CH$_3$ | H | Cl | H | H | 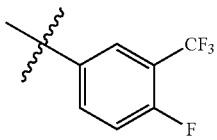 [SMILES: *c1ccc(F)c(C(F)(F)F)c1] |
| 181 | 0 | C | H | Cl | H | Cl | H | H | 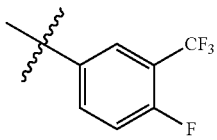 [SMILES: *c1ccc(F)c(C(F)(F)F)c1] |
| 79 | 0 | C | H | Cl | H | H | H | H | 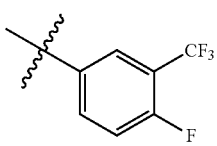 [SMILES: *c1ccc(F)c(C(F)(F)F)c1] |
| 80 | 0 | C | H | H | F | H | H | H | 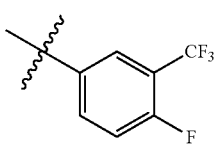 [SMILES: *c1ccc(F)c(C(F)(F)F)c1] |
| 88 | 0 | C | H | F | H | CH$_3$ | H | H | 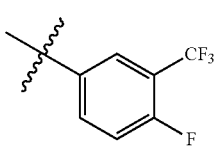 [SMILES: *c1ccc(F)c(C(F)(F)F)c1] |
| 89 | 0 | C | H | Br | H | CH$_3$ | H | H | 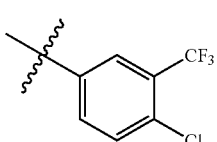 |
| 105 | 0 | C | H | H | H | H | F | H | 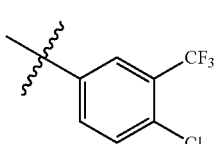 |
| 111 | 0 | C | H | H | H | F | H | H | 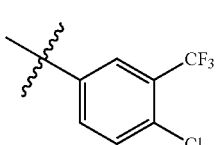 |
| 133 | 0 | C | H | H | H | CH$_3$ | H | H | 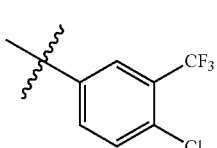 |
| 139 | 0 | C | H | H | H | Cl | H | H | 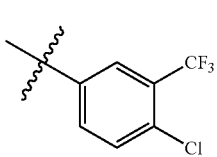 |

TABLE 1-continued
synthetic compounds for synthesis scheme 1
| SC | n | X | $R_1$ | $R_2$ | $R_3$ | $R_4$ | $R_5$ | $R_6$ | $R_7$ |
|---|---|---|---|---|---|---|---|---|---|
| 142 | 0 | C | H | H | H | H | Cl | H | 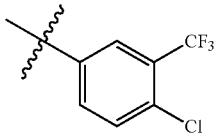 [SMILES: *c1ccc(Cl)c(C(F)(F)F)c1] |
| 175 | 0 | C | H | $CH_3$ | H | Cl | H | H | 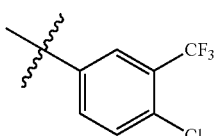 |
| 179 | 0 | C | H | Cl | H | Cl | H | H | 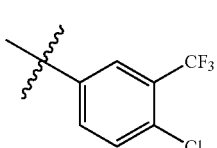 |
| 87 | 0 | N | — | H | H | $CH_3$ | H | H | 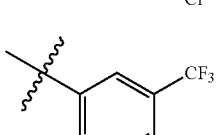 |
| 114 | 0 | C | H | 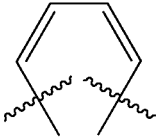 [SMILES: */C=C\C=C/*] | | $CH_3$ | H | H | 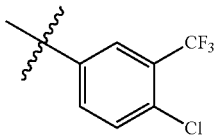 [SMILES: *c1ccc(Cl)c(C(F)(F)F)c1] |
| 131 | 0 | C | H | H | H | $CH_3$ | H | H | 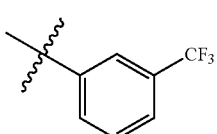 |
| 141 | 0 | C | H | H | H | H | H | H | 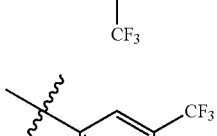 |
| 148 | 0 | C | H | H | H | Cl | H | H | 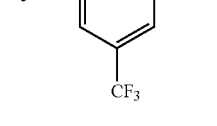 |
| 152 | 0 | C | H | H | H | F | H | H | 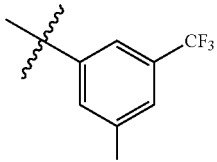 |

TABLE 1-continued
synthetic compounds for synthesis scheme 1
| SC | n | X | R$_1$ | R$_2$ | R$_3$ | R$_4$ | R$_5$ | R$_6$ | R$_7$ |
|---|---|---|---|---|---|---|---|---|---|
| 176 | 0 | C | H | CH$_3$ | H | Cl | H | H | 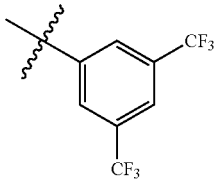 [SMILES: *c1cc(C(F)(F)F)cc(C(F)(F)F)c1] |
| 180 | 0 | C | H | Cl | H | Cl | H | H | 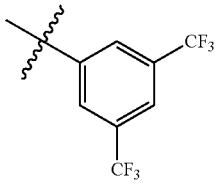 [SMILES: *c1cc(C(F)(F)F)cc(C(F)(F)F)c1] |
| 182 | 0 | N | — | H | H | Cl | H | H | 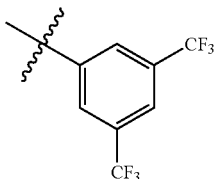 |
| 183 | 0 | N | — | H | H | H | F | H | 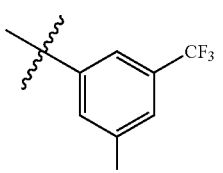 |
| 135 | 0 | C | H | H | H | CH$_3$ | H | H | 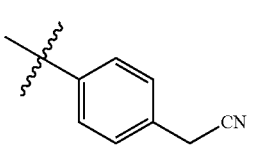 [SMILES: *c1ccc(CC#N)cc1] |
| 146 | 0 | C | H | H | H | H | F | H | 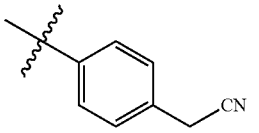 |
| 149 | 0 | C | H | H | H | Cl | H | H | 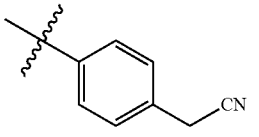 [SMILES: *c1ccc(CC#N)cc1] |
| 153 | 0 | C | H | H | H | F | H | H | 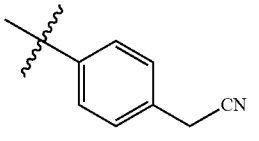 [SMILES: *c1ccc(CC#N)cc1] |
| 82 | 0 | C | H | Cl | H | CH$_3$ | H | H | 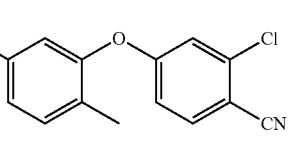 |

TABLE 1-continued synthetic compounds for synthesis scheme 1

| SC | n | X | $R_1$ | $R_2$ | $R_3$ | $R_4$ | $R_5$ | $R_6$ | $R_7$ |
|---|---|---|---|---|---|---|---|---|---|
| 83 | 0 | C | H | Br | H | $CH_3$ | H | H | 2-methyl-4-(4-cyano-3-bromophenoxy)phenyl |
| 84 | 0 | C | H | F | H | $CH_3$ | H | H | 2-methyl-4-(4-cyano-3-fluorophenoxy)phenyl |
| 85 | 0 | C | H | H | F | $CH_3$ | H | H | 2-methyl-4-(4-cyano-2-fluorophenoxy)phenyl |
| 91 | 0 | C | H | H | H | H | Cl | H | 2-chloro-5-(4-cyanophenoxy)phenyl |
| 92 | 0 | C | H | H | H | Cl | H | H | 2-chloro-4-(4-cyanophenoxy)phenyl |
| 93 | 0 | C | H | H | H | H | $CH_3$ | H | 2-methyl-5-(4-cyanophenoxy)phenyl |
| 97 | 0 | C | H | H | H | H | H | F | 2-fluoro-5-(4-cyanophenoxy)phenyl |
| 98 | 0 | C | H | $CH_3$ | H | $CH_3$ | H | H | 2-methyl-4-(4-cyano-3-methylphenoxy)phenyl |
| 100 | 0 | C | H | H | H | $CH_3$ | H | H | 2-methyl-4-(4-cyano-3-chlorophenoxy)phenyl |
| 110 | 0 | C | H | H | H | H | F | H | 2-methyl-5-(6-cyanopyridin-3-yloxy)phenyl |

TABLE 1-continued synthetic compounds for synthesis scheme 1

| SC | n | X | R$_1$ | R$_2$ | R$_3$ | R$_4$ | R$_5$ | R$_6$ | R$_7$ |
|---|---|---|---|---|---|---|---|---|---|
| 112 | 0 | C | H | H | H | F | H | H | 4-cyanophenoxy-2-fluorophenyl |
| 86 | 0 | N | — | H | H | CH$_3$ | H | H | (6-cyanopyridin-3-yl)oxy-methylphenyl |
| 99 | 0 | N | — | H | H | CH$_3$ | H | H | (4-cyanophenoxy)-methylphenyl |
| 102 | 0 | N | — | H | H | CH$_3$ | H | H | (4-cyano-3-methylphenoxy)-methylphenyl |
| 103 | 0 | N | — | H | H | CH$_3$ | H | H | (3-chloro-4-cyanophenoxy)-methylphenyl |
| 104 | 0 | N | — | F | H | CH$_3$ | H | H | (6-cyano-5-fluoropyridin-3-yl)oxy-methylphenyl |
| 113 | 0 | C | H | fused benzene | | CH$_3$ | H | H | (4-cyanonaphthalen-1-yl)oxy-methylphenyl |
| 156 | 0 | C | H | H | H | H | —O-CH$_2$-CH(ring)— | | 4-fluoro-3-(trifluoromethyl)phenyl |
| 157 | 0 | C | H | H | H | H | —O-CH$_2$-CH(ring)— | | 4-chloro-3-(trifluoromethyl)phenyl |

TABLE 1-continued synthetic compounds for synthesis scheme 1

| SC | n | X | R₁ | R₂ | R₃ | R₄ | R₅ | R₆ | R₇ |
|---|---|---|---|---|---|---|---|---|---|
| 158 | 0 | C | H | H | H | H | (–O–CH₂ linker) | | 3,5-bis(CF₃)phenyl |
| 159 | 0 | C | H | H | H | H | (–O–CH₂ linker) | | 3-CF₃-phenyl |
| 160 | 0 | C | H | H | H | H | (–O–CH₂ linker) | | 4-(CH₂CN)phenyl |
| 161 | 0 | C | H | H | H | H | (–O–CH₂ linker) | | 3-ethynylphenyl |

Synthetic Method of SC-92 (Example of Synthetic Scheme 1)

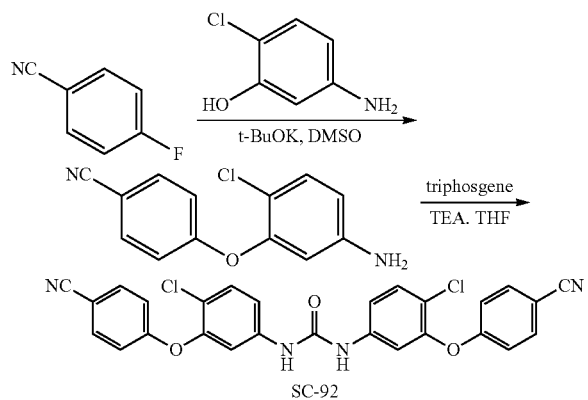

In the synthesis of compound SC-92, 4-fluorobenzonitrile was first coupled with 5-amino-2-chlorophenol and then reacted with triphosgene to obtain compound SC-92.

In the first step, intermediate 4-(5-amino-2-chlorophenoxy)benzonitrile was synthesized. To the DMSO (1 mL) solution of 5-amino-2-chlorophenol (0.25 g, 1.75 mmol), t-BuOK (0.245 g, 2.19 mmol) was added at ice-bath. 4-fluorobenzonitrile (0.176, 1.45 mmol) were added to the solution and stirred at room temperature for 5 minutes and then heated to 150° C. for 20 minutes by microwave machine. Ice water was added, and the suspension was extracted with Ethyl acetate (3×100 mL). The collected organic phases were washed with brine, dried over MgSO₄ and filtered. The filtrate was concentrated and then purified with chromatography to obtain the intermediate of 4-(5-amino-2-chlorophenoxy)benzonitrile.

4-(5-amino-2-chlorophenoxy)benzonitrile: ¹H NMR (400 MHz, MeOD): δ 7.68 (d, J=8.8 Hz, 2H), 7.18 (d, J=8.8 Hz, 1H), 6.99 (d, J=8.8 Hz, 2H), 6.58 (dd, J=8.4 Hz, 2.8 Hz, 1H), 6.49 (d, J=2.8 Hz, 1H).

In the second step, the product 1,3-bis(4-chloro-3-(4-cyanophenoxy) phenyl)urea (SC-92) was synthesized. First, 4-(5-amino-2-chlorophenoxy) benzonitrile (0.148 g, 0.61 mmol) with triethylamine (0.153 mL, 1.1 mmol) in dried THF (3 mL) were added slowly to the dried THF (3 mL) solution of triphosgene (0.082 g, 0.28 mmol) in ice-bathed. The mixture was stirred at 60° C. overnight under a nitrogen atmosphere. After cooling the temperature to room temperature, the resulting solution was filtered to get rid of the salt and concentrated the filtrate. The concentrated filtrate then washed with hexane (3×5 mL) and collected the resultant precipitate to dry under reduced pressure to obtain 1,3-bis (4-chloro-3-(4-cyanophenoxy) phenyl)urea.

Embodiment 2: Ar is

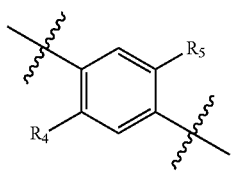

in Synthesis Scheme I

Synthesis Scheme 2

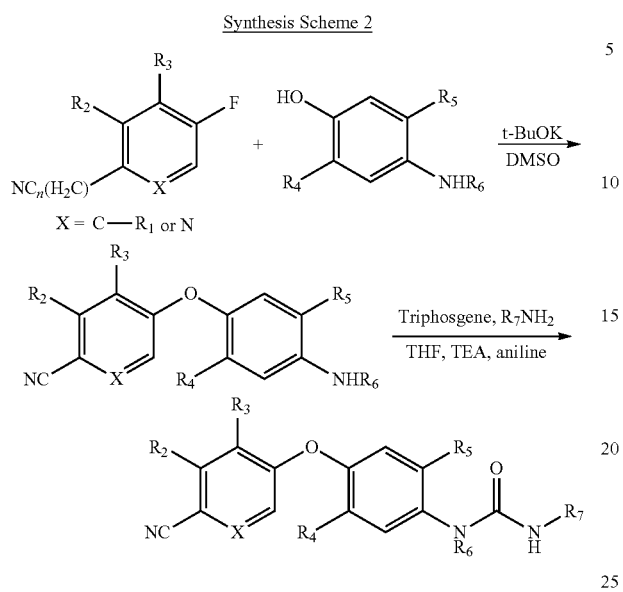

n is 0 or 1.
X is N or C—$R_1$.
$R_1$ is H, or Cl.
$R_2$ is H, a halide or an alkyl group. The halide is F, Cl, or Br, for example. The alkyl group is $CH_3$ or $CH_2CH_3$, for example.
$R_3$ is H, a halide or an alkyl group. The halide is F, Cl, or Br, for example. The alkyl group is $CH_3$ or $CH_2CH_3$, for example.
$R_4$ is H, a halide or an alkyl group. The halide is F or Cl, for example.
The alkyl group is $CH_3$ or $CH_2CH_3$, for example.
$R_5$ is H, a halide, an alkyl group, an alkoxyl group or a hydroxyl group. The halide is F or Cl, for example. The alkyl group is $CH_3$ or $CH_2CH_3$, for example.
$R_6$ is H or a hydroxyl group.
$R_5$ and $R_6$ also can together form a bivalent saturated or unsaturated group, such as

.

$R_7$ is an unsubstituted or substituted aromatic group. For example, $R_7$ is a substituted phenyl group, or a substituted

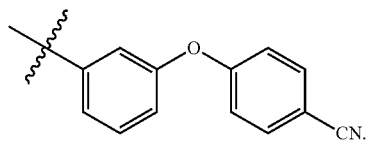 [SMILES: *c1cccc(Oc2ccc(C#N)cc2)c1]

The substituted phenyl group may be

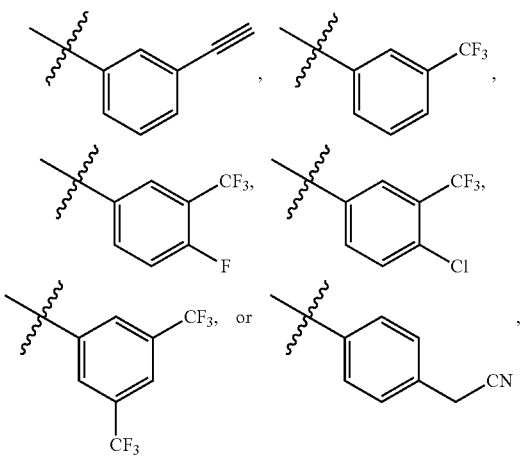

for example. The substituted

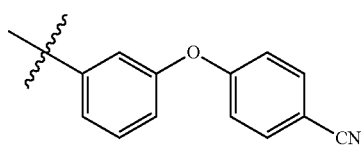 [SMILES: *c1cccc(Oc2ccc(C#N)cc2)c1]

may be

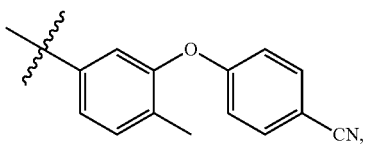 [SMILES: *c1ccc(C)c(Oc2ccc(C#N)cc2)c1]

for example.

The examples of the synthetic compounds for synthesis scheme 2 are listed in Table 2 below.

TABLE 2

| | | | | | | | | | |
|---|---|---|---|---|---|---|---|---|---|
| synthetic compounds for synthesis scheme 2 ||||||||||
| SC | n | X | $R_1$ | $R_2$ | $R_3$ | $R_4$ | $R_5$ | $R_6$ | $R_7$ |
| 96 | 0 | C | H | H | H | H | F | H | 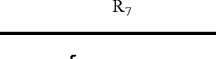 |

TABLE 2-continued synthetic compounds for synthesis scheme 2

| SC | n | X | R₁ | R₂ | R₃ | R₄ | R₅ | R₆ | R₇ |
|---|---|---|---|---|---|---|---|---|---|
| 108 | 0 | C | H | Cl | H | H | F | H | 3-CF₃-4-Cl-phenyl |
| 90 | 0 | C | H | H | H | H | CH₃ | H | 2-methyl-4-(4-cyanophenoxy)phenyl |
| 106 | 0 | C | H | H | H | H | F | H | 2-fluoro-4-(4-cyanophenoxy)phenyl |
| 168 | 1 | C | H | H | H | H | H | H | 3-CF₃-4-F-phenyl |
| 169 | 1 | C | H | H | H | H | H | H | 4-(cyanomethyl)phenyl |
| 170 | 1 | C | H | H | H | H | H | H | 3-ethynylphenyl |
| 171 | 1 | C | H | H | H | H | H | H | 3-CF₃-4-Cl-phenyl |
| 172 | 1 | C | H | H | H | H | H | H | 3,5-bis(CF₃)phenyl |
| 173 | 1 | C | H | H | H | H | H | H | 3-CF₃-phenyl |
| 162 | 0 | C | H | H | H | H | -OCH₂- (bridge) | | 3-ethynylphenyl |

TABLE 2-continued
synthetic compounds for synthesis scheme 2
| SC | n | X | R₁ | R₂ | R₃ | R₄ | R₅ R₆ | R₇ |
|---|---|---|---|---|---|---|---|---|
| 163 | 0 | C | H | H | H | H | -O-CH₂- linker | 3-CF₃-phenyl |
| 164 | 0 | C | H | H | H | H | -O-CH₂- linker | 3,5-bis(CF₃)-phenyl |
| 165 | 0 | C | H | H | H | H | -O-CH₂- linker | 3-CF₃-4-Cl-phenyl |
| 166 | 0 | C | H | H | H | H | -O-CH₂- linker | 3-CF₃-4-F-phenyl |
| 167 | 0 | C | H | H | H | H | -O-CH₂- linker | 4-(CH₂CN)-phenyl |
Embodiment 3: Ar is
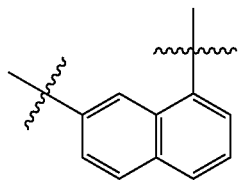 [SMILES: *c1ccc2cccc(*)c2c1]
in Synthesis Scheme I
Synthesis Scheme 3
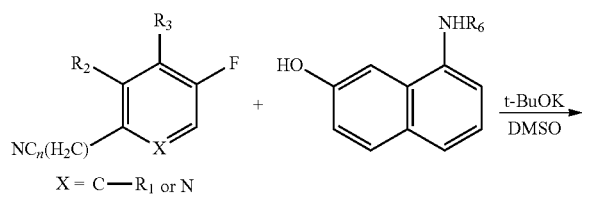
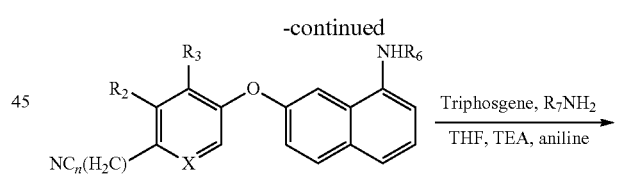
In synthesis scheme 3, n is 0.
X is C—R₁.
R₁ is H or Cl.
R₂, R₃, and R₆ are H.

$R_7$ is a substituted phenyl group, a substituted

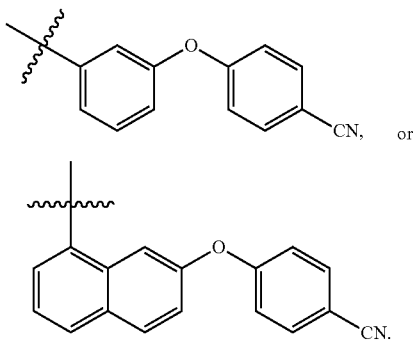

The substituted phenyl group is

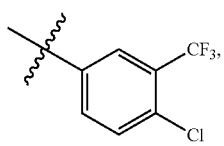 [SMILES: *c1ccc(Cl)c(C(F)(F)F)c1]

for example. The substituted

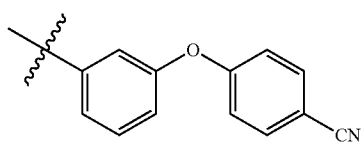 [SMILES: *c1cccc(Oc2ccc(C#N)cc2)c1]

is

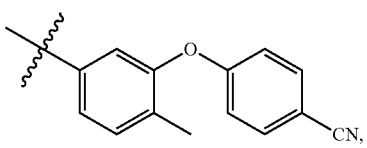 [SMILES: *c1ccc(C)c(Oc2ccc(C#N)cc2)c1]

for example.

The examples of the synthetic compounds for synthesis scheme 3 are listed in Table 3 below.

TABLE 3

| | | | synthetic compounds for synthesis scheme 3 | | | | |
|---|---|---|---|---|---|---|---|
| SC | n | X | $R_1$ | $R_2$ | $R_3$ | $R_6$ | $R_7$ |
| 72 | 0 | C | H | H | H | H | ![CF3/Cl phenyl] |
| 73 | 0 | C | H | H | H | H | ![naphthyl-O-phenyl-CN] |
| 107 | 0 | C | H | H | H | H | ![methylphenyl-O-phenyl-CN] |
| 109 | 0 | C | Cl | H | H | H | ![CF3/Cl phenyl] |

Synthetic Method of SC-72 (Example of Synthetic Scheme 3)

In the first step, 4-fluorobenzonitrile was coupled with 8-aminonaphthalen-2-ol to generate intermediate 4-((8-aminonaphthalen-2-yl)oxy)benzonitrile (chemical structure was shown below) in the present of t-BuOK.

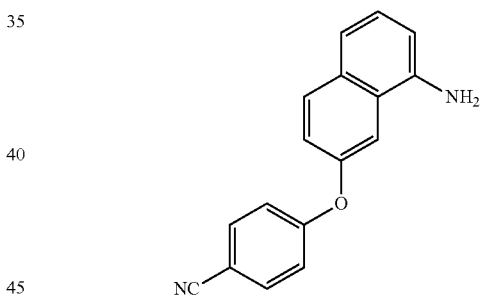

t-BuOK (0.42 g, 3.72 mmol) was added to 8-aminonaphthalen-2-ol (0.394 g, 2.48 mmol) in DMSO (1 mL) cooled to 4° C. 4-Fluorobenzonitrile (0.3 g, 2.48 mmol) was added to the reaction mixture and stirred at room temperature for 5 minutes and then heated to 150° C. for 20 minutes by microwave. After the reaction mixture was cooled to room temperature, the ice water was added to quench the reaction. The solution was extracted with Ethyl acetate (3×100 mL). The collected organic phases were washed with brine, dried over anhydrous MgSO4 and filtered. The filtrate was concentrated and then purified with chromatography to obtain intermediate 4-((8-aminonaphthalen-2-yl) oxy)benzonitrile.

4-((8-aminonaphthalen-2-yl)oxy)benzonitrile: $^1$H NMR (400 MHz, CDCl$_3$): δ 7.84 (d, J=8.8 Hz, 1H), 7.58 (d, J=8.8 Hz, 2H), 7.46 (d, J=2.4 Hz, 1H), 7.34-7.24 (m, 2H), 7.17 (dd, J=8.8 Hz, 2.4 Hz, 1H), 7.02 (d, J=8.8 Hz, 2H), 6.81 (dd, J=7.2 Hz, 1.2 Hz, 1H).

In the second step, the 4-((8-aminonaphthalen-2-yl)oxy) benzonitrile and 4-chloro-3-(trifluoromethyl) aniline reacted with triphosgene to obtain compound SC-72. 4-chloro-3-

(trifluoromethyl)aniline (0.18 g, 0.69 mmol) with triethylamine (0.38 mL, 2.76 mmol) in dried THF (3 mL) were added slowly to the dried THF (3 mL) solution of triphosgene (0.205 g, 0.69 mmol) at ice-bath. The mixture was stirred at 60° C. for 30 minutes under a nitrogen atmosphere. After the temperature was back to room temperature, 4-((8-aminonaphthalen-2-yl)oxy) benzonitrile (0.135 g, 0.69 mmol) in dried THF (3 mL) was added slowly to the mixture at ice-bath and heated at 60° C. overnight. The resulting solution was filtered to remove the salt and the filtrate was concentrated for chromatography. After purified with chromatography, 1-(4-chloro-3-(trifluoromethyl)phenyl)-3-(7-(4-cyanophenoxy) naphthalen-1-yl)urea (SC-72) was obtained.

Synthesis Scheme II

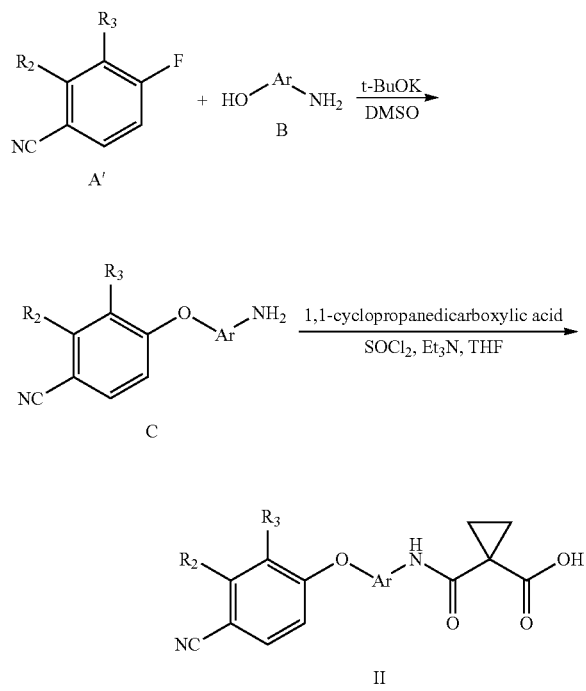

Embodiment 4: Synthesis Scheme II

The examples of the synthetic compounds for the synthesis scheme II are listed in Table 4 below.

TABLE 4

| | synthetic compounds for synthesis scheme II | | |
|---|---|---|---|
| SC | $R_2$ | $R_3$ | Ar |
| 68 | H | H | 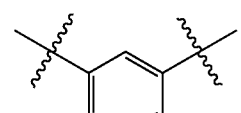 |
| 75 | H | H |  |

Synthesis Scheme III

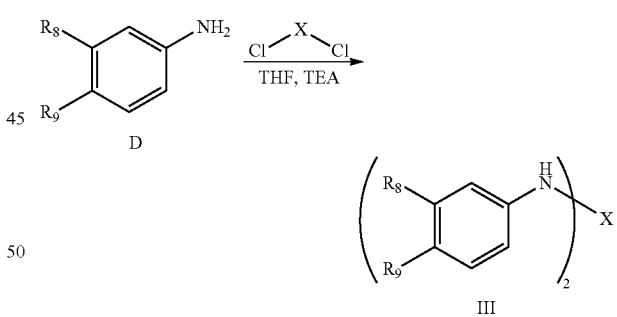

The first step of the synthesis scheme II was the same as the first step in the synthesis scheme I above, and the compound A in synthesis scheme I was simplified to compound A' in synthesis scheme II. Therefore, the detailed description of the first step in synthesis scheme II is omitted here.

In the second step, thionyl chloride was slowly added to 1 equivalent of 1,1-cyclopropanedicarboxylic acid in dichloromethane. The reaction mixture was stirred at 40° C. for 2 hr. After cooled down to room temperature, the reaction mixture was dried using rotary evaporator and then dissolved in dried THF. 2 equivalent of OH—Ar—$NH_2$ and 4 equivalent of triethylamine were added to the solution and then stirred at 40° C. for 8 hrs. The reaction mixture was extracted with ethyl acetate. The collected organic phases were washed with brine, dried over $MgSO_4$ and filtered. The filtrate was concentrated and then purified with chromatography to obtain the compound II.

In synthesis scheme II, Ar is a substituted aromatic group, such as

Compound D with triethylamine were added slowly to the dried THF solution of reagent $XCl_2$ (e.g., oxalyl chloride, thionyl chloride or triphosgene) at ice-bath. The mixture was stirred at 60° C. for 30 minutes under a nitrogen atmosphere. After the temperature was cooled to room temperature, the resulting solution was filtered to remove the salt, and the filtrate was then concentrated for chromatography. After purified with chromatography, compound III was obtained.

In the synthesis scheme III:

$R_8$ is a halo alkyl group or a substituted phenoxyl group ($C_6H_5O$—). The haloalkyl group is $CF_3$, for example. The substituted phenoxyl group is

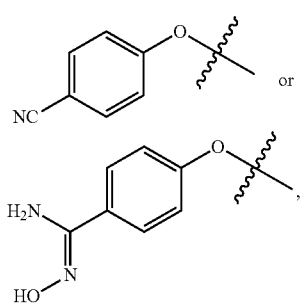

for example.

R$_9$ is H, a halide, or an alkyl group. The halide is Cl, for example. The alkyl group is CH$_3$.

X is

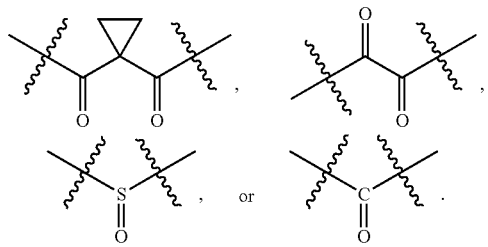

Embodiment 5: Synthesis Scheme III

The examples of the synthetic compounds for the synthesis scheme III are listed in Table 5 below.

TABLE 5 synthetic compounds for the synthesis scheme III

| SC | R$_8$ | R$_9$ | X |
|---|---|---|---|
| 67 | 4-NC-C$_6$H$_4$-O- | H | cyclopropane-1,1-diyl bis(carbonyl) |
| 70 | 4-NC-C$_6$H$_4$-O- | H | -C(O)-C(O)- |
| 71 | 4-NC-C$_6$H$_4$-O- | CH$_3$ | -C(O)-C(O)- |
| 76 | 4-NC-C$_6$H$_4$-O- | H | -S(O)- |
| 78 | CF$_3$ | Cl | -C(O)- |

TABLE 5-continued synthetic compounds for the synthesis scheme III

| SC | R$_8$ | R$_9$ | X |
|---|---|---|---|
| 94 | 4-(H$_2$N-C(=N-OH))-C$_6$H$_4$-O- | CH$_3$ | -C(O)- |

Synthetic Method of SC-94 (Example of Synthetic Scheme III)

2.2 equiv of 4-(5-amino-2-methylphenoxy)benzonitrile and 4 equiv of trimethylamine in dried THF was slowly added to dried THF solution of 1 equiv of triphosgene at ice bath. The reaction mixture was stirred at 60° C. for 8 hr. The resulting solution was filtered to get rid of the salt and concentrated the filtrate for chromatography to obtain 1,3-bis(3-(4-cyanophenoxy)-4-methylphenyl)urea.

2 equiv of hydroxylamine and 1.5 equiv of trimethylamine in dried THF was slowly added to ethanol solution of 1,3-bis(3-(4-cyanophenoxy)-4-methylphenyl)urea at ice bath. The mixture was stirred at 80° C. for 8 hr. After cooled down to room temperature, the resulting mixture was dried by rotary evaporator and then extracted with dichloromethane. The collected organic phases were washed with brine, dried over MgSO$_4$ and filtered. After recrystallization using dichloromethane and methanol, the precipitates were washed by dichloromethane to obtain SC-94.

Synthesis Scheme IV

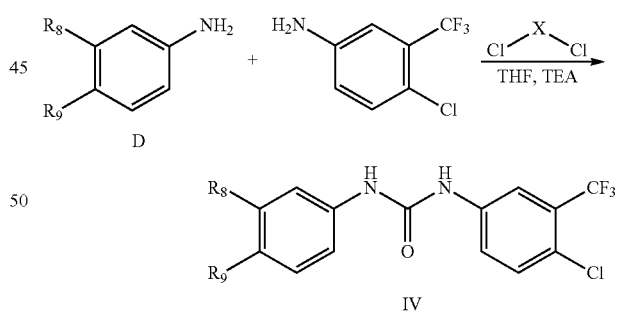

In the synthesis scheme IV, R$_8$ is a substituted phenoxyl group (C$_6$H$_5$O—), such as

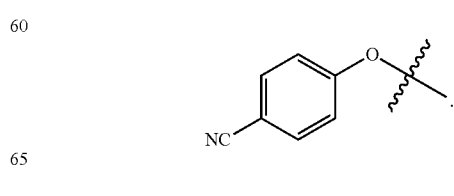

R$_9$ is H.

X is

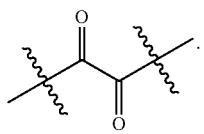 [SMILES: *C(=O)C(*)=O]

Embodiment 6: Synthesis Scheme IV

The examples of the synthetic compounds for the synthesis scheme IV are listed in Table 6 below.

TABLE 6

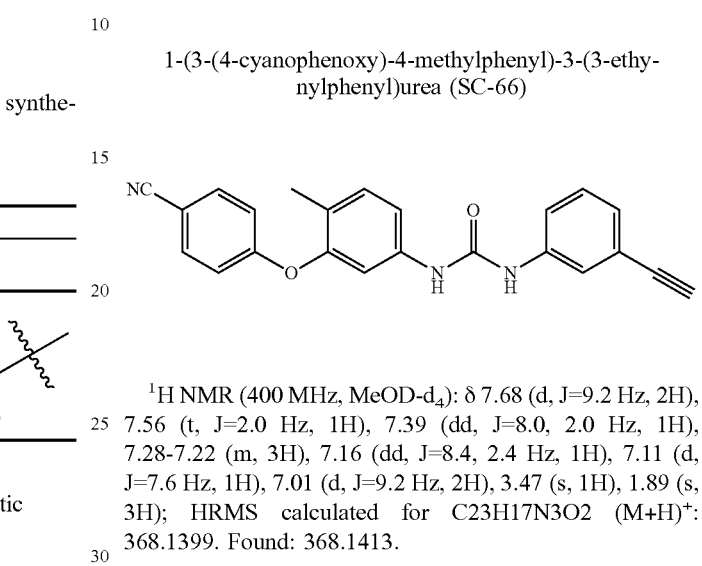

Synthetic Method SC-69 (Example of Synthetic Scheme IV)

1 equiv of oxalyl chloride was dissolved in dried THF at ice bath. 1 equiv of 4-chloro-3-(trifluoromethyl)aniline and 4 equiv of trimethylamine in THF was slowly added to the reaction mixture. The mixture was stirred at 60° C. for 30 minutes. After cooled down to room temperature, 1 equiv of 4-(3-aminophenoxy)benzonitrile in dried THF was slowly added to the mixture at ice bath. The mixture was stirred at 60° C. for 8 hr. The resulting solution was filtered to get rid of the salt and the filtrate was concentrated for chromatography to obtain compound SC-69.

Spectral Data of SC Exemplary Compounds 1-(3-(4-cyanophenoxy)phenyl)-3-(3-ethynylphenyl)urea (SC-65)

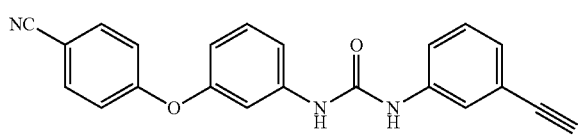 [SMILES: C#Cc1cccc(NC(=O)Nc2cccc(Oc3ccc(C#N)cc3)c2)c1]

$^1$H NMR (400 MHz, MeOD-d$_4$): δ 7.70 (d, J=8.8 Hz, 1H), 7.57 (s, 1H), 7.42-7.33 (m, 3H), 7.25 (t, J=8.0 Hz, 1H), 7.21 (d, J=8.0 Hz, 1H), 7.12-7.09 (m, 3H), 6.75 (dd, J=8.0 Hz, 1H), 3.45 (s, 1H); $^{13}$C NMR (100 MHz, MeOD-d$_4$): δ 163.0, 156.8, 154.8, 142.5, 140.5, 135.4, 131.4, 129.9, 127.4, 124.2, 123.4, 120.7, 119.6, 116.5, 115.2, 112.0, 106.8, 84.2, 78.4; HRMS calculated for C22H15N3O2: 352.1086. Found: 352.1080.

1-(3-(4-cyanophenoxy)-4-methylphenyl)-3-(3-ethynylphenyl)urea (SC-66)

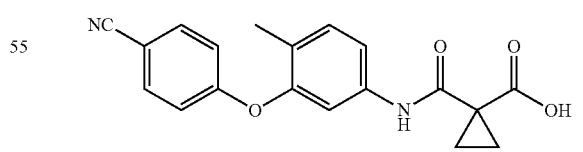

$^1$H NMR (400 MHz, MeOD-d$_4$): δ 7.68 (d, J=9.2 Hz, 2H), 7.56 (t, J=2.0 Hz, 1H), 7.39 (dd, J=8.0, 2.0 Hz, 1H), 7.28-7.22 (m, 3H), 7.16 (dd, J=8.4, 2.4 Hz, 1H), 7.11 (d, J=7.6 Hz, 1H), 7.01 (d, J=9.2 Hz, 2H), 3.47 (s, 1H), 1.89 (s, 3H); HRMS calculated for C23H17N3O2 (M+H)$^+$: 368.1399. Found: 368.1413.

N, N'-bis(3-(4-cyanophenoxy)phenyl)cyclopropane-1,1-dicarboxamide (SC-67)

$^1$H NMR (400 MHz, CDCl$_3$-d$_1$): δ 7.57 (d, J=9.2 Hz, 4H), 7.47 (s, 1H), 7.32 (t, J=8.0 Hz, 1H), 7.28 (d, J=8.0 Hz, 1H), 6.99 (d, J=9.2 Hz, 4H), 6.78 (dd, J=7.6 Hz, 2.2 Hz, 2H), 1.76-1.75 (m, 4H); HRMS calculated for C31H22N4O4 (M+Na)$^+$: 537.1539. Found: 537.1562.

1-(3-(4-cyanophenoxy)-4-methylphenyl)carbamoyl)cyclopropane-1-carboxylic acid (SC-68)

$^1$H NMR (400 MHz, CDCl$_3$-d$_1$): δ 7.54 (d, J=8.8 Hz, 4H), 7.37 (s, 2H), 7.21 (d, J=2.0 Hz, 4H), 6.88 (d, J=8.8 Hz, 4H), 2.09 (s, 6H), 1.77 (d, J=16 Hz, 4H); $^{13}$C NMR (100 MHz, CDCl$_3$-d$_1$): δ 177.3, 166.7, 161.5, 152.3, 137.1, 134.1, 131.8, 126.3, 118.8, 117.4, 116.7, 113.3, 105.2, 26.1, 21.8, 15.5; HRMS calculated for C19H16N2O4: 336.1110. Found: 336.1115.

N[1]-(4-chloro-3-(trifluoromethyl)phenyl)-N[2]-(3-(4-cyanophenoxy)phenyl) oxalamide (SC-69)

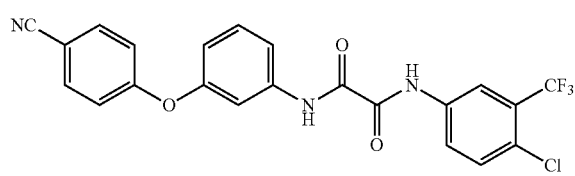 [SMILES: N#Cc1ccc(Oc2cccc(NC(=O)C(=O)Nc3ccc(Cl)c(C(F)(F)F)c3)c2)cc1]

$^1$H NMR (400 MHz, DMSO-d$_6$): δ 8.47 (d, J=2.0 Hz, 1H), 8.15 (dd, J=8.8, 2.0 Hz, 1H), 7.87 (d, J=8.8 Hz, 2H), 7.75-7.70 (m, 3H), 7.46 (t, J=8.0 Hz, 1H), 7.17 (d, J=8.8 Hz, 2H), 6.95 (dd, J=8.0, 2.0 Hz, 1H); $^{13}$C NMR (100 MHz, DMSO-d$_6$): δ 160.5, 158.7, 158.1, 154.9, 139.2, 137.1, 134.6, 132.1, 130.5, 126.6 (m), 125.4, 125.2, 122.6 (m), 119.3 (m), 118.9, 118.6, 116.6, 115.8, 111.4, 105.5; HRMS calculated for C22H13ClF3N3O3: 459.0598. Found: 459.0607.

N[1]-(3-((4-cyanocyclohexa-2,4-dien-1-yl)oxy)cyclohexa-2,4-dien-1-yl)-N[2]-(3-(4-cyanophenoxy)phenyl) oxalamide (SC-70)

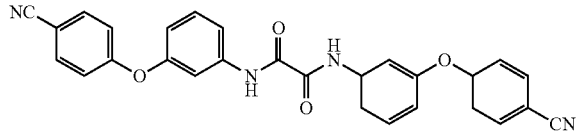 [SMILES: N#CC1=CCC(OC2=CC(NC(=O)C(=O)Nc3cccc(Oc4ccc(C#N)cc4)c3)CC=C2)C=C1]

$^1$H NMR (400 MHz, DMSO-d$_6$): δ 10.99 (s, 1H), 7.86 (d, J=8.8 Hz, 2H), 7.73 (d, J=8.4 Hz, 1H), 7.69 (s, 1H), 7.45 (t, J=8.4 Hz, 1H), 7.16 (d, J=8.8 Hz, 2H), 6.93 (d, J=8.4 Hz, 1H); $^{13}$C NMR (100 MHz, DMSO-d$_6$): δ 160.4, 158.3, 154.8, 139.2, 134.5, 130.4, 118.5, 116.5, 115.7, 111.3, 105.3.

N[1]-(3-((4-cyanocyclohexa-2,4-dien-1-yl)oxy)-4-methylcyclohexa-2,4-dien-1-yl)-N[2]-(3-(4-cyanophenoxy)-4-methylphenyl)oxalamide (SC-71)

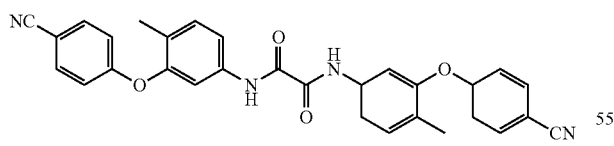

$^1$H NMR (400 MHz, DMSO-d$_6$): δ 10.88 (s, 1H), 7.83 (d, J=8.8 Hz, 2H), 7.65 (d, J=8.4 Hz, 1H), 7.61 (s, 1H), 7.35 (d, J=8.4 Hz, 1H), 7.05 (d, J=8.8 Hz, 2H), 2.09 (s, 3H); $^{13}$C NMR (100 MHz, DMSO-d$_6$): 160.6, 158.1, 151.9, 136.9, 134.5, 131.6, 125.4, 118.5, 117.3, 117.0, 112.0, 104.7, 15.0; HRMS calculated for C29H23N5O3 (M+H)+: 507.2032. Found: 507.2054.

1-(4-chloro-3-(trifluoromethyl)phenyl)-3-(7-(4-cyanophenoxy)naphthalen-1-yl)urea (SC-72)

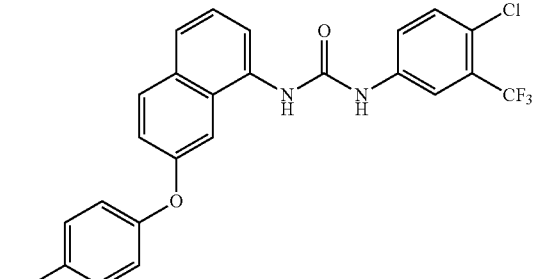

$^1$H NMR (400 MHz, DMSO-d$_6$): δ 8.09-8.07 (m, 2H), 7.97 (d, J=7.6 Hz, 1H), 7.83-7.81 (m, 3H), 7.75 (d, J=8.4 Hz, 1H), 7.64-7.58 (m, 2H), 7.50 (t, J=7.6 Hz, 1H), 7.37 (d, J=9.2 Hz, 1H), 7.15 (d, J=8.4 Hz, 2H); $^{13}$C NMR (100 MHz, DMSO-d$_6$): δ 161.3, 152.7, 151.8, 146.6, 139.2, 134.6, 133.5, 131.9, 131.4, 131.3, 127.3, 126.6 (m), 125.5, 123.6, 122.8, 122.5 (m), 120.3, 119.3, 118.5, 117.6, 116.6 (m), 111.7, 105.0; HRMS calculated for C25H15ClF3N3O2 (M−H)−: 480.0727. Found: 480.0705.

1,3-bis(7-(4-cyanophenoxy)naphthalen-1-yl)urea (SC-73)

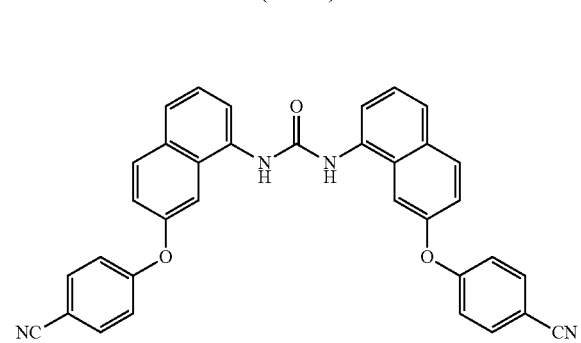

$^1$H NMR (400 MHz, DMSO-d$_6$): δ 8.99 (s, 2H), 8.08-8.05 (m, 4H), 7.93 (d, J=2.4 Hz, 2H), 7.83 (d, J=8.8 Hz, 4H), 7.72 (d, J=8.4 Hz, 2H), 7.51 (t, J=8.0 Hz, 2H), 7.37 (dd, J=9.2, 2.4 Hz, 2H), 7.14 (d, J=8.8 Hz, 4H); HRMS calculated for C35H22N4O3 (M+Na)+: 569.1590. Found: 569.1589.

1-((7-(4-cyanophenoxy)naphthalen-1-yl)carbamoyl) cyclopropane carboxylic acid (SC-75)

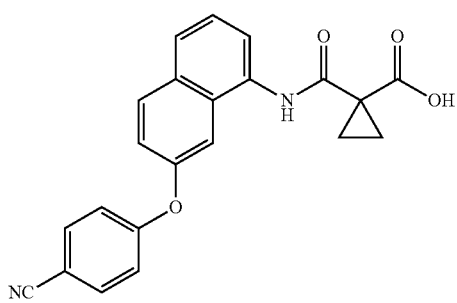 [SMILES: N#Cc1ccc(Oc2ccc3cccc(NC(=O)C4(C(=O)O)CC4)c3c2)cc1]

¹H NMR (400 MHz, CDCl₃-d₁): δ 10.93 (s, 1H), 8.05 (d, J=7.6 Hz, 1H), 7.89 (d, J=8.8 Hz, 1H), 7.68 (d, J=8.4 Hz, 1H), 7.63-7.59 (m, 3H), 7.45 (t, J=7.6 Hz, 1H), 7.22 (dd, J=8.8, 2.4 Hz, 1H), 7.06 (d, J=8.8 Hz, 2H), 1.89 (s, 2H), 1.76 (s, 2H); HRMS calculated for C22H16N2O4: 372.1110. Found: 372.1103.

1,3-bis(3-(4-cyanophenoxy)phenyl)thiourea (SC-76)

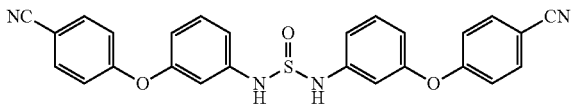 [SMILES: N#Cc1ccc(Oc2cccc(NS(=O)Nc3cccc(Oc4ccc(C#N)cc4)c3)c2)cc1]

¹H NMR (400 MHz, MeOD-d₄): δ 7.76 (d, J=8.8 Hz, 2H), 7.59 (t, J=8.0 Hz, 1H), 7.25-7.19 (m, 2H), 7.18 (d, J=8.8 Hz, 2H), 7.12 (t, J=2.4 Hz, 1H); ¹³C NMR (100 MHz, MeOD-d₄): δ 161.8, 158.0, 135.7, 134.0, 133.1, 121.2, 120.2, 120.1, 115.7, 108.3.

1,3-bis(4-chloro-3-(trifluoromethyl)phenyl)urea (SC-78)

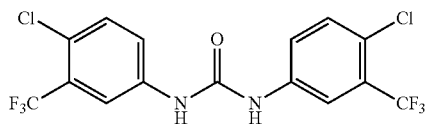 [SMILES: O=C(Nc1ccc(Cl)c(C(F)(F)F)c1)Nc1ccc(Cl)c(C(F)(F)F)c1]

¹H NMR (400 MHz, MeOD-d₄): δ 7.97 (s, 2H), 7.64 (d, J=8.8 Hz, 2H), 7.49 (d, J=8.8 Hz, 2H); ¹³C NMR (100 MHz, MeOD-d₄): δ 154.2, 139.8, 132.9, 129.3 (m), 125.7, 124.4 (m), 124.3, 118.8; HRMS calculated for C15H8Cl2F6N2O (M−H)⁻: 414.9840. Found: 414.9847.

1-(4-chloro-3-(trifluoromethyl)phenyl)-3-(3-(3-chloro-4-cyanophenoxy) phenyl)urea (SC-79)

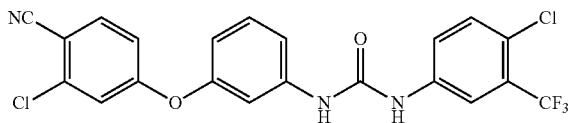 [SMILES: N#Cc1ccc(Oc2cccc(NC(=O)Nc3ccc(Cl)c(C(F)(F)F)c3)c2)cc1Cl]

¹H NMR (400 MHz, MeOD-d₄): δ 7.95 (d, J=2.8 Hz, 1H), 7.76 (t, J=8.8 Hz, 1H), 7.64 (dd, J=8.8, 2.8 Hz, 1H), 7.49 (d, J=8.8 Hz, 1H), 7.42 (t, J=2.0 Hz, 1H), 7.38 (t, J=8.0 Hz, 1H), 7.26 (dd, J=8.0, 2.0 Hz, 1H), 7.18 (d, J=2.4 Hz, 1H), 7.05 (dd, J=8.8, 2.4 Hz, 1H), 6.79 (dd, J=8.0, 2.4 Hz, 1H); ¹³C NMR (100 MHz, MeOD-d₄): δ 163.8, 156.2, 154.5, 142.5, 140.0, 139.1, 136.9, 133.0, 131.6, 129.4 (q), 125.6, 124.3, 122.9, 119.7, 118.8 (q), 17.5, 117.2, 116.8, 115.6, 112.4, 107.6.

1-(4-chloro-3-(trifluoromethyl)phenyl)-3-(3-(4-cyano-2-fluorophenoxy) phenyl) urea (SC-80)

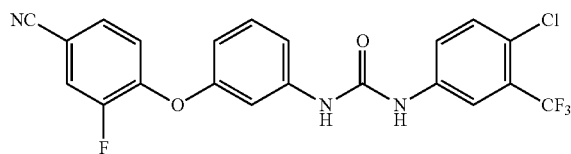 [SMILES: N#Cc1ccc(Oc2cccc(NC(=O)Nc3ccc(Cl)c(C(F)(F)F)c3)c2)c(F)c1]

¹H NMR (400 MHz, MeOD-d₄): δ 7.95 (d, J=2.8 Hz, 1H), 7.71 (dd, J=10.4, 2.0 Hz, 1H), 7.63 (dd, J=8.4, 2.0 Hz, 1H), 7.54 (d, J=8.0 Hz, 1H), 7.49 (d, J=9.2 Hz, 1H), 7.39 (t, J=2.0 Hz, 1H), 7.35 (t, J=8.4 Hz, 1H), 7.21 (d, J=8.4 Hz, 1H), 7.14 (t, J=8.0 Hz, 1H), 6.75 (dd, J=8.0, 2.8 Hz, 1H); HRMS calculated for C21H12ClF4N3O2 (M−H)⁻: 448.0476. Found: 448.0476.

1,3-bis(3-(3-chloro-4-cyanophenoxy)-4-methylphenyl)urea (SC-82)

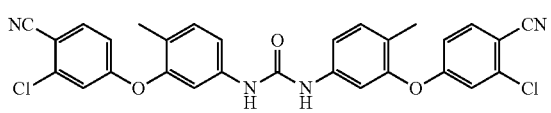 [SMILES: Cc1ccc(NC(=O)Nc2ccc(C)c(Oc3ccc(C#N)c(Cl)c3)c2)cc1Oc1ccc(C#N)c(Cl)c1]

¹H NMR (400 MHz, DMSO-d₆): δ 8.82 (s, 2H), 7.93 (d, J=8.8 Hz, 2H), 7.34 (d, J=2.4 Hz, 2H), 7.27 (d, J=8.8 Hz, 2H), 7.23 (d, J=2.4 Hz, 2H), 7.16 (dd, J=2.4 Hz, 2H), 6.94 (dd, J=8.8, 2.4 Hz, 2H), 2.04 (s, 6H); ¹³C NMR (100 MHz, DMSO-d₆): δ 171.4, 161.9, 161.0, 148.8, 146.7, 145.9, 141.5, 132.2, 127.0, 125.5, 125.0, 120.0, 114.9, 24.4; HRMS calculated for C29H20Cl2N4O3: 542.0912. Found: 542.0910.

1,3-bis(3-(3-bromo-4-cyanophenoxy)-4-methylphenyl)urea (SC-83)

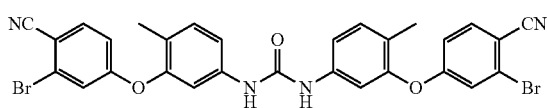 [SMILES: Cc1ccc(NC(=O)Nc2ccc(C)c(Oc3ccc(C#N)c(Br)c3)c2)cc1Oc1ccc(C#N)c(Br)c1]

¹H NMR (400 MHz, DMSO-d₆): δ 8.90 (s, 1H), 7.96 (d, J=8.8 Hz, 1H), 7.45-7.39 (m, 2H), 7.33 (d, J=8.4 Hz, 1H), 7.23 (dd, J=8.4, 2.0 Hz, 1H), 7.04 (dd, J=8.8 Hz, 1H), 2.05 (s, 3H); ¹³C NMR (100 MHz, DMSO-d₆): δ 161.0, 151.8, 150.9, 138.7, 136.0, 131.4, 125.5, 122.0, 119.8, 116.6, 115.6, 115.3, 110.0, 107.2, 14.3; HRMS calculated for C29H20Br2N4O3 (M−H)⁻: 628.9824. Found: 628.9842.

1,3-bis(3-(4-cyano-3-fluorophenoxy)-4-methylphenyl)urea (SC-84)

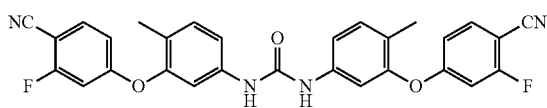 [SMILES: Cc1ccc(NC(=O)Nc2ccc(C)c(Oc3ccc(C#N)c(F)c3)c2)cc1Oc1ccc(C#N)c(F)c1]

¹H NMR (400 MHz, DMSO-d₆): δ 8.85 (s, 2H), 8.01 (dd, J=8.8, 6.4 Hz, 2H), 7.34 (d, J=2.0 Hz, 2H), 7.28 (d, J=8.4 Hz, 2H), 7.18-7.12 (m, 4H), 6.59 (dd, J=10.4, 2.4 Hz, 2H), 2.06 (s, 6H); HRMS calculated for C29H20F2N4O3 (M−H)⁺: 509.1425. Found: 509.1424.

1,3-bis(3-(4-cyano-2-fluorophenoxy)-4-methylphenyl)urea (SC-85)

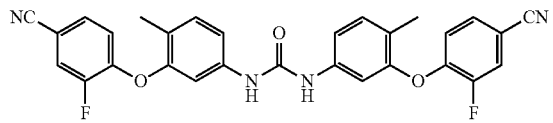 [SMILES: Cc1ccc(NC(=O)Nc2ccc(C)c(Oc3ccc(C#N)cc3F)c2)cc1Oc1ccc(C#N)cc1F]

¹H NMR (400 MHz, DMSO-d₆): δ 8.79 (s, 1H), 8.03 (dd, J=11.2, 2.0 Hz, 1H), 7.62 (d, J=8.4 Hz, 1H), 7.25-7.23 (m, 2H), 7.12 (dd, J=8.4, 2.0 Hz, 1H), 6.89 (t, J=8.4 Hz, 1H), 2.07 (s, 3H)

1,3-bis(3-((6-cyanopyridin-3-yl)oxy)-4-methyl phenyl)urea (SC-86)

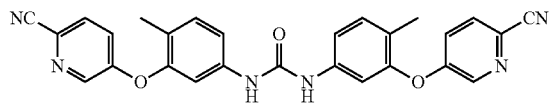

¹H NMR (400 MHz, DMSO-d₆): δ 8.88 (s, 1H), 8.47 (d, J=2.1 Hz, 1H), 7.99 (d, J=8.4 Hz, 1H), 7.33 (dd, J=8.4, 2.1 Hz, 2H), 7.27 (d, J=8.4 Hz, 1H), 7.15 (dd, J=8.0, 2.0 Hz, 1H), 2.05 (s, 3H); ¹³C NMR (100 MHz, DMSO-d₆): δ 156.5, 152.3, 151.4, 141.0, 139.2, 131.9, 130.6, 125.5, 123.2, 122.4, 117.4, 115.8, 110.1, 14.8.

1-(4-chloro-3-(trifluoromethyl)phenyl)-3-(3-((6-cyanopyridin-3-yl)oxy)-4-methylphenyl)urea (SC-87)

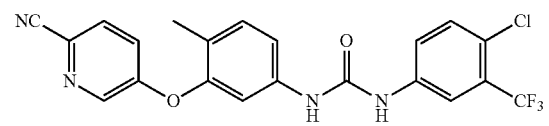 [SMILES: Cc1ccc(NC(=O)Nc2ccc(Cl)c(C(F)(F)F)c2)cc1Oc1ccc(C#N)nc1]

¹H NMR (400 MHz, DMSO-d₆): δ 9.15 (s, 1H), 8.94 (s, 1H), 8.49 (m, 1H), 8.05 (s, H), 8.00 (d, J=8.0 Hz, 1H), 7.59-7.58 (m, 2H), 7.37-7.33 (m, 2H), 7.29 (d, J=8.4 Hz, 1H), 7.22 (dd, J=8.4, 2.0 Hz, 1H), 2.06 (s, 1H); ¹³C NMR (100 MHz, DMSO-d₆): δ 156.1, 151.9, 151.1, 140.7, 138.8, 138.6 (m), 131.6, 130.3, 126.7, 126.4, 125.3, 122.9, 122.8, 122.7, 122.5, 122.4 (m), 117.0, 116.5, 115.8, 110.2, 14.5; HRMS calculated for C21H14ClF3N4O2 (M−H)⁺: 445.0679. Found: 445.0679.

1-(4-chloro-3-(trifluoromethyl)phenyl)-3-(3-(4-cyano-3-fluorophenoxy)-4-methylphenyl)urea (SC-88)

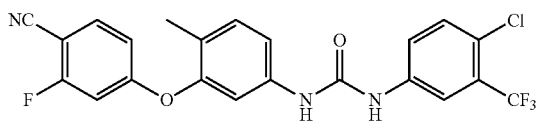 [SMILES: Cc1ccc(NC(=O)Nc2ccc(Cl)c(C(F)(F)F)c2)cc1Oc1ccc(C#N)c(F)c1]

¹H NMR (400 MHz, MeOD-d₄): δ 7.94 (d, J=2.8 Hz, 1H), 7.81 (dd, J=8.8, 6.0 Hz, 1H), 7.63 (dd, J=8.8, 2.8 Hz, 1H), 7.48 (d, J=8.8 Hz, 1H), 7.35 (d, J=2.0 Hz, 1H), 7.30 (d, J=8.4 Hz, 1H), 7.22 (dd, J=8.4, 2.0 Hz, 1H), 6.97-6.94 (m, 1H), 6.51 (dd, J=10.4, 2.4 Hz, 1H), 2.15 (s, 3H); HRMS calculated for C22H14ClF4N3O2 (M−H)⁻: 462.0632. Found: 462.0645.

1-(3-(3-bromo-4-cyanophenoxy)-4-methylphenyl)-3-(4-chloro-3-(trifluoromethyl)phenyl)urea (SC-89)

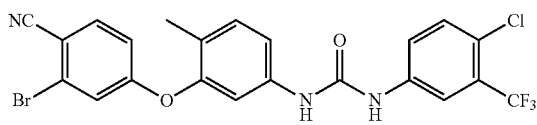

¹H NMR (400 MHz, DMSO-d₆): δ 9.15 (s, 1H), 8.94 (s, 1H), 8.06 (d, J=2.0 Hz, 1H), 7.90 (d, J=8.8 Hz, 1H), 7.60-7.58 (m, 2H), 7.35-7.34 (m, 2H), 7.28 (d, J=8.8 Hz, 1H), 7.22 (dd, J=8.4, 2.0 Hz, 1H), 6.98 (dd, J=8.8, 2.4 Hz, 1H), 2.04 (s, 1H); ¹³C NMR (100 MHz, DMSO-d₆): δ 161.4, 152.1, 151.3, 139.0, 138.8, 136.5, 131.8, 126.5 (m), 125.9, 124.0, 123.0, 122.9, 122.7, 122.3, 120.3, 117.0, 116.7 (m), 116.1, 115.6, 110.8, 107.6, 14.7; HRMS calculated for C22H14BrClF3N3O2 (M−H)⁻: 521.9832. Found: 521.9821.

1,3-bis(4-(4-cyanophenoxy)-2-methylphenyl)urea (SC-90)

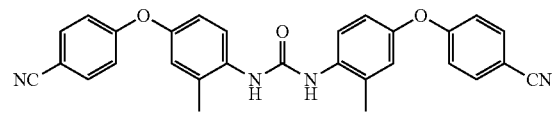 [SMILES: Cc1cc(Oc2ccc(C#N)cc2)ccc1NC(=O)Nc1ccc(Oc2ccc(C#N)cc2)cc1C]

¹H NMR (400 MHz, DMSO-d₆): δ 8.32 (s, 2H), 7.86 (d, J=8.0 Hz, 2H), 7.82 (d, J=8.0 Hz, 4H), 7.07 (d, J=8.0 Hz, 4H), 7.03 (d, J=4.0 Hz, 2H), 6.95 (dd, J=8.0, 4.0 Hz, 2H), 2.29 (s, 6H); ¹³C NMR (100 MHz, DMSO-d₆): δ 161.5, 152.8, 148.9, 134.5, 134.3, 130.4, 123.1, 121.8, 118.5, 117.9, 117.2, 104.3, 17.8; HRMS calculated for C29H22N4O3 (M−H)⁻: 473.1614. Found: 473.1608.

1,3-bis(2-chloro-5-(4-cyanophenoxy)phenyl)urea (SC-91)

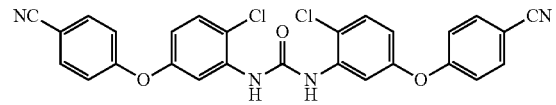 [SMILES: N#Cc1ccc(Oc2ccc(Cl)c(NC(=O)Nc3cc(Oc4ccc(C#N)cc4)ccc3Cl)c2)cc1]

¹H NMR (400 MHz, DMSO-d₆): δ 9.27 (s, 2H), 7.88 (d, J=3.2 Hz, 2H), 7.82 (d, J=8.8 Hz, 4H), 7.53 (d, J=8.8 Hz, 2H), 7.12 (d, J=8.8 Hz, 4H), 6.83 (dd, J=8.8, 3.2 Hz, 2H); ¹³C NMR (100 MHz, DMSO-d₆): δ 160.6, 153.3, 151.9, 137.0, 134.6, 130.6, 118.5, 118.2, 118.1, 115.3, 113.4, 105.4; HRMS calculated for C27H16C12N4O3 (M−H)⁻: 513.0521. Found: 513.0516.

1,3-bis(4-chloro-3-(4-cyanophenoxy)phenyl)urea (SC-92)

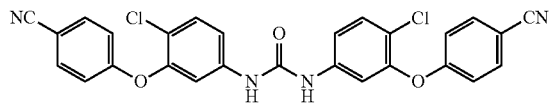 [SMILES: N#Cc1ccc(Oc2cc(NC(=O)Nc3ccc(Cl)c(Oc4ccc(C#N)cc4)c3)ccc2Cl)cc1]

¹H NMR (400 MHz, DMSO-d₆): δ 9.08 (s, 2H), 7.84 (d, J=8.8 Hz, 4H), 7.52-7.48 (m, 4H), 7.28 (dd, J=8.8, 2.4 Hz, 2H), 7.06 (d, J=8.8 Hz, 4H); ¹³C NMR (100 MHz, DMSO-d₆): δ 160.1, 151.9, 149.3, 140.0, 134.5, 130.7, 118.4, 117.5, 117.0, 116.6, 111.9, 105.2; HRMS calculated for C27H16C12N4O3 (M−H)⁻: 513.0521. Found: 513.0524.

1,3-bis(5-(4-cyanophenoxy)-2-methylphenyl)urea (SC-93)

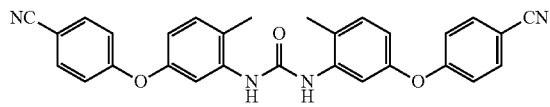 [SMILES: Cc1ccc(Oc2ccc(C#N)cc2)cc1NC(=O)Nc1cc(Oc2ccc(C#N)cc2)ccc1C]

¹H NMR (400 MHz, DMSO-d₆): δ 8.52 (s, 2H), 7.80 (d, J=8.8 Hz, 4H), 7.71 (d, J=2.8 Hz, 2H), 7.27 (d, J=8.4 Hz, 2H), 7.06 (d, J=8.8 Hz, 4H), 6.73 (dd, J=8.4, 2.8 Hz, 2H), 2.29 (s, 6H); ¹³C NMR (100 MHz, DMSO-d₆): δ 170.8, 161.9, 161.6, 148.3, 143.9, 140.9, 133.2, 128.1, 126.9, 123.5, 121.9, 114.0, 26.9; HRMS calculated for C29H22N4O3 (M−H)⁻: 473.1614. Found: 473.1598.

(1Z,1'Z)-4,4'-(((carbonylbis(azanediyl))bis(2-methyl-5,1-phenylene))bis(oxy))bis(N'-hydroxybenzimidamide) (SC-94)

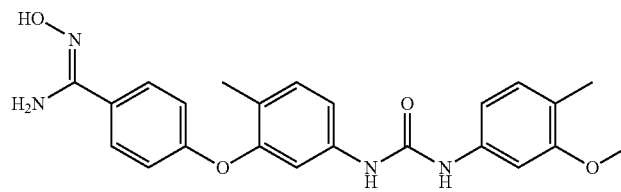

¹H NMR (400 MHz, MeOD-d₄): δ 7.84 (d, J=8.8 Hz, 2H), 7.59 (d, J=8.8 Hz, 2H), 7.21-7.17 (m, 4H), 7.14-7.06 (m, 4H), 6.93-6.89 (m, 2H); HRMS calculated for C29H28N6O5 (M+H)+: 541.2199. Found: 541.2178.

1-(4-chloro-3-(trifluoromethyl)phenyl)-3-(4-(4-cyanophenoxy)-2-fluorophenyl)urea (SC-96)

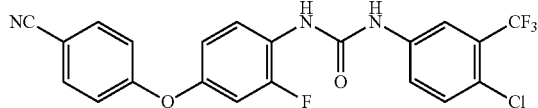 [SMILES: N#Cc1ccc(Oc2ccc(NC(=O)Nc3ccc(Cl)c(C(F)(F)F)c3)c(F)c2)cc1]

¹H NMR (400 MHz, DMSO-d₆): δ 9.47 (s, 1H), 8.68 (s, 1H), 8.11-8.06 (m, 2H), 7.84 (d, J=8.8 Hz, 2H), 7.63-7.58 (m, 2H), 7.23 (dd, J=11.6, 2.8 Hz, 1H), 7.12 (d, J=8.8 Hz, 2H), 6.98 (dd, J=8.8, 1.6 Hz, 1H); HRMS calculated for C21H12ClF4N3O2 (M−H)⁻: 448.0476. Found: 448.0477.

1,3-bis(5-(4-cyanophenoxy)-2-fluorophenyl)urea (SC-97)

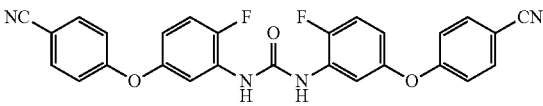 [SMILES: N#Cc1ccc(Oc2ccc(F)c(NC(=O)Nc3cc(Oc4ccc(C#N)cc4)ccc3F)c2)cc1]

¹H NMR (400 MHz, DMSO-d₆): δ 9.32 (s, 2H), 7.94 (m, 2H), 7.81 (d, J=8.8 Hz, 4H), 7.35 (t, J=9.2 Hz, 2H), 7.07 (d, J=8.8 Hz, 4H), 6.81 (m, 2H); ¹³C NMR (100 MHz, DMSO-d₆): δ 161.1, 151.5, 149.9, 147.4, 134.4, 128.5, 118.4, 117.4, 116.1, 113.9, 111.8, 104.8; HRMS calculated for C27H16F2N4O3 (M−H)⁻: 481.1112. Found: 481.1110.

1,3-bis(3-(4-cyano-3-methylphenoxy)-4-methylphenyl)urea (SC-98)

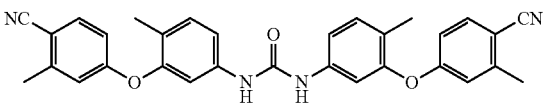 [SMILES: Cc1cc(Oc2cc(NC(=O)Nc3ccc(C)c(Oc4ccc(C#N)c(C)c4)c3)ccc2C)ccc1C#N]

¹H NMR (400 MHz, DMSO-d₆): δ 8.76 (s, 1H), 7.72 (d, J=8.4 Hz, 2H), 7.26 (d, J=2.0 Hz, 2H), 7.23 (d, J=8.0 Hz, 2H), 7.12 (dd, J=8.4, 2.4 Hz, 2H), 6.93 (d, J=2.0 Hz, 2H), 6.77 (dd, J=8.4, 2.4 Hz, 2H), 2.41 (s, 6H), 2.02 (s, 6H); ¹³C NMR (100 MHz, DMSO-d₆): δ 160.7, 152.1, 151.8, 144.1, 138.9, 134.5, 131.5, 122.4, 117.7, 117.5, 115.2, 114.0, 110.3, 105.0, 19.8, 14.8; HRMS calculated for C31H26N4O3 (M−H)⁻: 501.1927. Found: 501.1924.

1-(3-(4-cyanophenoxy)-4-methylphenyl)-3-(3-((6-cyanopyridin-3-yl)oxy)-4-methylphenyl)urea (SC-99)

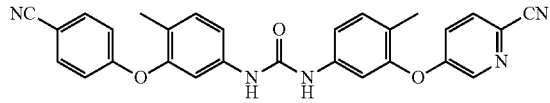 [SMILES: Cc1ccc(NC(=O)Nc2ccc(C)c(Oc3ccc(C#N)nc3)c2)cc1Oc1ccc(C#N)cc1]

¹H NMR (400 MHz, CDCl3-d₁): δ 8.29 (d, J=2.8 Hz, 1H), 7.52 (d, J=8.8 Hz, 1H), 7.48 (d, J=9.2 Hz, 2H), 7.36 (s, 1H), 7.25 (s, 1H), 7.15 (d, J=2.0 Hz, 1H), 7.11-7.06 (m, 4H), 6.98 (t, J=12.0 Hz, 2H), 6.84 (d, J=9.2 Hz, 2H), 2.05 (s, 3H), 2.04 (s, 3H).

1-(3-(3-chloro-4-cyanophenoxy)-4-methyl phenyl)-3-(3-(4-cyanophenoxy)-4-methylphenyl)urea (SC-100)

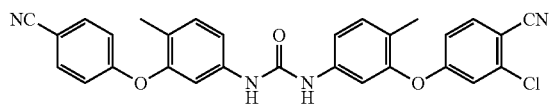 [SMILES: Cc1ccc(NC(=O)Nc2ccc(C)c(Oc3ccc(C#N)c(Cl)c3)c2)cc1Oc1ccc(C#N)cc1]

¹H NMR (400 MHz, CDCl3-d₁): δ 7.56-7.53 (m, 3H), 7.20-7.16 (m, 3H), 7.16 (s, 1H), 7.11 (s, 1H), 7.07-7.03 (m, 2H), 6.92-6.87 (m, 3H), 6.81 (d, J=8.8 Hz, 1H), 6.62 (d, J=10.4 Hz, 1H), 6.56 (d, J=9.6 Hz, 1H), 2.09 (s, 6H); ¹³C NMR (100 MHz, DMSO-d₆): δ 161.7, 152.2, 151.9, 151.4, 139.2, 139.1, 137.1, 136.3, 134.5, 131.8, 131.7, 122.6, 118.6, 117.4, 116.8, 115.9, 115.4, 115.3, 110.6, 105.6, 104.4, 14.9, 14.8; HRMS calculated for C29H21ClN4O3 (M−H)⁻: 507.1224. Found: 507.1218.

1-(3-(4-cyano-3-methylphenoxy)-4-methylphenyl)-3-(3-((6-cyanopyridin-3-yl)oxy)-4-methylphenyl) urea (SC-102)

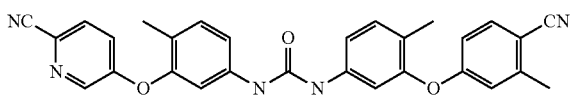

¹H NMR (400 MHz, MeOD-d₄): δ 8.37 (d, J=2.8 Hz, 1H), 7.78 (d, J=8.4 Hz, 1H), 7.57 (d, J=8.8 Hz, 1H), 7.31 (dd, J=8.4, 2.8 Hz, 2H), 7.25 (d, J=8.4 Hz, 1H); ¹³C NMR (100 MHz, DMSO-d₆): δ 160.9, 156.5, 152.2, 152.1, 152.0, 151.4, 144.3, 141.0, 139.2, 139.0, 134.7, 131.9, 131.7, 130.6, 125.5, 123.2, 122.6, 122.3, 117.9, 117.6, 117.3, 115.8, 115.7, 114.1, 110.5, 110.2, 110.1, 105.1, 19.9, 14.9, 14.8; HRMS calculated for C29H23N5O3 (M−H)⁻: 488.1723. Found: 488.1718.

1-(3-(3-chloro-4-cyanophenoxy)-4-methyl phenyl)-3-(3-(((6-cyanopyridin-3-yl)oxy)51-4-methylphenyl) urea (SC-103)

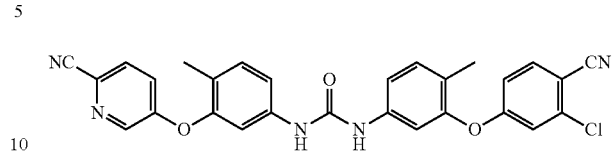

¹H NMR (400 MHz, CDCl3-d₁): δ 8.28 (d, J=2.8 Hz, 1H), 7.61 (d, J=9.6 Hz, 2H), 7.51 (d, J=8.4 Hz, 1H), 7.46 (d, J=8.8 Hz, 1H), 7.17 (dd, J=18.2, 2.0 Hz, 2H), 7.08 (d, J=8.8 Hz, 3H), 6.93-6.89 (m, 2H), 6.86 (d, J=2.0 Hz, 1H), 6.75 (dd, J=8.8, 2.4 Hz, 1H), 2.04 (s, 3H), 2.02 (s, 3H); HRMS calculated for C28H20ClN5O3 (M−H)⁻: 508.1176. Found: 508.1176.

1,3-bis(3-((6-cyano-5-fluoropyridin-3-yl)oxy)-4-methylphenyl)urea (SC-104)

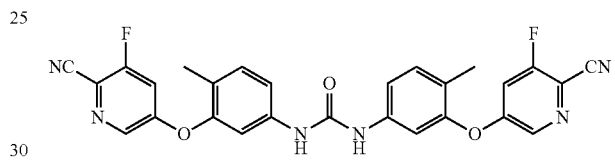

¹H NMR (400 MHz, MeOD-d₄): δ 8.13 (t, J=2.4 Hz, 2H), 7.36 (d, J=8.4 Hz, 2H), 7.24-7.19 (m, 4H), 7.14 (dd, J=8.4, 2.4 Hz, 2H), 2.31 (s, 6H); HRMS calculated for C27H18F2N6O3 (M−H)⁻: 511.1330. Found: 511.1333.

1-(4-chloro-3-(trifluoromethyl)phenyl)-3-(5-(4-cyanophenoxy)-2-fluorophenyl)urea (SC-105)

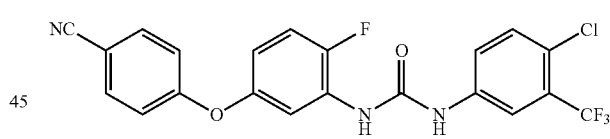

¹H NMR (400 MHz, DMSO-d₆): δ 8.04 (d, J=2.4 Hz, 1H), 7.94 (dd, J=6.8, 3.2 Hz, 1H), 7.84 (d, J=8.8 Hz, 2H), 7.62-7.57 (m, 2H), 7.38-7.33 (m, 1H), 7.05 (d, J=8.8 Hz, 2H), 6.84-6.80 (m, 1H); ¹³C NMR (100 MHz, DMSO-d₆): δ 161.1, 151.7, 150.0, 147.6, 138.5, 134.4, 131.9, 128.4, 126.7 (m), 122.9, 122.6 (m), 118.5, 117.4, 116.5 (m), 116.2, 116.0, 114.1, 112.1, 104.9; HRMS calculated for C21H12ClF4N3O2 (M−H)⁻: 448.0476. Found: 448.0454.

1,3-bis(4-(4-cyanophenoxy)-2-fluorophenyl)urea (SC-106)

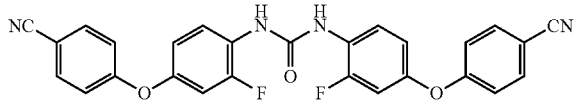 [SMILES: N#Cc1ccc(Oc2ccc(NC(=O)Nc3ccc(Oc4ccc(C#N)cc4)cc3F)c(F)c2)cc1]

¹H NMR (400 MHz, DMSO-d₆): δ 9.05 (s, 2H), 8.19 (t, J=9.2 Hz, 2H), 7.83 (d, J=8.8 Hz, 4H), 7.22 (dd, J=12.0, 2.4 Hz, 2H), 7.11 (d, J=8.8 Hz, 4H), 6.98 (d, J=9.2 Hz, 2H); ¹³C NMR (100 MHz, DMSO-d₆): δ 161.5, 153.3, 151.8, 150.9, 148.7, 134.5, 124.5, 121.5, 118.5, 117.6, 116.7, 108.4, 108.2, 105.0; HRMS calculated for C27H16F2N4O3 (M−H)⁻: 481.1112. Found: 481.1106.

1-(3-(4-cyanophenoxy)-4-methylphenyl)-3-(7-(4-cyanophenoxy)naphthalen-1-yl)urea (SC-107)

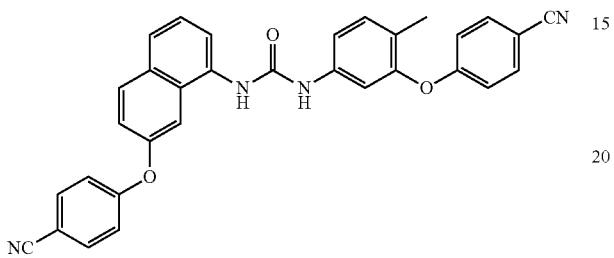

¹H NMR (400 MHz, DMSO-d₆): δ 9.01 (s, 1H), 8.67 (s, 1H), 8.06 (d, J=8.8 Hz, 1H), 7.98 (d, J=6.8 Hz, 1H), 7.84-7.79 (m, 5H), 7.70 (d, J=7.6 Hz, 1H), 7.47 (t, J=8.0 Hz, 1H), 7.36 (dd, J=9.6, 2.4 Hz, 2H), 7.27 (d, J=8.0 Hz, 1H), 7.16-7.12 (m, 3H), 7.02 (d, J=9.6 Hz, 2H), 2.05 (s, 3H); ¹³C NMR (100 MHz, DMSO-d₆): δ 161.4, 161.1, 152.7, 152.0, 151.7, 139.3, 134.7, 134.6, 133.8, 131.8, 131.4, 131.3, 126.9, 125.6, 123.1, 122.5, 120.3, 118.7, 118.6, 118.4, 117.6, 117.0, 115.2, 111.6, 110.3, 105.0, 104.5, 14.9; HRMS calculated for C32H22N4O3 (M−H)⁻: 509.1614. Found: 509.1592.

1-(4-chloro-3-(trifluoromethyl)phenyl)-3-(4-(3-chloro-4-cyanophenoxy)-2-fluorophenyl)urea (SC-108)

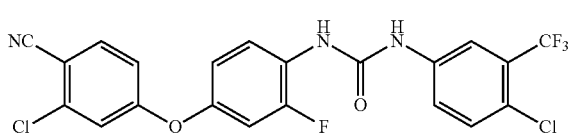 [SMILES: N#Cc1ccc(Oc2ccc(NC(=O)Nc3ccc(Cl)c(C(F)(F)F)c3)c(F)c2)cc1Cl]

¹H NMR (400 MHz, DMSO-d₆): δ 9.48 (s, 1H), 8.69 (s, 1H), 8.14-8.09 (m, 2H), 7.94 (d, J=8.8 Hz, 1H), 7.66-7.59 (m, 2H), 7.32 (d, J=2.4 Hz, 1H), 7.26 (dd, J=11.6, 2.8 Hz, 1H), 7.07 (dd, J=8.8, 2.4 Hz, 1H), 7.01 (d, J=8.8 Hz, 1H); ¹³C NMR (100 MHz, DMSO-d₆): δ 161.6, 153.7, 151.9, 151.3, 148.5, 138.7, 136.9, 136.0, 126.7 (m), 124.5, 122.7, 122.5 (m), 122.3, 121.2, 118.1, 116.3, 1162, 115.7, 108.5, 108.3, 105.7; HRMS calculated for C21H11Cl2F4N3O2: 483.0164. Found: 483.0169.

1-(4-chloro-3-(trifluoromethyl)phenyl)-3-(7-(3-chloro-4-cyanophenoxy)naphthalen-1-yl)urea (SC-109)

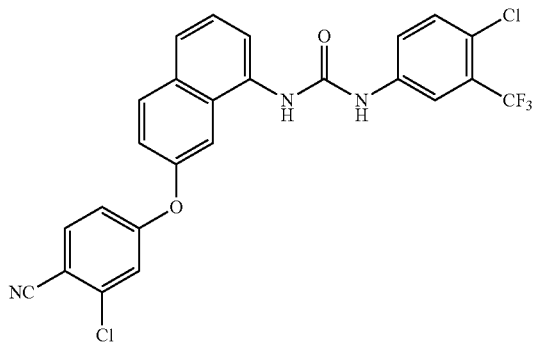 [SMILES: N#Cc1ccc(Oc2ccc3cccc(NC(=O)Nc4ccc(Cl)c(C(F)(F)F)c4)c3c2)cc1Cl]

¹H NMR (400 MHz, DMSO-d₆): δ 9.36 (s, 1H), 8.82 (s, 1H), 8.10-8.08 (m, 2H), 7.98-7.93 (m, 2H), 7.86 (d, J=2.4 Hz, 1H), 7.76 (d, J=8.0 Hz, 1H), 7.63-7.59 (m, 2H), 7.51 (t, J=8.0 Hz, 1H), 7.41 (dd, J=8.8, 2.4 Hz, 1H), 7.38 (d, J=2.4 Hz, 1H), 7.10 (dd, J=8.8, 2.4 Hz, 1H); ¹³C NMR (100 MHz, DMSO-d₆): δ 161.6, 152.2, 150.9, 138.8, 136.7, 135.8, 133.2, 131.5, 131.2, 131.0, 127.0, 126.3 (m), 125.3, 123.3, 122.5, 122.3 (m), 121.8, 119.8, 119.1, 117.8, 116.2 (m), 115.9, 115.4, 111.6, 105.3; HRMS calculated for C25H14Cl2F3N3O2: 515.0415. Found: 515.0419.

1-(5-(4-cyanophenoxy)-2-fluorophenyl)-3-(3-((6-cyanopyridin-3-yl)oxy)-4-methylphenyl)urea (SC-110)

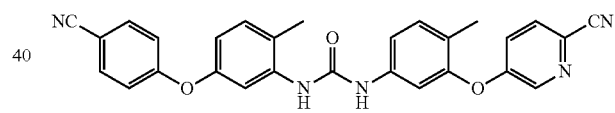

¹H NMR (400 MHz, MeOD-d₄): δ 9.27 (s, 1H), 8.97 (s, 1H), 8.47 (d, J=2.8 Hz, 1H), 7.98 (d, J=8.4 Hz, 1H), 7.92 (dd, J=7.2, 2.8 Hz, 1H), 7.81 (d, J=8.8 Hz, 2H), 7.34-7.27 (m, 4H), 7.14 (dd, J=8.4, 2.0 Hz, 1H), 7.07 (d, J=8.8 Hz, 2H), 6.79-6.76 (m, 1H), 2.05 (s, 3H); ¹³C NMR (100 MHz, DMSO-d₆): δ 161.3, 156.5, 151.8, 151.5, 150.2, 147.6, 141.1, 138.8, 134.6, 132.1, 130.6, 129.0, 125.6, 123.2, 122.9, 118.6, 117.6, 117.4, 116.8, 116.3, 115.8, 113.8, 111.9, 110.2, 105.0, 14.9; HRMS calculated for C27H18FN5O3 (M−H)⁻: 478.1315. Found: 478.1297.

1-(4-chloro-3-(trifluoromethyl)phenyl)-3-(3-(4-cyanophenoxy)-4-fluorophenyl)urea (SC-111)

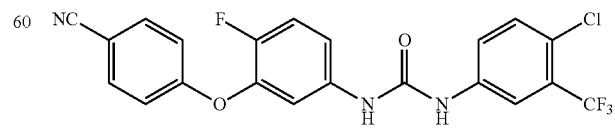

¹H NMR (400 MHz, MeOD-d₄): δ 7.95 (d, J=2.4 Hz, 1H), 7.72 (d, J=8.8 Hz, 2H), 7.63 (dd, J=8.8, 2.4 Hz, 1H), 7.51-7.48 (m, 2H), 7.28-7.21 (m, 2H), 7.09 (d, J=8.8 Hz, 2H); $^{13}$C NMR (100 MHz, MeOD-d$_4$): δ162.6, 154.5, 152.6, 150.2, 142.5, 140.0, 137.6, 135.4, 132.9, 129.1 (m), 125.5, 124.2, 119.5, 118.7 (m), 118.4 (m), 118.1, 117.9, 115.3, 107.1; HRMS calculated for C21H12ClF4N3O2: 449.0554. Found: 449.0558.

1,3-bis(3-(4-cyanophenoxy)-4-fluorophenyl)urea (SC-112)

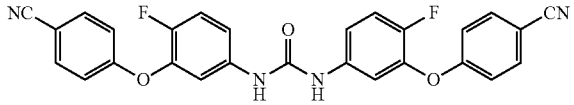 [SMILES: N#Cc1ccc(Oc2cc(NC(=O)Nc3ccc(F)c(Oc4ccc(C#N)cc4)c3)ccc2F)cc1]

$^1$H NMR (400 MHz, DMSO-d$_6$): δ 8.97 (s, 2H), 7.84 (d, J=8.4 Hz, 4H), 7.49 (d, J=7.2 Hz, 2H), 7.35 (t, J=9.2 Hz, 2H), 7.24 (d, J=8.8 Hz, 2H), 7.12 (d, J=8.4 Hz, 4H); $^{13}$C NMR (100 MHz, DMSO-d$_6$): δ 160.2, 152.1, 149.5, 147.1, 140.2, 140.1, 136.4, 134.3, 118.2, 117.1, 116.9, 116.3, 116.0, 115.9, 112.3, 105.1; HRMS calculated for C27H16F2N4O3: 482.1190. Found: 482.1183.

1,3-bis(3-((4-cyanonaphthalen-1-yl)oxy)-4-methyl phenyl)urea (SC-113)

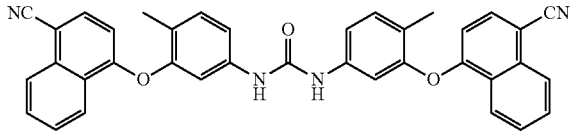 [SMILES: Cc1ccc(NC(=O)Nc2ccc(C)c(Oc3ccc(C#N)c4ccccc34)c2)cc1Oc1ccc(C#N)c2ccccc12]

$^1$H NMR (400 MHz, DMSO-d$_6$): δ 8.83 (s, 2H), 8.46 (d, J=8.0 Hz, 2H), 8.12 (d, J=8.4 Hz, 2H), 8.02 (d, J=8.0 Hz, 2H), 7.88 (t, J=8.4 Hz, 2H), 7.79 (t, J=8.4 Hz, 2H), 7.37 (d, J=2.0 Hz, 2H), 7.29 (d, J=8.4 Hz, 2H), 7.18 (dd, J=8.4, 2.0 Hz, 2H), 6.62 (d, J=8.0 Hz, 2H), 2.04 (s, 6H); $^{13}$C NMR (100 MHz, DMSO-d$_6$): δ 157.1, 152.0, 151.8, 138.9, 134.3, 132.9, 1315, 129.6, 127.4, 124.0, 122.3, 117.3, 115.4, 110.4, 107.8, 101.7; 14.5.

1-(4-chloro-3-(trifluoromethyl)phenyl)-3-(3-((4-cyanonaphthalen-1-yl)oxy)-4-methylphenyl)urea (SC-114)

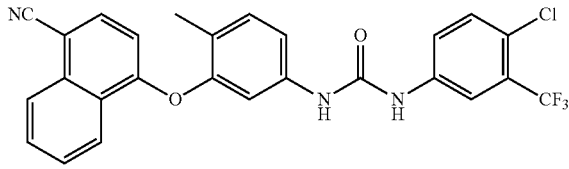 [SMILES: Cc1ccc(NC(=O)Nc2ccc(Cl)c(C(F)(F)F)c2)cc1Oc1ccc(C#N)c2ccccc12]

$^1$H NMR (400 MHz, MeOD-d$_4$): δ 9.15 (s, 1H), 8.95 (s, 1H), 8.48 (d, J=8.4 Hz, 1H), 8.13 (d, J=8.4 Hz, 1H), 8.06-8.04 (m, 2H), 7.89 (t, J=8.0 Hz, 1H), 7.79 (t, J=8.0 Hz, 1H), 7.60-7.55 (m, 1H), 7.41 (d, J=2.0 Hz, 1H), 7.33 (d, J=8.4 Hz, 1H), 7.25 (dd, J=8.0, 2.0 Hz, 1H), 6.65 (d, J=8.0 Hz, 1H), 2.06 (s, 1H); HRMS calculated for C26H17ClF3N3O2: 495.0961. Found: 495.0959.

1-(3,5-bis(trifluoromethyl)phenyl)-3-(3-(4-cyanophenoxy)-4-methylphenyl) urea (SC-131)

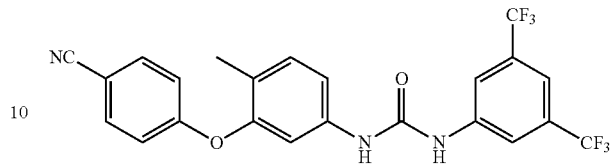

$^1$H NMR (300 MHz, DMSO-d$_6$): δ 9.38 (s, 1H), 9.09 (s, 1H), 8.10 (s, 2H), 7.82 (d, J=9.0 Hz, 2H), 7.62 (s, 1H), 7.35 (d, J=2.1 Hz, 1H), 7.30 (d, J=8.7 Hz, 1H), 7.24 (dd, J=8.7, 2.1 Hz, 1H) 7.02 (d, J=9.0 Hz, 2H), 2.05 (s, 3H); $^{13}$C NMR (75 MHz, DMSO-d$_6$): δ 161.1, 152.3, 151.9, 141.7, 138.7, 134.7, 131.9, 130.7 (q), 128.7, 125.1, 121.5, 118.8, 118.1 (d), 117.9, 116.9, 114.4 (q), 113.8 (q), 15.0.

1-(3-(4-cyanophenoxy)-4-methylphenyl)-3-(4-fluoro-3-(trifluoromethyl) phenyl)urea (SC-132)

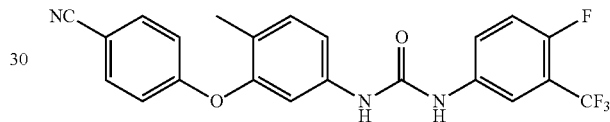

$^1$H NMR (300 MHz, DMSO-d$_6$): δ 9.03 (s, 1H), 8.92 (s, 1H), 7.95 (dd, J=6.6, 2.7 Hz, 1H), 7.83 (d, J=9.0 Hz, 2H), 7.64~7.58 (m, 1H), 7.40 (t, J=9.6 Hz, 1H), 7.33 (d, J=2.1 Hz, 1H), 7.28 (d, J=8.1 Hz, 1H), 7.19 (dd, J=8.1, 2.1 Hz, 1H), 7.02 (d, J=9.0 Hz, 2H), 2.05 (s, 3H); $^{13}$C NMR (75 MHz, DMSO-d$_6$): δ 161.1, 155.3 (d), 152.5, 152.0, 139.0, 136.4 (d), 134.7, 131.8, 124.4 (d), 123.0, 120.8, 118.8, 117.5 (d), 116.9, 116.6 (d), 116.1 (q), 116.0, 110.9, 104.6, 15.0.

1-(4-chloro-3-(trifluoromethyl)phenyl)-3-(3-(4-cyanophenoxy)-4-methylphenyl)urea (SC-133)

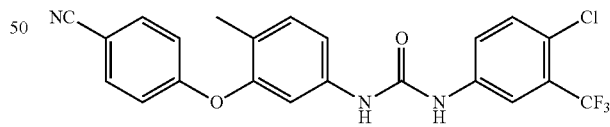

$^1$H NMR (300 MHz, DMSO-d$_6$): δ 9.16 (s, 1H), 8.96 (s, 1H), 8.06 (s, 1H), 7.83 (d, J=9.0 Hz, 2H), 7.61 (s, 1H), 7.60 (s, 1H), 7.33 (d, J=2.1 Hz, 1H), 7.29 (d, J=8.4 Hz, 1H), 7.20 (d, J=8.1, 2.1 Hz, 1H), 7.02 (d, J=9.0 Hz, 2H), 2.05 (s, 3H); $^{13}$C NMR (75 MHz, DMSO-d$_6$): δ 161.1, 152.3, 152.0, 139.2, 138.9, 134.7, 132.0, 131.7, 126.7 (q), 124.6, 123.2, 123.1, 122.4 (q), 121.0, 118.8, 117.0, 115.8, 110.9, 104.6, 15.0.

1-(3-(4-cyanophenoxy)-4-methylphenyl)-3-(3-(trifluoromethyl)phenyl)urea (SC-134)

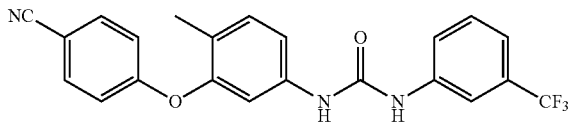

¹H NMR (300 MHz, DMSO-d₆): δ 9.04 (s, 1H), 8.90 (s, 1H), 7.96 (s, 1H), 7.83 (d, J=9.0 Hz, 2H), 7.56~7.46 (m, 2H), 7.35 (d, J=2.1 Hz, 1H), 7.31~7.27 (m, 2H), 7.19 (dd, J=8.1, 2.1 Hz, 1H), 7.02 (d, J=9.0 Hz, 2H), 2.05 (s, 3H); ¹³C NMR (75 MHz, DMSO-d₆): δ 161.1, 152.4, 152.0, 140.4, 139.1, 134.7, 131.9, 129.9, 129.3 (q), 124.2 (q), 122.9, 121.9, 118.8, 118.2 (q), 116.9, 115.7, 114.2 (q), 110.8, 104.6, 15.0.

1-(4-(cyanomethyl)phenyl)-3-(3-(4-cyanophenoxy)-4-methylphenyl)urea (SC-135)

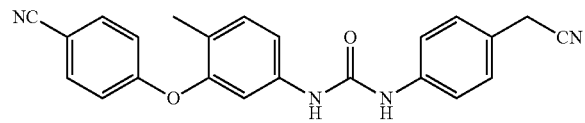

¹H NMR (300 MHz, DMSO-d₆): δ 8.81 (s, 1H), 8.76 (s, 1H), 7.83 (d, J=9.0 Hz, 2H), 7.43 (d, J=8.4 Hz, 2H), 7.35 (d, J=2.1 Hz, 1H), 7.27 (d, J=8.4 Hz, 1H), 7.23 (d, J=8.4 Hz, 2H), 7.15 (dd, J=8.4, 2.1 Hz, 1H), 7.02 (d, J=9.0 Hz, 2H), 3.93 (s, 2H), 2.05 (s, 3H); ¹³C NMR (75 MHz, DMSO-d₆): δ 161.2, 152.4, 152.0, 139.3, 139.0, 134.7, 131.8, 128.5, 124.4, 122.6, 119.5, 118.8, 118.7, 117.0, 115.4, 110.5, 104.6, 21.7, 15.0.

1-(4-chloro-3-(4-cyanophenoxy)phenyl)-3-(4-fluoro-3-(trifluoromethyl)phenyl)urea (SC-137)

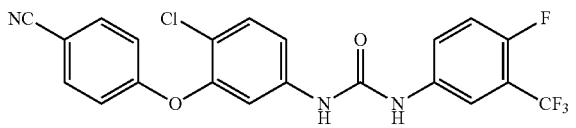 [SMILES: N#Cc1ccc(Oc2cc(NC(=O)Nc3ccc(F)c(C(F)(F)F)c3)ccc2Cl)cc1]

¹H NMR (300 MHz, DMSO-d₆): δ 9.16 (s, 2H), 7.94 (dd, J=6.6, 2.7 Hz, 1H), 7.87 (d, J=8.7 Hz, 2H), 7.66~7.60 (m, 1H), 7.56~7.53 (m, 2H), 7.43 (t, J=9.3 Hz, 1H), 7.33 (dd, J=9.3, 2.7 Hz, 1H), 7.09 (d, J=8.7 Hz, 2H); ¹³C NMR (75 MHz, DMSO-d₆): δ 160.3, 152.4, 152.1, 149.5, 140.3, 136.2 (d), 134.8, 130.9, 124.6 (d), 118.6, 117.7, 117.5, 117.2, 116.9, 116.3 (m), 112.2, 105.4.

1-(4-chloro-3-(4-cyanophenoxy)phenyl)-3-(3-(trifluoromethyl)phenyl)urea (SC-138)

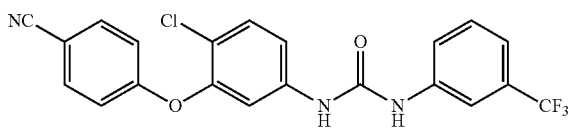 [SMILES: N#Cc1ccc(Oc2cc(NC(=O)Nc3cccc(C(F)(F)F)c3)ccc2Cl)cc1]

¹H NMR (300 MHz, DMSO-d₆): δ 9.14 (s, 2H), 7.96 (s, 1H), 7.86 (t, J=9.0 Hz, 2H), 7.58~7.48 (m, 4H), 7.35~7.31 (m, 2H), 7.09 (d, J=9.0 Hz, 2H); ¹³C NMR (75 MHz, DMSO-d₆): δ 160.4, 152.3, 149.5, 140.3, 140.2, 134.8, 130.9, 129.9, 129.5 (q), 124.2 (q), 122.1, 118.6, 118.4 (q), 117.7, 117.2, 116.8, 114.4 (q), 112.2, 105.4.

1-(4-chloro-3-(4-cyanophenoxy)phenyl)-3-(4-chloro-3-(trifluoromethyl) phenyl)urea (SC-139)

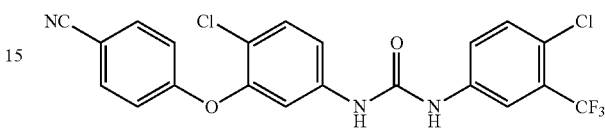

¹H NMR (300 MHz, DMSO-d₆): δ 9.27 (s, 1H), 9.20 (s, 1H), 8.05 (s, 1H), 7.86 (d, J=9.0 Hz, 2H), 7.65-7.54 (m, 4H), 7.34 (dd, J=9.0, 2.4 Hz, 1H), 7.09 (d, J=9.0 Hz, 2H); ¹³C NMR (75 MHz, DMSO-d₆): δ 160.3, 152.2, 149.5, 140.1, 139.0, 134.8, 132.0, 130.9, 126.5 (q), 123.4, 122.8 (q), 122.7 (q), 118.6, 117.2, 117.1, 117.0, 116.9, 112.3, 105.4.

1-(4-chloro-3-(4-cyanophenoxy)phenyl)-3-(3-ethynylphenyl)urea (SC-140)

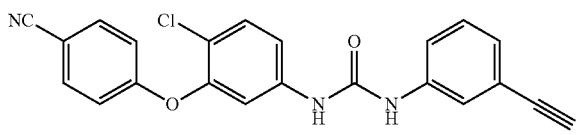

¹H NMR (300 MHz, DMSO-d₆): δ 9.06 (s, 1H), 8.88 (s, 1H), 7.86 (d, J=9.0 Hz, 2H), 7.62 (s, 1H), 7.55 (s, 1H), 7.53 (d, J=5.7 Hz, 1H), 7.39 (d, J=9.0 Hz, 1H), 7.32~7.25 (m, 2H), 7.12~7.07 (m, 3H), 4.15 (s, 1H); ¹³C NMR (75 MHz, DMSO-d₆): δ 160.3, 152.3, 149.5, 140.4, 139.5, 134.7, 130.9, 129.2, 125.4, 122.1, 121.2, 119.2, 118.6, 117.5, 117.2, 116.6, 112.0, 105.4, 83.5, 80.5.

1-(3,5-bis(trifluoromethyl)phenyl)-3-(2-chloro-5-(4-cyanophenoxy)phenyl) urea (SC-141)

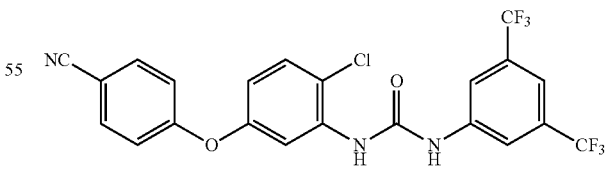

¹H NMR (300 MHz, DMSO-d₆): δ 10.14 (s, 1H), 8.61 (s, 1H), 8.04 (s, 2H), 7.99 (d, J=2.7 Hz, 1H), 7.85 (d, J=8.4 Hz, 2H), 7.67 (s, 1H), 7.57 (d, J=8.7 Hz, 1H), 7.15 (d, J=8.4 Hz, 2H), 6.87 (dd, J=8.7, 3.0 Hz, 1H); ¹³C NMR (75 MHz, DMSO-d₆): δ 160.7, 153.5, 151.9, 141.2, 136.9, 134.7, 130.9 (q), 130.7, 125.0 (q), 118.6, 118.2, 118.1, 118.0, 115.5, 115.0 (q), 112.9, 105.5.

1-(4-chloro-3-(trifluoromethyl)phenyl)-3-(2-chloro-5-(4-cyanophenoxy) phenyl)urea (SC-142)

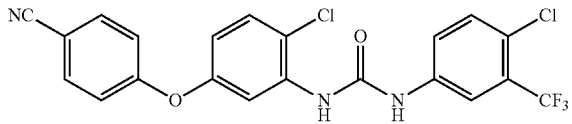

¹H NMR (300 MHz, DMSO-d₆): δ 9.97 (s, 1H), 8.56 (s, 1H), 8.03 (s, 1H), 8.00 (d, J=3.0 Hz, 1H), 7.86 (d, J=8.7 Hz, 2H), 7.61 (s, 2H), 7.56 (d, J=8.7 Hz, 1H), 7.16 (d, J=8.7 Hz, 2H), 6.86 (dd, J=8.7, 3.0 Hz, 1H); ¹³C NMR (75 MHz, DMSO-d₆): δ 160.7, 153.5, 151.9, 138.7, 137.1, 134.7, 132.2, 130.7, 126.8 (q), 123.1, 122.9 (q), 122.7 (q), 118.7, 118.2, 117.8, 116.8 (q), 115.2, 112.5, 105.4.

1-(2-chloro-5-(4-cyanophenoxy)phenyl)-3-(4-fluoro-3-(trifluoromethyl) phenyl)urea (SC-143)

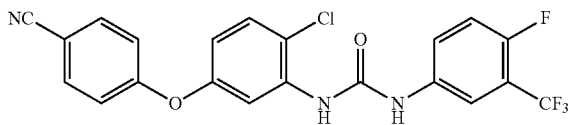 [SMILES: N#Cc1ccc(Oc2ccc(Cl)c(NC(=O)Nc3ccc(F)c(C(F)(F)F)c3)c2)cc1]

¹H NMR (300 MHz, DMSO-d₆): δ 9.84 (s, 1H), 8.51 (s, 1H), 8.01 (d, J=2.7 Hz, 1H), 7.95 (dd, J=6.6, 2.7 Hz, 1H), 7.86 (d, J=8.4 Hz, 2H), 7.63~7.54 (m, 2H), 7.44 (t, J=9.8 Hz, 1H), 7.15 (d, J=8.4 Hz, 2H), 6.85 (dd, J=8.7, 2.7 Hz, 1H); ¹³C NMR (75 MHz, DMSO-d₆): δ 160.7, 155.5, 153.5, 152.2, 152.0, 137.2, 135.9 (d), 134.7, 130.6, 124.3 (d), 118.6, 118.7 (q), 118.2, 117.9, 117.7, 116.6 (q), 116.0 (q), 115.0, 112.4, 105.5.

1-(5-(4-cyanophenoxy)-2-fluorophenyl)-3-(3-ethynylphenyl)urea (SC-144)

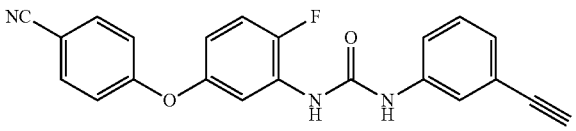 [SMILES: C#Cc1cccc(NC(=O)Nc2cc(Oc3ccc(C#N)cc3)ccc2F)c1]

¹H NMR (300 MHz, DMSO-d₆): δ 9.23 (s, 1H), 8.81 (s, 1H), 7.98 (dd, J=6.6, 2.7 Hz, 1H), 7.84 (d, J=8.7 Hz, 2H), 7.64 (s, 1H), 7.39~7.27 (m, 3H), 7.14~7.08 (m, 3H), 6.80 (dt, J=8.7, 2.7 Hz, 1H), 4.16 (s, 1H); ¹³C NMR (75 MHz, DMSO-d₆): δ 161.3, 152.1, 150.4, 150.2 (d), 147.2, 139.3, 134.7, 129.0 (d), 127.5 (d), 122.2, 120.9, 118.9, 118.7, 117.7, 116.2 (d), 113.8 (d), 111.9, 105.1, 83.4, 80.5.

1-(5-(4-cyanophenoxy)-2-fluorophenyl)-3-(4-fluoro-3-(trifluoromethyl) phenyl)urea (SC-145)

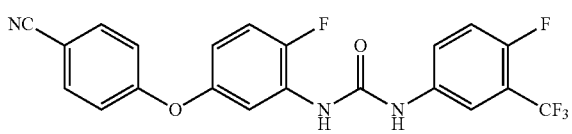

¹H NMR (300 MHz, DMSO-d₆): δ 9.46 (s, 1H), 8.86 (s, 1H), 7.96 (dd, J=7.2, 3.0 Hz, 2H), 7.84 (d, J=8.7 Hz, 2H), 7.61~7.56 (m, 1H), 7.44 (t, J=10.0 Hz, 1H), 7.40~7.33 (m, 1H), 7.10 (d, J=8.7 Hz, 2H), 6.84 (dt, J=9.0, 3.0 Hz, 1H); ¹³C NMR (75 MHz, DMSO-d₆): δ 161.3, 160.0, 155.4 (d), 152.2 (d), 150.6, 150.2 (d), 147.8, 135.9 (d), 134.7, 128.8 (d), 124.3 (d), 118.7 (q), 118.3 (d), 117.7, 116.4 (m), 116.2 (d), 115.9 (q), 114.1 (d), 112.2 (d), 105.0.

1-(4-(cyanomethyl)phenyl)-3-(5-(4-cyanophenoxy)-2-fluorophenyl)urea (SC-146)

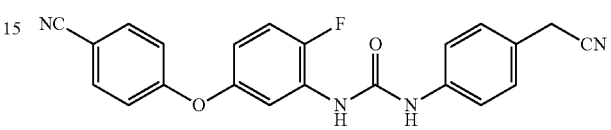

¹H NMR (300 MHz, DMSO-d₆): δ 9.21 (s, 1H), 8.78 (s, 1H), 8.01 (dd, J=6.6, 2.7 Hz, 1H), 7.84 (d, J=8.4 Hz, 2H), 7.44 (d, J=8.4 Hz, 2H), 7.38~7.31 (m, 1H), 7.26 (d, J=9.0 Hz, 2H), 7.11 (d, J=8.7 Hz, 2H), 6.79 (dt, J=8.7, 3.3 Hz, 1H), 3.95 (s, 2H); ¹³C NMR (75 MHz, DMSO-d₆): δ 161.3, 151.9, 150.3 (d), 147.1, 138.5, 134.7, 129.1 (d), 128.7, 124.8, 119.1 (d), 118.6, 117.7, 116.3, 116.0, 113.6 (d), 111.7 (d), 105.0, 21.7.

1-(3,5-bis(trifluoromethyl)phenyl)-3-(4-chloro-3-(4-cyanophenoxy)phenyl) urea (SC-148)

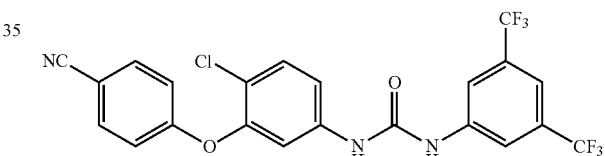

¹H NMR (300 MHz, DMSO-d₆): δ 9.50 (s, 1H), 9.34 (s, 1H), 8.10 (s, 2H), 7.86 (d, J=9.0 Hz, 2H), 7.66 (s, 1H), 7.71 (d, J=5.4 Hz, 1H), 7.56 (s, 1H), 7.38 (dd, J=9.0, 2.4 Hz, 1H), 7.09 (d, J=9.0 Hz, 2H); ¹³C NMR (75 MHz, DMSO-d₆): δ 160.3, 152.3, 149.5, 141.5, 140.0, 134.8, 130.7 (q), 125.1 (q), 118.6, 118.4, 118.3, 118.2, 117.2, 117.1, 114.7 (q), 112.6, 105.4.

1-(4-chloro-3-(4-cyanophenoxy)phenyl)-3-(4-(cyanomethyl)phenyl)urea (SC-149)

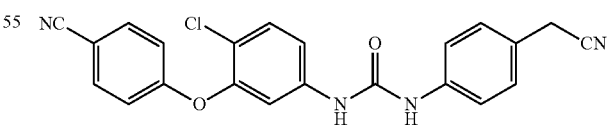

¹H NMR (300 MHz, DMSO-d₆): δ 9.01 (s, 1H), 8.83 (s, 1H), 7.86 (d, J=9.0 Hz, 2H), 7.56 (s, 1H), 7.53 (d, J=8.7 Hz, 1H), 7.44 (d, J=8.4 Hz, 2H), 7.30 (dd, J=9.0, 2.7 Hz, 1H), 7.24 (d, J=8.4 Hz, 2H), 7.09 (d, J=8.7 Hz, 2H), 3.94 (s, 2H); ¹³C NMR (75 MHz, DMSO-d₆): δ 160.3, 152.3, 149.5, 140.5, 138.7, 134.7, 130.9, 128.6, 124.6, 119.4, 118.8, 118.6, 117.3, 117.3, 116.5, 111.8, 105.4, 21.7.

1-(3-(4-cyanophenoxy)-4-fluorophenyl)-3-(3-ethynylphenyl)urea (SC-150)

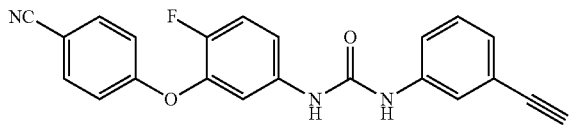 [SMILES: C#Cc1cccc(NC(=O)Nc2ccc(F)c(Oc3ccc(C#N)cc3)c2)c1]

$^1$H NMR (300 MHz, DMSO-d$_6$): δ 8.95 (s, 1H), 8.85 (s, 1H), 7.86 (d, J=8.1 Hz, 2H), 7.64 (s, 1H), 7.53 (dd, J=7.5, 2.7 Hz, 1H), 7.39 (t, J=6.0 Hz, 2H), 7.30~7.24 (m, 2H), 7.14 (d, J=8.7 Hz, 2H), 7.08 (d, J=7.5 Hz, 1H), 4.15 (s, 1H); $^{13}$C NMR (75 MHz, DMSO-d$_6$): δ 160.6, 152.4, 150.3, 147.1, 140.5 (d), 139.7, 137.1 (d), 134.7, 129.2, 125.3, 122.1, 121.2, 119.1, 118.6, 117.5 (d), 117.0, 116.3 (d), 112.6, 105.5, 83.5, 80.4.

1-(3-(4-cyanophenoxy)-4-fluorophenyl)-3-(3-(trifluoromethyl)phenyl)urea (SC-151)

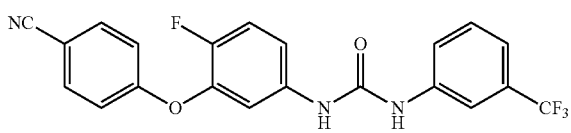 [SMILES: N#Cc1ccc(Oc2cc(NC(=O)Nc3cccc(C(F)(F)F)c3)ccc2F)cc1]

$^1$H NMR (300 MHz, DMSO-d$_6$): δ 9.11 (s, 1H), 9.02 (s, 1H), 7.97 (s, 1H), 7.86 (d, J=8.7 Hz, 2H), 7.85-7.47 (m, 3H), 7.42-7.27 (m, 3H), 7.14 (d, J=8.7 Hz, 2H); $^{13}$C NMR (75 MHz, DMSO-d$_6$): δ 160.6, 152.5, 150.4, 147.2, 140.5 (d), 140.3, 136.9 (d), 134.7, 129.9, 129.5 (q), 124.2 (q), 122.0, 118.6, 118.3 (q), 117.5 (d), 117.0, 116.5 (d), 114.3 (q), 112.8, 105.5.

1-(3,5-bis(trifluoromethyl)phenyl)-3-(3-(4-cyanophenoxy)-4-fluorophenyl) urea (SC-152)

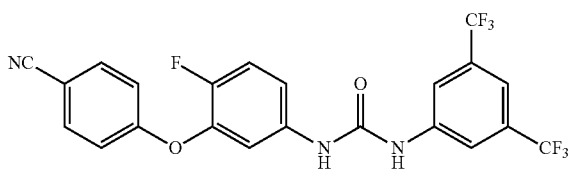 [SMILES: N#Cc1ccc(Oc2cc(NC(=O)Nc3cc(C(F)(F)F)cc(C(F)(F)F)c3)ccc2F)cc1]

$^1$H NMR (300 MHz, DMSO-d$_6$): δ 9.45 (s, 1H), 9.21 (s, 1H), 8.11 (s, 2H), 7.86 (d, J=9.0 Hz, 2H), 7.64 (s, 1H), 7.56 (dd, J=7.2, 2.4 Hz, 1H), 7.43~7.31 (m, 2H), 7.14 (d, J=9.0 Hz, 2H); $^{13}$C NMR (75 MHz, DMSO-d$_6$): δ 160.6, 152.4, 150.7, 147.5, 141.7, 140.5 (d), 136.6 (d), 134.7, 130.7 (q), 123.3 (q), 118.6, 118.2 (d), 117.5 (d), 117.1, 116.9, 114.6 (q), 113.3, 105.5.

1-(4-(cyanomethyl)phenyl)-3-(3-(4-cyanophenoxy)-4-fluorophenyl)urea (SC-153)

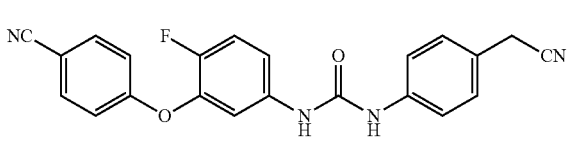 [SMILES: N#CCc1ccc(NC(=O)Nc2ccc(F)c(Oc3ccc(C#N)cc3)c2)cc1]

$^1$H NMR (300 MHz, DMSO-d$_6$): δ 8.90 (s, 1H), 8.81 (s, 1H), 7.86 (d, J=8.7 Hz, 2H), 7.54 (dd, J=7.8, 2.7 Hz, 1H), 7.44 (d, J=8.4 Hz, 2H), 7.37 (t, J=9.6 Hz, 1H), 7.28~7.23 (m, 3H), 7.14 (d, J=8.7 Hz, 2H), 3.94 (s, 2H); $^{13}$C NMR (75 MHz, DMSO-d$_6$): δ 160.6, 152.4, 150.2, 147.0, 140.5 (d), 138.9, 137.2 (d), 134.7, 128.6, 124.5, 119.4, 118.8, 118.6, 117.4 (d), 117.0, 116.2 (d), 112.4, 105.5, 21.7.

1-(3-(4-cyanophenoxy)-4-fluorophenyl)-3-(4-fluoro-3-(trifluoromethyl)phenyl)urea (SC-154)

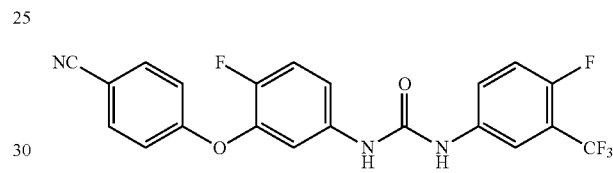

$^1$H NMR (300 MHz, DMSO-d$_6$): δ 9.09 (s, 1H), 9.02 (s, 1H), 7.95 (dd, J=6.6, 2.7 Hz, 1H), 7.86 (d, J=8.7 Hz, 2H), 7.66~7.60 (m, 1H), 7.53 (dd, J=7.2, 2.7 Hz, 1H), 7.46~7.27 (m, 3H), 7.14 (d, J=8.7 Hz, 2H); $^{13}$C NMR (75 MHz, DMSO-d$_6$): δ 160.6, 155.4 (q), 152.6, 152.1 (q), 150.4, 147.2, 140.5 (d), 136.9 (d), 136.3 (d), 134.7, 124.5 (d), 122.6 (q), 118.6, 117.5 (m), 117.0, 116.4 (q), 116.1 (q), 112.9, 105.5.

6-(4-cyanophenoxy)-N-(4-fluoro-3-(trifluoromethyl)phenyl)-2H-benzo[b][1,4]oxazine-4(3H)-carboxamide (SC-156)

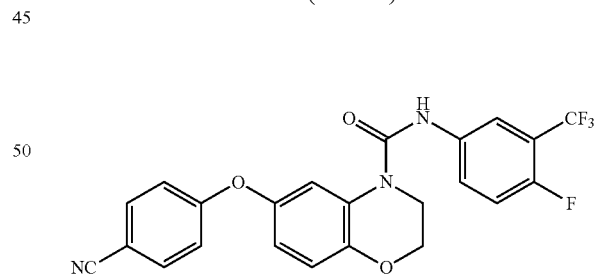

$^1$H NMR (300 MHz, CDCl$_3$-d$_1$): δ 7.60~7.50 (m, 4H), 7.16~7.10 (m, 3H), 7.01 (d, J=8.7 Hz, 1H), 6.97 (d, J=8.4 Hz, 2H), 6.83 (dd, J=9.0, 2.7 Hz, 1H), 4.32 (t, J=4.5 Hz, 2H), 3.95 (t, J=4.5 Hz, 2H); $^{13}$C NMR (75 MHz, CDCl$_3$-d$_1$): δ 161.9, 157.7 (q), 154.4 (q), 152.2, 148.0, 144.7, 134.4, 134.1 (d), 126.4, 125.2 (d), 122.4 (q), 119.7, 118.8, 118.7, 118.6, 117.8, 117.5, 114.8, 106.2, 66.5, 41.0.

N-(4-chloro-3-(trifluoromethyl)phenyl)-6-(4-cyanophenoxy)-2H-benzo[b][1,4]oxazine-4(3H)-carboxamide (SC-157)

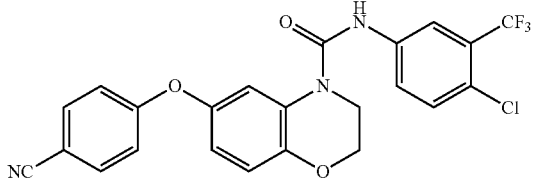 [SMILES: N#Cc1ccc(Oc2ccc3c(c2)N(C(=O)Nc2ccc(Cl)c(C(F)(F)F)c2)CCO3)cc1]

$^1$H NMR (300 MHz, CDCl$_3$-d$_1$): δ 7.64 (d, J=2.7 Hz, 1H), 7.58 (d, J=9.0 Hz, 2H), 7.52 (dd, J=9.0, 2.7 Hz, 1H), 7.40 (d, J=9.0 Hz, 1H), 7.17 (s, 1H), 7.09 (d, J=2.7 Hz, 1H), 7.02 (d, J=8.7 Hz, 1H), 6.97 (d, J=9.0 Hz, 2H), 6.84 (dd, J=8.7, 2.7 Hz, 1H), 4.32 (t, J=4.8 Hz, 2H), 3.95 (t, J=4.8 Hz, 2H); $^{13}$C NMR (75 MHz, CDCl$_3$-d$_1$): δ 161.9, 151.9, 148.0, 144.7, 136.9, 134.4, 132.2, 129.0 (q), 126.7 (q), 126.3, 123.7, 122.6 (q), 119.8, 118.7, 118.6, 118.5, 117.5, 114.8, 106.2, 66.5, 41.0.

N-(3,5-bis(trifluoromethyl)phenyl)-6-(4-cyanophenoxy)-2H-benzo[b][1,4]oxazine-4(3H)-carboxamide (SC-158)

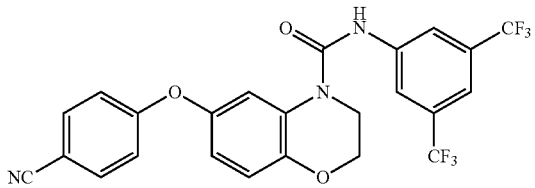 [SMILES: N#Cc1ccc(Oc2ccc3c(c2)N(C(=O)Nc2cc(C(F)(F)F)cc(C(F)(F)F)c2)CCO3)cc1]

$^1$H NMR (300 MHz, CDCl$_3$-d$_1$): δ 7.83 (s, 2H), 7.58 (d, J=9.0 Hz, 2H), 7.55 (s, 1H), 7.34 (s, 1H), 7.10 (d, J=2.4 Hz, 1H), 7.03 (d, J=9.3 Hz, 1H), 6.99 (d, J=9.0 Hz, 2H), 6.86 (dd, J=9.0, 2.7 Hz, 1H), 4.33 (t, J=4.5 Hz, 2H), 3.97 (t, J=4.5 Hz, 2H); $^{13}$C NMR (75 MHz, CDCl$_3$-d$_1$): δ 161.9, 151.8, 148.1, 144.8, 139.6, 134.4, 132.6 (q), 126.0, 123.2 (q), 119.9, 119.3 (q), 119.1, 118.7, 117.5, 117.2 (q), 114.8, 106.3, 66.5, 40.9.

6-(4-cyanophenoxy)-N-(3-(trifluoromethyl)phenyl)-2H-benzo[b][1,4]oxazine-4(3H)-carboxamide (SC-159)

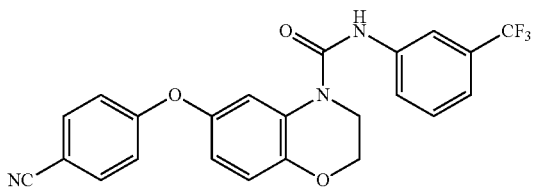 [SMILES: N#Cc1ccc(Oc2ccc3c(c2)N(C(=O)Nc2cccc(C(F)(F)F)c2)CCO3)cc1]

$^1$H NMR (300 MHz, CDCl$_3$-d$_1$): δ 7.61 (s, 1H), 7.58 (d, J=9.0 Hz, 2H), 7.51 (d, J=7.8 Hz, 1H), 7.40 (t, J=7.8 Hz, 1H), 7.31 (d, J=7.8 Hz, 1H), 7.18 (s, 1H), 7.11 (d, J=2.7 Hz, 1H), 7.01 (d, J=9.0 Hz, 1H), 6.97 (d, J=9.0 Hz, 2H), 6.83 (dd, J=9.0, 2.7 Hz, 1H), 4.32 (t, J=4.5 Hz, 2H), 3.95 (t, J=4.5 Hz, 2H); $^{13}$C NMR (75 MHz, CDCl$_3$-d$_1$): δ 162.0, 152.1, 148.0, 144.6, 138.5, 134.4, 131.6 (q), 129.7, 126.4, 123.9 (q), 122.7, 120.6 (q), 119.7, 118.8, 118.6, 117.5, 116.4 (q), 114.8, 106.1, 66.5, 40.9.

N-(4-(cyanomethyl)phenyl)-6-(4-cyanophenoxy)-2H-benzo[b][1,4]oxazine-4(3H)-carboxamide (SC-160)

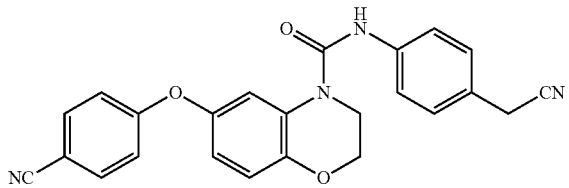 [SMILES: N#CCc1ccc(NC(=O)N2CCOc3ccc(Oc4ccc(C#N)cc4)cc32)cc1]

$^1$H NMR (300 MHz, CDCl$_3$-d$_1$): δ 7.57 (d, J=9.0 Hz, 2H), 7.34 (d, J=8.7 Hz, 2H), 7.24 (d, J=8.7 Hz, 2H), 7.12 (d, J=3.0 Hz, 1H), 7.10 (s, 1H), 7.01 (s, 1H), 6.97 (d, J=9.0 Hz, 2H), 6.81 (dd, J=8.7, 3.0 Hz, 1H), 4.31 (t, J=4.5 Hz, 2H), 3.95 (t, J=4.5 Hz, 2H), 3.69 (s, 2H); $^{13}$C NMR (75 MHz, CDCl$_3$-d$_1$): δ 162.0, 152.2, 147.9, 144.5, 137.9, 134.4, 128.8, 126.6, 125.3, 120.2, 119.6, 118.8, 118.3, 118.0, 117.5, 114.8, 106.1, 66.5, 40.9, 23.2.

6-(4-cyanophenoxy)-N-(3-ethynylphenyl)-2H-benzo[b][1,4]oxazine-4(3H)-carboxamide (SC-161)

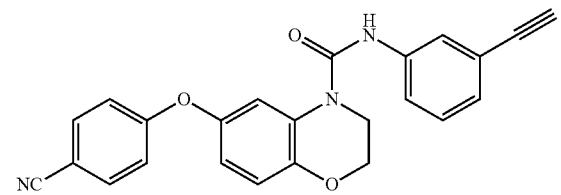 [SMILES: C#Cc1cccc(NC(=O)N2CCOc3ccc(Oc4ccc(C#N)cc4)cc32)c1]

$^1$H NMR (300 MHz, CDCl$_3$-d$_1$): δ 7.60 (d, J=9.0 Hz, 2H), 7.44 (d, J=8.1 Hz, 1H), 7.33 (s, 1H), 7.27~7.17 (m, 2H), 7.09 (d, J=3.0 Hz, 1H), 7.07 (s, 1H), 7.00 (d, J=8.7 Hz, 1H), 6.98 (d, J=9.0 Hz, 2H), 6.83 (dd, J=9.0, 2.7 Hz, 1H), 4.31 (t, J=4.5 Hz, 2H), 3.94 (t, J=4.5 Hz, 2H), 3.08 (s, 1H); $^{13}$C NMR (75 MHz, CDCl$_3$-d$_1$): δ 162.1, 152.1, 148.0, 144.6, 138.0, 134.4, 129.3, 127.7, 126.6, 123.1, 22.9, 120.1, 119.6, 118.9, 118.5, 117.5, 114.9, 106.2, 83.1, 77.87, 66.5, 40.8.

7-(4-cyanophenoxy)-N-(3-ethynylphenyl)-2H-benzo[b][1,4]oxazine-4(3H)-carboxamide (SC-162)

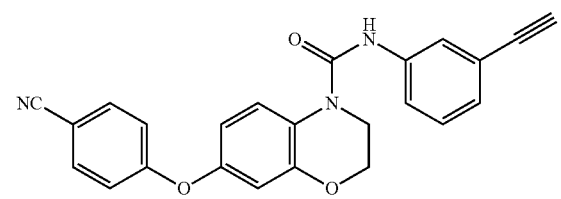 [SMILES: C#Cc1cccc(NC(=O)N2CCOc3cc(Oc4ccc(C#N)cc4)ccc32)c1]

$^1$H NMR (300 MHz, CDCl$_3$-d$_1$): δ 7.62 (d, J=9.0 Hz, 2H), 7.47 (d, J=9.0 Hz, 1H), 7.45 (s, 1H), 7.32 (d, J=8.7 Hz, 1H), 7.26~7.18 (m, 2H), 7.11 (s, 1H), 7.05 (d, J=9.0 Hz, 2H), 6.68

(s, 1H), 6.65 (d, J=2.7 Hz, 1H), 4.31 (t, J=4.5 Hz, 2H), 3.94 (t, J=4.5 Hz, 2H), 3.04 (s, 1H); $^{13}$C NMR (75 MHz, CDCl$_3$-d$_1$): δ 161.1, 153.1, 152.4, 148.7, 138.2, 134.4, 129.3, 127.6, 124.1, 123.0, 123.9, 122.8, 120.2, 118.8, 118.4, 112.7, 110.1, 106.6, 83.2, 77.7, 67.0, 40.6.

7-(4-cyanophenoxy)-N-(3-(trifluoromethyl)phenyl)-2H-benzo[b][1,4]oxazine-4(3H)-carboxamide (SC-163)

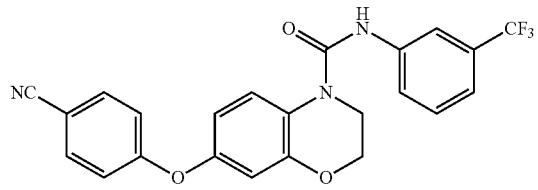 [SMILES: N#Cc1ccc(Oc2ccc3c(c2)OCCN3C(=O)Nc2cccc(C(F)(F)F)c2)cc1]

$^1$H NMR (300 MHz, CDCl$_3$-d$_1$): δ 7.67~7.57 (m, 4H), 7.42 (t, J=8.7 Hz, 1H), 7.35~7.31 (m, 2H), 7.23 (s, 1H), 7.06 (d, J=8.7 Hz, 2H), 6.70 (s, 1H), 6.68 (dd, J=7.8, 2.7 Hz, 1H), 4.32 (t, J=4.5 Hz, 2H), 3.96 (t, J=4.5 Hz, 2H); $^{13}$C NMR (75 MHz, CDCl$_3$-d$_1$): δ 161.1, 153.3, 152.4, 148.8, 138.7, 134.4, 131.6 (q), 129.7, 124.1, 124.0 (q), 122.7, 122.6, 120.4 (q), 118.8, 118.5, 116.3 (q), 112.8, 110.1, 106.7, 67.0, 40.7.

N-(3,5-bis(trifluoromethyl)phenyl)-7-(4-cyanophenoxy)-2H-benzo[b][1,4]oxazine-4(3H)-carboxamide (SC-164)

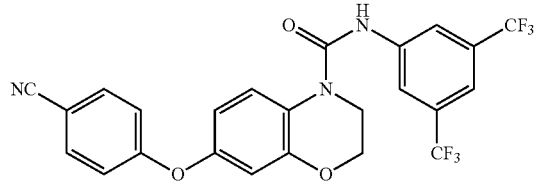 [SMILES: N#Cc1ccc(Oc2ccc3c(c2)OCCN3C(=O)Nc2cc(C(F)(F)F)cc(C(F)(F)F)c2)cc1]

$^1$H NMR (300 MHz, CDCl$_3$-d$_1$): δ 7.89 (s, 2H), 7.63 (d, J=8.7 Hz, 2H), 7.55 (s, 1H), 7.40 (s, 1H), 7.32 (d, J=9.9 Hz, 1H), 7.07 (d, J=8.7 Hz, 2H), 6.72 (d, J=6.6, 2.7 Hz, 1H), 6.70 (s, 1H), 4.33 (t, J=4.5 Hz, 2H), 3.97 (t, J=4.5 Hz, 2H); $^{13}$C NMR (75 MHz, CDCl$_3$-d$_1$): δ 160.9, 153.7, 152.1, 148.9, 139.8, 134.4, 132.6 (q), 125.0 (q), 124.1, 122.2, 119.3 (q), 118.7, 118.6, 117.1 (q), 112.9, 110.2, 106.8, 67.0, 40.7.

N-(4-chloro-3-(trifluoromethyl)phenyl)-7-(4-cyanophenoxy)-2H-benzo[b][1,4]oxazine-4(3H)-carboxamide (SC-165)

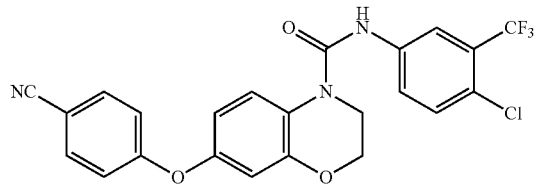 [SMILES: N#Cc1ccc(Oc2ccc3c(c2)OCCN3C(=O)Nc2ccc(Cl)c(C(F)(F)F)c2)cc1]

$^1$H NMR (300 MHz, CDCl$_3$-d$_1$): δ 7.69 (d, J=2.7 Hz, 1H), 7.64~7.56 (m, 3H), 7.42 (d, J=8.4 Hz, 1H), 7.31 (d, J=9.3 Hz, 1H), 7.23 (s, 1H), 7.06 (d, J=8.7 Hz, 2H), 6.71 (s, 1H), 6.68 (dd, J=6.9, 2.7 Hz, 1H), 4.32 (t, J=4.8 Hz, 2H), 3.95 (t, J=4.8 Hz, 2H); $^{13}$C NMR (75 MHz, CDCl$_3$-d$_1$): δ 161.0, 153.4, 152.2, 148.8, 137.1, 134.4, 132.1, 129.0 (q), 126.5 (q), 124.5 (q), 124.1, 123.6, 122.4, 118.8, 118.7, 118.6, 118.5, 112.8, 110.2, 106.7, 67.0, 40.7.

7-(4-cyanophenoxy)-N-(4-fluoro-3-(trifluoromethyl)phenyl)-2H-benzo[b][1,4]oxazine-4(3H)-carboxamide (SC-166)

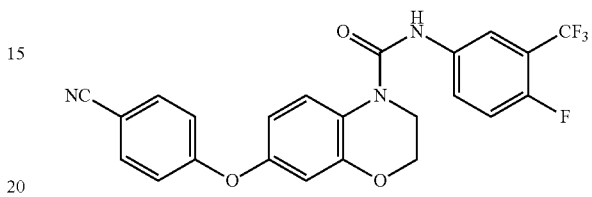

$^1$H NMR (300 MHz, CDCl$_3$-d$_1$): δ 7.62 (d, J=9.0 Hz, 2H), 7.61~7.55 (m, 2H), 7.32 (d, J=9.3 Hz, 1H), 7.17 (s, 1H), 7.14 (t, J=9.0 Hz, 1H), 7.06 (d, J=9.0 Hz, 2H), 6.70 (s, 1H), 6.67 (dd, J=8.4, 2.7 Hz, 1H), 4.32 (t, J=4.8 Hz, 2H), 3.95 (t, J=4.8 Hz, 2H); $^{13}$C NMR (75 MHz, CDCl$_3$-d$_1$): δ 161.1, 157.6 (d), 154.3 (d), 153.4, 152.5, 148.8, 134.4, 134.3, 134.3, 125.1 (d), 124.1, 122.5, 122.4 (q), 118.8 (q), 118.5, 117.6 (d), 112.8, 110.2, 106.7, 67.0, 40.7

N-(4-(cyanomethyl)phenyl)-7-(4-cyanophenoxy)-2H-benzo[b][1,4]oxazine-4(3H)-carboxamide (SC-167)

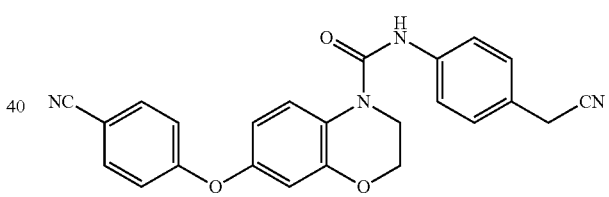

$^1$H NMR (300 MHz, CDCl$_3$-d$_1$): δ 7.61 (d, J=8.7 Hz, 2H), 7.40 (d, J=8.7 Hz, 2H), 7.33 (d, J=8.4 Hz, 1H), 7.25 (d, J=9.0 Hz, 2H), 7.15 (s, 1H), 7.05 (d, J=9.0 Hz, 2H), 6.68 (s, 1H), 6.65 (dd, J=8.4, 2.7 Hz, 1H), 4.31 (t, J=4.2 Hz, 2H), 3.94 (t, J=4.2 Hz, 2H), 3.69 (s, 2H); $^{13}$C NMR (75 MHz, CDCl$_3$-d$_1$): δ 161.1, 153.1, 152.5, 148.7, 138.1, 134.4, 128.8, 125.1, 124.1, 122.8, 120.2, 118.8, 118.4, 118.0, 112.8, 110.1, 106.6, 67.0, 40.7, 23.2.

1-(4-(4-(cyanomethyl)phenoxy)phenyl)-3-(4-fluoro-3-(trifluoromethyl) phenyl)urea (SC-168)

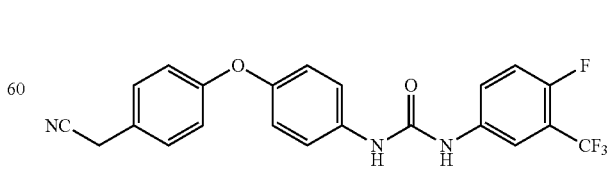

$^1$H NMR (300 MHz, DMSO-d$_6$): δ 9.02 (s, 1H), 8.82 (s, 1H), 8.01 (dd, J=6.6, 2.7 Hz, 1H), 7.67~7.61 (m, 1H), 7.48 (d, J=9.0 Hz, 2H), 7.43 (t, J=9.3 Hz, 1H), 7.34 (d, J=9.0 Hz,

2H), 6.99 (dd, J=9.0, 3.9 Hz, 4H), 4.00 (s, 2H); $^{13}$C NMR (75 MHz, DMSO-d$_6$): δ 157.0, 155.2 (d), 152.7, 151.9 (d), 150.8, 136.6 (d), 135.4, 129.7, 125.5, 124.4 (q), 124.2 (d), 120.4, 119.7, 119.4, 118.1, 117.6 (d), 116.4 (m), 115.9 (q), 21.6.

1-(4-(4-(cyanomethyl)phenoxy)phenyl)-3-(4-(cyanomethyl)phenyl)urea (SC-169)

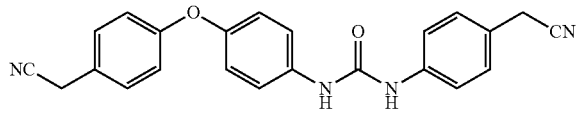 [SMILES: N#CCc1ccc(NC(=O)Nc2ccc(Oc3ccc(CC#N)cc3)cc2)cc1]

$^1$H NMR (300 MHz, DMSO-d$_6$): δ 8.73 (s, 1H), 8.71 (s, 1H), 7.47 (d, J=9.0 Hz, 4H), 7.33 (d, J=9.0 Hz, 2H), 7.25 (d, J=9.0 Hz, 2H), 6.99 (d, J=9.0, 3.0 Hz, 4H), 3.99 (s, 2H), 3.94 (s, 2H); $^{13}$C NMR (75 MHz, DMSO-d$_6$): δ 157.1, 152.6, 150.5, 139.2, 135.8, 129.7, 128.6, 125.5, 124.2, 120.0, 119.8, 119.5, 119.4, 118.5, 118.0, 21.7, 21.6.

1-(4-(4-(cyanomethyl)phenoxy)phenyl)-3-(3-ethynylphenyl)urea (SC-170)

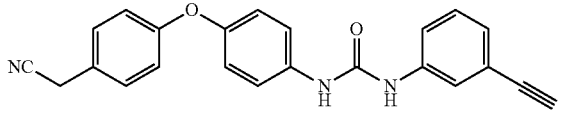 [SMILES: C#Cc1cccc(NC(=O)Nc2ccc(Oc3ccc(CC#N)cc3)cc2)c1]

$^1$H NMR (300 MHz, DMSO-d$_6$): δ 8.78 (s, 1H), 8.75 (s, 1H), 7.66 (s, 1H), 7.48 (d, J=9.0 Hz, 2H), 7.40 (d, J=8.4 Hz, 1H), 7.34 (d, J=9.0 Hz, 2H), 7.29 (d, J=8.4 Hz, 1H), 7.07 (d, J=8.4 Hz, 1H), 6.99 (dd, J=9.0, 3.0 Hz, 4H), 4.15 (s, 1H), 3.99 (s, 2H); $^{13}$C NMR (75 MHz, DMSO-d$_6$): δ 157.1, 152.5, 150.6, 140.0, 135.6, 129.7, 129.2, 125.5, 125.0, 122.0, 120.9, 120.1, 119.8, 119.4, 118.9, 118.0, 83.6, 80.4, 21.6.

1-(4-chloro-3-(trifluoromethyl)phenyl)-3-(4-(4-(cyanomethyl)phenoxy) phenyl)urea (SC-171)

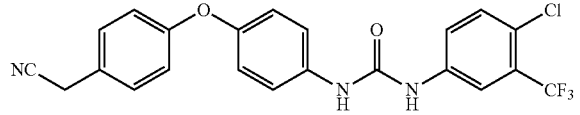 [SMILES: N#CCc1ccc(Oc2ccc(NC(=O)Nc3ccc(Cl)c(C(F)(F)F)c3)cc2)cc1]

$^1$H NMR (300 MHz, DMSO-d$_6$): δ 9.15 (s, 1H), 8.87 (s, 1H), 8.11 (d, J=2.4 Hz, 1H), 7.66~7.59 (m, 2H), 7.49 (d, J=9.0 Hz, 2H), 7.34 (d, J=9.0 Hz, 2H), 7.00 (d, J=9.0, 4.2 Hz, 4H), 4.00 (s, 2H); $^{13}$C NMR (75 MHz, DMSO-d$_6$): δ 157.0, 152.5, 150.9, 139.4, 135.3, 132.0, 129.7, 126.7 (q), 125.6, 122.8 (q), 123.0, 122.2 (q), 120.5, 119.7, 119.4, 118.1, 116.8 (q), 21.6.

1-(3,5-bis(trifluoromethyl)phenyl)-3-(4-(4-(cyanomethyl)phenoxy)phenyl) urea (SC-172)

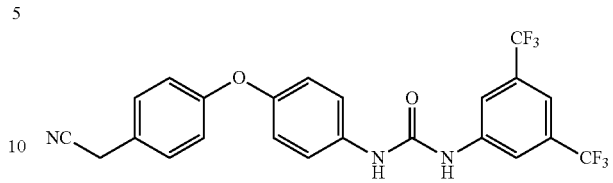

$^1$H NMR (300 MHz, DMSO-d$_6$): δ 9.39 (s, 1H), 9.02 (s, 1H), 8.14 (s, 2H), 7.63 (s, 1H), 7.51 (d, J=9.0 Hz, 2H), 7.34 (d, J=9.0 Hz, 2H), 7.01 (dd, J=9.0, 4.8 Hz, 4H), 4.00 (s, 2H); $^{13}$C NMR (75 MHz, DMSO-d$_6$): δ 157.0, 152.5, 151.1, 141.9, 135.1, 130.9 (q), 129.8, 125.6, 123.3 (q), 120.8, 119.7, 119.4, 118.2, 117.9 (q), 114.2 (q), 21.6.

1-(4-(4-(cyanomethyl)phenoxy)phenyl)-3-(3-(trifluoromethyl)phenyl)urea (SC-173)

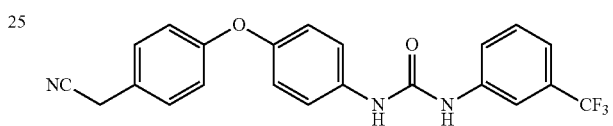

$^1$H NMR (300 MHz, DMSO-d$_6$): δ 9.05 (s, 1H), 8.84 (s, 1H), 8.01 (s, 1H), 7.54 (t, J=9.3 Hz, 2H), 7.49 (d, J=9.0 Hz, 2H), 7.36~7.29 (m, 3H), 7.00 (dd, J=9.0, 3.9 Hz, 4H), 4.00 (s, 2H); $^{13}$C NMR (75 MHz, DMSO-d$_6$): δ 157.1, 152.6, 150.8, 140.6, 135.5, 130.1 (q), 129.9, 129.7, 129.3, 125.5, 124.2 (q), 121.8, 120.3, 119.8, 119.4, 118.1, 114.1 (q), 21.6.

1-(4-chloro-3-(4-cyano-3-methylphenoxy)phenyl)-3-(3-(trifluoromethyl) phenyl)urea (SC-174)

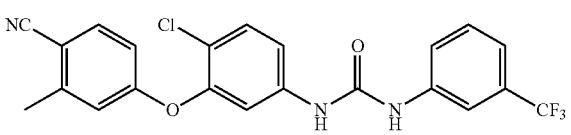 [SMILES: Cc1cc(Oc2cc(NC(=O)Nc3cccc(C(F)(F)F)c3)ccc2Cl)ccc1C#N]

$^1$H NMR (300 MHz, DMSO-d$_6$): δ 9.14 (s, 1H), 9.13 (s, 1H), 7.96 (s, 1H), 7.77 (d, J=8.7 Hz, 1H), 7.58~7.47 (m, 4H), 7.35~7.30 (m, 2H), 7.04 (d, J=2.1 Hz, 1H), 6.86 (dd, J=8.7, 2.7 Hz, 1H), 2.45 (s, 3H); $^{13}$C NMR (75 MHz, DMSO-d$_6$): δ 160.2, 152.3, 149.6, 144.5, 140.2, 140.1, 134.8, 130.8, 129.9, 129.5 (q), 124.1 (q), 122.1, 118.4 (q), 118.0, 117.8, 117.7, 116.7, 114.5, 114.4 (q), 112.1, 106.1, 20.0.

1-(4-chloro-3-(4-cyano-3-methylphenoxy)phenyl)-3-(4-chloro-3-(trifluoromethyl)phenyl)urea (SC-175)

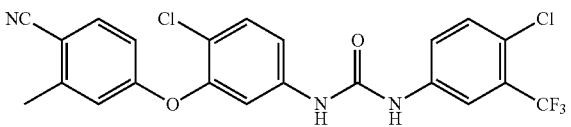 [SMILES: Cc1cc(Oc2cc(NC(=O)Nc3ccc(Cl)c(C(F)(F)F)c3)ccc2Cl)ccc1C#N]

¹H NMR (300 MHz, DMSO-d₆): δ 9.26 (s, 1H), 9.18 (s, 1H), 8.05 (d, J=2.4 Hz, 1H), 7.77 (d, J=8.4 Hz, 1H), 7.65 (s, 1H), 7.64 (s, 1H), 7.54 (d, J=8.4 Hz, 1H), 7.51 (d, J=2.7 Hz, 1H), 7.34 (dd, J=8.7, 2.4 Hz, 1H), 7.04 (d, J=2.4 Hz, 1H), 6.87 (dd, J=8.7, 2.7 Hz, 1H), 2.45 (s, 3H); ¹³C NMR (75 MHz, DMSO-d₆): δ 160.1, 152.2, 149.6, 144.6, 140.1, 139.0, 134.9, 132.0, 130.9, 126.7 (q), 123.4, 122.8 (q), 122.7, 118.0, 117.9, 117.8, 117.1 (q), 116.8, 114.5, 112.3, 106.1, 20.0.

1-(3,5-bis(trifluoromethyl)phenyl)-3-(4-chloro-3-(4-cyano-3-methylphenoxy) phenyl)urea (SC-176)

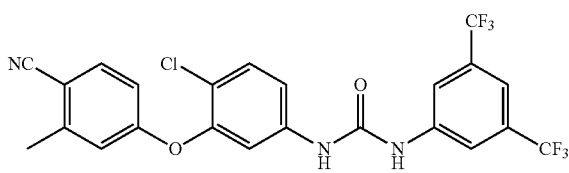 [SMILES: Cc1cc(Oc2cc(NC(=O)Nc3cc(C(F)(F)F)cc(C(F)(F)F)c3)ccc2Cl)ccc1C#N]

¹H NMR (300 MHz, DMSO-d₆): δ 9.48 (s, 1H), 9.32 (s, 1H), 8.11 (s, 2H), 7.77 (d, J=8.4 Hz, 1H), 7.65 (s, 1H), 7.55 (d, J=8.4 Hz, 1H), 7.53 (s, 1H), 7.38 (dd, J=9.0, 2.7 Hz, 1H), 7.04 (d, J=2.4 Hz, 1H), 6.87 (dd, J=8.4, 2.4 Hz, 1H), 2.45 (s, 3H); ¹³C NMR (75 MHz, DMSO-d₆): δ 160.2, 152.3, 149.6, 144.5, 141.5, 139.9, 134.8, 130.9, 130.7 (q), 123.3 (q), 118.3 (q), 118.2, 117.9, 117.8, 117.1, 114.7 (q), 114.5, 112.6, 106.1, 20.0.

1-(4-chloro-3-(4-cyano-3-methylphenoxy)phenyl)-3-(4-fluoro-3-(trifluoromethyl)phenyl)urea (SC-177)

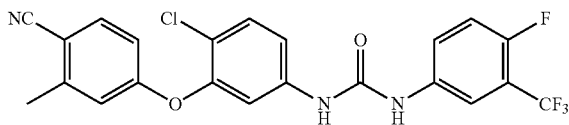 [SMILES: Cc1cc(Oc2cc(NC(=O)Nc3ccc(F)c(C(F)(F)F)c3)ccc2Cl)ccc1C#N]

¹H NMR (300 MHz, DMSO-d₆): δ 9.13 (s, 1H), 9.11 (s, 1H), 7.95 (dd, J=6.6, 2.4 Hz, 1H), 7.77 (d, J=8.4 Hz, 1H), 7.66~7.60 (m, 1H), 7.53 (d, J=8.4 Hz, 1H), 7.51 (s, 1H), 7.42 (t, J=9.9 Hz, 1H), 7.33 (dd, J=8.4, 2.4 Hz, 1H), 7.03 (d, J=2.4 Hz, 1H), 6.87 (dd, J=8.4, 2.7 Hz, 1H), 2.45 (s, 3H); ¹³C NMR (75 MHz, DMSO-d₆): δ 160.1, 155.4 (d), 152.4, 152.2 (d), 149.6, 144.5, 140.2, 136.2 (d), 134.8, 130.8, 124.6 (d), 122.6 (q), 118.0, 117.8, 117.7, 117.4, 116.7 (m), 116.3 (q), 114.5, 112.2, 106.1, 20.0.

1-(4-chloro-3-(3-chloro-4-cyanophenoxy)phenyl)-3-(3-(trifluoromethyl) phenyl)urea (SC-178)

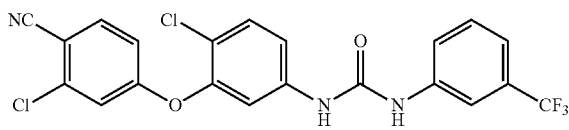 [SMILES: N#Cc1ccc(Oc2cc(NC(=O)Nc3cccc(C(F)(F)F)c3)ccc2Cl)cc1Cl]

¹H NMR (300 MHz, DMSO-d₆): δ 9.18 (s, 1H), 9.17 (s, 1H), 7.99~7.96 (m, 2H), 7.61~7.55 (m, 3H), 7.51 (t, J=7.8 Hz, 1H), 7.38~7.31 (m, 3H), 7.03 (dd, J=8.7, 2.7 Hz, 1H);

¹³C NMR (75 MHz, DMSO-d₆): δ 161.0, 152.3, 148.9, 140.4, 140.2, 137.3, 136.4, 131.0, 129.9, 129.5 (q), 124.2 (q), 122.1, 118.4 (q), 117.8, 117.6, 117.3, 115.9, 115.7, 114.4 (q), 112.3, 106.1.

1-(4-chloro-3-(3-chloro-4-cyanophenoxy)phenyl)-3-(4-chloro-3-(trifluoromethyl)phenyl)urea (SC-179)

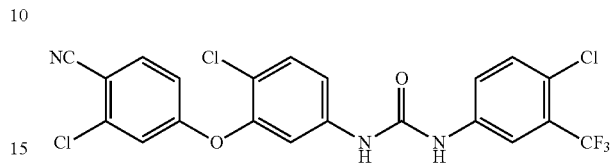

¹H NMR (300 MHz, DMSO-d₆): δ 9.31 (s, 1H), 9.24 (s, 1H), 8.07 (s, 1H), 7.98 (d, J=8.7 Hz, 1H), 7.66~7.56 (m, 4H), 7.39~7.35 (m, 2H), 7.03 (dd, J=8.7, 2.4 Hz, 1H); ¹³C NMR (75 MHz, DMSO-d₆): δ 161.0, 152.2, 148.9, 140.2, 139.0, 137.3, 136.4, 132.0, 131.0, 126.7 (q), 123.4, 122.8 (q), 122.7 (q), 117.8, 117.7, 117.4, 117.0 (q), 115.8, 115.7, 112.4, 106.2.

1-(3,5-bis(trifluoromethyl)phenyl)-3-(4-chloro-3-(3-chloro-4-cyanophenoxy) phenyl)urea (SC-180)

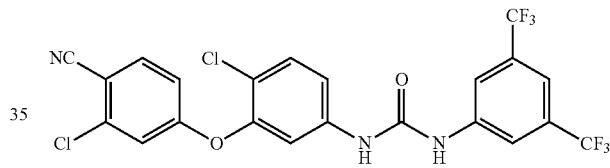

¹H NMR (300 MHz, DMSO-d₆): δ 9.52 (s, 1H), 9.37 (s, 1H), 8.11 (s, 2H), 7.97 (d, J=8.7 Hz, 1H), 7.66 (s, 1H), 7.61 (d, J=2.4 Hz, 1H), 7.58 (d, J=8.7 Hz, 1H), 7.41 (dd, J=8.7, 2.4 Hz, 1H), 7.38 (d, J=2.4 Hz, 1H), 7.03 (dd, J=8.7, 2.4 Hz, 1H); ¹³C NMR (75 MHz, DMSO-d₆): δ 161.0, 152.3, 148.9, 141.5, 140.1, 137.3, 136.4, 131.0, 130.7 (q), 123.3 (q), 118.3 (q), 118.1, 117.8, 117.7, 115.9, 115.6, 114.8 (q), 112.8, 106.2.

1-(4-chloro-3-(3-chloro-4-cyanophenoxy)phenyl)-3-(4-fluoro-3-(trifluoromethyl)phenyl)urea (SC-181)

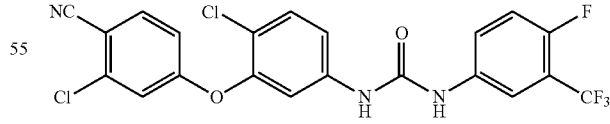

¹H NMR (300 MHz, DMSO-d₆): δ 9.19 (s, 1H), 9.17 (s, 1H), 7.99~7.94 (m, 2H), 7.66~7.61 (m, 1H), 7.59 (d, J=2.4 Hz, 1H), 7.56 (d, J=8.7 Hz, 1H), 7.43 (t, J=9.6 Hz, 1H), 7.38~7.35 (m, 2H), 7.02 (dd, J=8.7, 2.4 Hz, 1H); ¹³C NMR (75 MHz, DMSO-d₆): δ 161.0, 155.4 (d), 152.4, 152.1 (d), 148.9, 140.4, 137.3, 136.4, 136.2 (d), 131.0, 124.6 (d), 122.6 (q), 117.8, 117.7, 117.6, 117.5, 117.3, 116.2 (q), 115.9, 115.7, 112.4, 106.2.

1-(3,5-bis(trifluoromethyl)phenyl)-3-(4-chloro-3-((6-cyanopyridin-3-yl)oxy) phenyl)urea (SC-182)

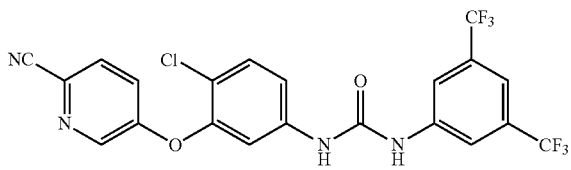 [SMILES: N#Cc1ccc(Oc2cc(NC(=O)Nc3cc(C(F)(F)F)cc(C(F)(F)F)c3)ccc2Cl)cn1]

$^1$H NMR (400 MHz, CDCl$_3$): δ 8.40 (d, J=2.4 Hz, 1H), 8.08 (dd, J=6.6, 2.4 Hz, 1H), 7.89 (s, 2H), 7.64 (s, 1H), 7.62 (s, 1H), 7.53 (s, 1H), 7.36 (s, 1H), 7.26 (dd, J=8.4, 2.4 Hz, 1H), 7.13 (t, J=9.6 Hz, 1H), 6.72 (t, J=4.8 Hz, 1H).

1-(3,5-bis(trifluoromethyl)phenyl)-3-(5-((6-cyanopyridin-3-yl)oxy)-2-fluorophenyl)urea (SC-183)

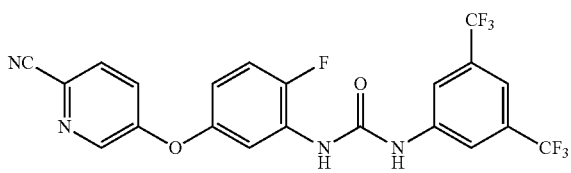 [SMILES: N#Cc1ccc(Oc2ccc(F)c(NC(=O)Nc3cc(C(F)(F)F)cc(C(F)(F)F)c3)c2)cn1]

$^1$H NMR (400 MHz, CDCl$_3$): δ 8.40 (d, J=2.4 Hz, 1H), 8.08 (dd, J=6.6, 2.4 Hz, 1H), 7.89 (s, 2H), 7.64 (s, 1H), 7.62 (s, 1H), 7.53 (s, 1H), 7.36 (s, 1H), 7.26 (dd, J=8.4, 2.4 Hz, 1H), 7.13 (t, J=9.6 Hz, 1H), 6.72 (t, J=4.8 Hz, 1H).

Bioactivity Assay

Effects of SC Derivatives on Phosphatase Activity in Recombinant SHP-1 RediPlate 96 EnzChek Tyrosine Phosphatase Assay kit (R-22067) was used for SHP-1 activity assay (Molecular Probes). Recombinant SHP-1 protein (25 ng) was reacted with SC derivatives at 1 μM for 2 hr. Then the SHP-1 phosphatase activity assay was performed according to the user's manual and the absorbance was measured at 465 nm. The SHP-1 activities of the SC derivatives are shown in table 7 below. The control group was DMSO, which functioned as the solvent of the SC derivatives. The values were expressed by mean±SD (N=3).
Effects of SC Derivatives on Cytotoxicity PLC5 cells (a hepatocellular carcinoma cell line) were seeded at 5×10$^3$ cells per well in 96-well plates. Then, cells were exposed to SC derivatives at the indicated doses for 72 h. After that, cells were incubated with MTT (1 mg/ml) (Sigma-Aldrich, St. Louis, Mo.) for 2 h at 37° C. Cell viability was then assessed by measuring the absorbance at 570 nm using a microplate reader. IC$_{50}$ (half maximal inhibitory concentration) of SC derivatives on PLC5 cancer cell line are shown in table 7 below, too.

TABLE 7

SC derivatives' SHP-1 activity and IC$_{50}$ of SC derivatives on PLC5 cancer cell line of tested compounds.

| Compound (SC-No.) | SHP-1 Activity (% of control) | IC$_{50}$ on PLC5 (μm) |
|---|---|---|
| Control* | 100 | — |
| 65 | 84.35 ± 22.40 | 1.41 |
| 66 | 93.26 ± 9.30 | >10 |
| 67 | 94.05 ± 16.11 | >10 |
| 68 | 84.36 ± 11.31 | >10 |
| 69 | 95.16 ± 6.91 | >10 |
| 70 | 91.23 ± 15.95 | >10 |
| 71 | 87.54 ± 10.21 | 0.21 |
| 72 | 131.47 ± 14.99 | 2.25 |
| 73 | 102.24 ± 17.36 | >10 |
| 75 | 111.30 ± 9.50 | >10 |
| 76 | 111.83 ± 12.47 | >10 |
| 78 | 113.65 ± 13.93 | >10 |
| 79 | 112.25 ± 0.60 | 0.82 |
| 80 | X91.93 ± 8.09 | 1.67 |
| 82 | 92.68 ± 5.66 | 4.14 |
| 83 | 110.68 ± 13.38 | 0.25 |
| 84 | 108.62 ± 10.55 | >10 |
| 85 | 91.42 ± 10.47 | >10 |
| 86 | 81.06 ± 7.61 | >10 |
| 87 | 264.67 ± 32.11 | 0.97 |
| 88 | 100.48 ± 13.31 | 1.05 |
| 89 | 143.45 ± 15.17 | 0.83 |
| 90 | 95.78 ± 10.66 | >10 |
| 91 | 99.99 ± 4.52 | >10 |
| 92 | 252.27 ± 10.78 | >10 |
| 93 | 94.07 ± 0.82 | >10 |
| 94 | 114.65 ± 13.55 | >10 |
| 96 | 194.52 ± 17.89 | 0.41 |
| 97 | 127.01 ± 9.02 | >10 |
| 98 | 88.80 ± 14.30 | 0.14 |
| 99 | 99.86 ± 3.65 | 0.18 |
| 100 | 94.38 ± 11.11 | 0.11 |
| 102 | 140.46 ± 12.56 | 0.16 |
| 103 | 123.75 ± 32.58 | 0.19 |
| 104 | 139.74 ± 4.92 | >10 |
| 105 | 424.63 ± 10.66 | 0.47 |
| 106 | 147.13 ± 8.51 | >10 |
| 107 | 149.03 ± 14.47 | >10 |
| 108 | 133.11 ± 12.03 | >10 |
| 109 | 143.61 ± 5.36 | 2.07 |
| 110 | 146.29 ± 12.80 | 7.65 |
| 111 | 156.55 ± 5.99 | 0.24 |
| 112 | 146.18 ± 14.74 | 0.49 |
| 113 | 153.49 ± 13.55 | >10 |
| 114 | 156.85 ± 6.04 | 0.76 |
| 131 | 327.86 ± 34.79 | 0.23 |
| 132 | 151.59 ± 9.68 | 0.64 |
| 133 | 253.18 ± 26.17 | 0.44 |
| 134 | 152.29 ± 7.92 | 0.74 |
| 135 | 153.32 ± 14.65 | 1.85 |
| 137 | 180.35 ± 35 | 0.49 |
| 138 | 196.54 ± 22.4 | 0.57 |
| 139 | 280.62 ± 16.62 | 0.31 |
| 140 | 140.81 ± 2.48 | 0.83 |
| 141 | 273.26 ± 86.35 | 0.28 |
| 142 | 249.66 ± 5.81 | 0.45 |
| 143 | 198.37 ± 32.5 | 0.61 |
| 144 | 159.94 ± 30.14 | 1.79 |
| 145 | 168.15 ± 1.97 | 0.85 |
| 146 | 139.68 ± 6.63 | 2.59 |
| 148 | 363.95 ± 18.11 | 0.22 |
| 149 | 140.90 ± 6.65 | 1.38 |
| 150 | 129.59 ± 59 | 2.23 |
| 151 | 136.00 ± 9.09 | 0.59 |
| 152 | 336.99 ± 50.76 | 0.34 |
| 153 | 135.54 ± 5.11 | 1.83 |
| 154 | 115.12 ± 3.84 | 0.62 |
| 156 | 112.47 ± 7.98 | 1.87 |
| 157 | 106.27 ± 6.28 | 1.76 |
| 158 | 102.07 ± 3.47 | 3.31 |
| 159 | 98.04 ± 8.80 | 2.56 |
| 160 | 116.47 ± 6.60 | 5.13 |
| 161 | 140.58 ± 11.39 | >10 |
| 162 | 141.39 ± 15.44 | 3.06 |

TABLE 7-continued

SC derivatives' SHP-1 activity and $IC_{50}$ of SC derivatives on PLC5 cancer cell line of tested compounds.

| Compound (SC-No.) | SHP-1 Activity (% of control) | $IC_{50}$ on PLC5 (μm) |
| --- | --- | --- |
| 163 | 142.36 ± 2.16 | 2.51 |
| 164 | 83.70 ± 10.90 | >10 |
| 165 | 169.27 ± 1.19 | >10 |
| 166 | 51.89 ± 8.16 | 1.32 |
| 167 | 110.58 ± 10.14 | 2.55 |
| 168 | 147.25 ± 78.63 | 1.07 |
| 169 | 126.25 ± 1.46 | >10 |
| 170 | 101.42 ± 7.86 | >10 |
| 171 | 116.66 ± 17.26 | 0.88 |
| 172 | 215.34 ± 12.22 | 0.41 |
| 173 | 110.75 ± 1.18 | >10 |
| 174 | 203.95 ± 30.20 | 1.46 |
| 175 | 233.37 ± 36.5 | 1.2 |
| 176 | 112.57 ± 3.69 | 0.65 |
| 177 | 103.52 ± 1.13 | >10 |
| 178 | 106.69 ± 9.47 | 1.49 |
| 179 | 99.11 ± 7.09 | 0.95 |
| 180 | 105.52 ± 0.87 | 0.78 |
| 181 | 106.88 ± 3.58 | 0.93 |
| 182 | 110.50 ± 6.08 | 0.56 |
| 183 | 353.11 ± 30.81 | 0.53 |

*Control is DMSO for SHP-1 activity assay

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A compound having a chemical structure below:

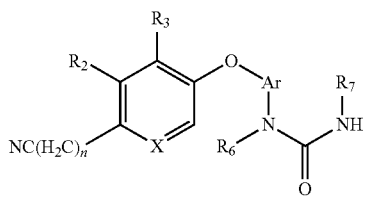

wherein n is 0 or 1;

X is N or C—$R_1$;

$R_1$ is H or Cl;

$R_2$ and $R_3$ are H, a halide or an alkyl group independently;

Ar is an unsubstituted or substituted phenylene group or a naphthalenylene group, wherein the substituted phenylene group is

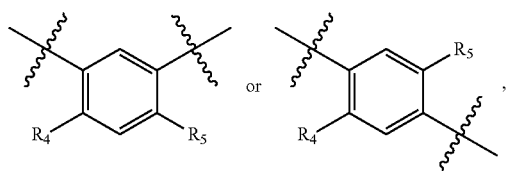

and the naphthalenylene group is

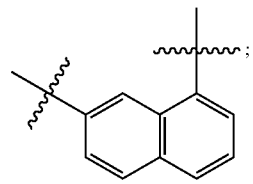

$R_4$ is H, a halide or an alkyl group;

$R_5$ is H, a halide, an alkyl group, an alkoxyl group or a hydroxyl group;

$R_6$ is H or a hydroxyl group;

$R_7$ is a substituted phenyl group, a substituted

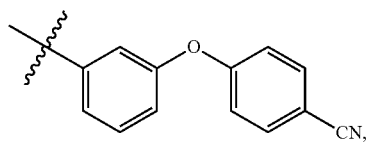

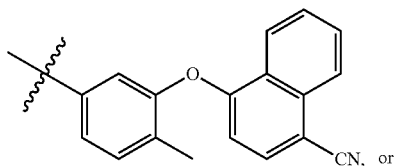

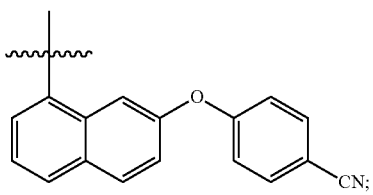

wherein the substituted phenyl group is selected from one of

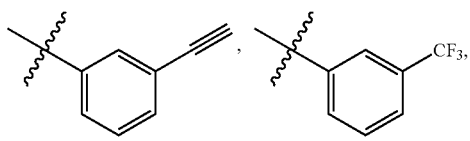

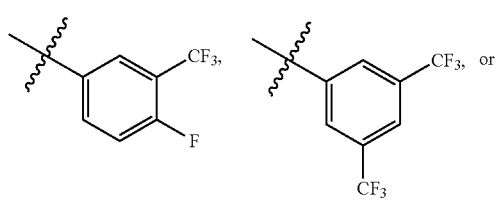

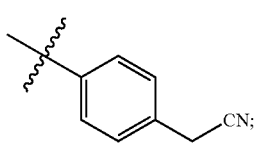

and
wherein the substituted

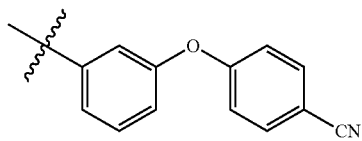 [SMILES: *c1cccc(Oc2ccc(C#N)cc2)c1]

is selected from one of

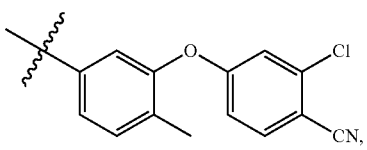

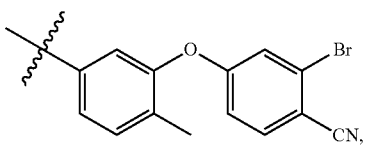

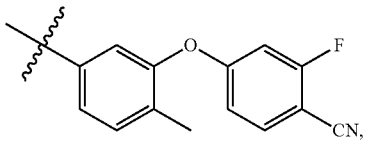

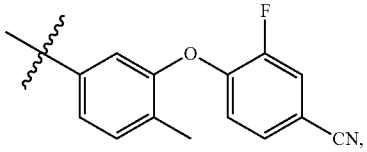

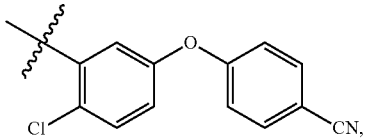

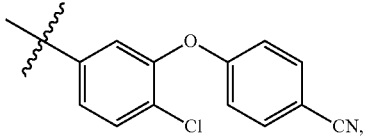

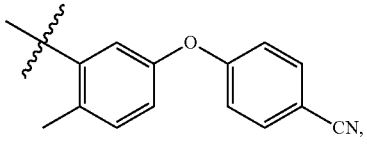

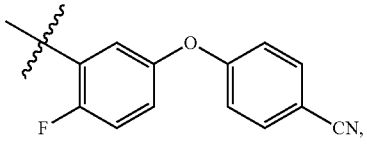

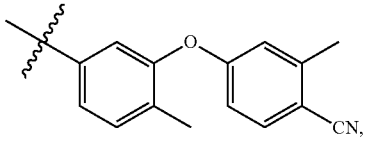

-continued

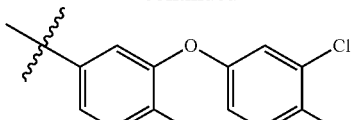

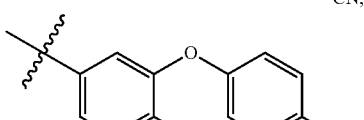

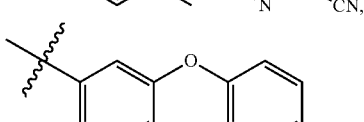

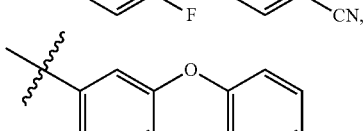

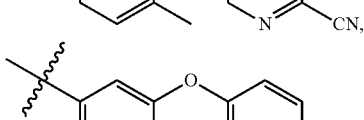

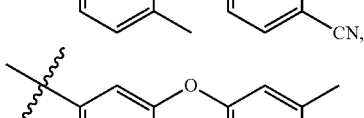

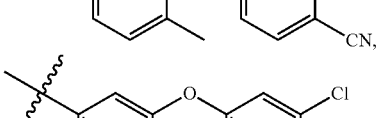

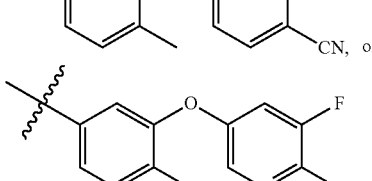

and
wherein, when $R_7$ is

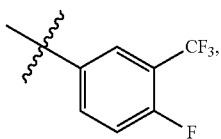 [SMILES: *c1ccc(F)c(C(F)(F)F)c1]

$R_2$, $R_3$, $R_4$, $R_5$, and $R_6$ are not H at a same time.

2. The compound of claim 1, wherein the halides of $R_2$ and $R_3$ are F, Cl, or Br independently.

3. The compound of claim 1, wherein the halides of $R_4$ and $R_5$ are F or Cl independently.

4. The compound of claim 1, wherein the alkyl groups of $R_2$, $R_3$, $R_4$ and $R_5$ are $CH_3$ or $CH_2CH_3$ independently.

5. A pharmaceutical composition, comprising:
   an effective amount of the compound in any one claim of the claims 1-4.

6. The pharmaceutical composition of claim 5, further comprising:
   a pharmaceutically acceptable carrier.

* * * * *